(12) United States Patent
Brown

(10) Patent No.: US 11,491,154 B2
(45) Date of Patent: *Nov. 8, 2022

(54) THERAPEUTIC BENEFIT OF SUBOPTIMALLY ADMINISTERED CHEMICAL COMPOUNDS

(71) Applicant: Dennis M. Brown, Menlo Park, CA (US)

(72) Inventor: Dennis M. Brown, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/783,137

(22) PCT Filed: Apr. 8, 2014

(86) PCT No.: PCT/US2014/033391
§ 371 (c)(1),
(2) Date: Oct. 8, 2015

(87) PCT Pub. No.: WO2014/168986
PCT Pub. Date: Oct. 16, 2014

(65) Prior Publication Data
US 2016/0045502 A1    Feb. 18, 2016

Related U.S. Application Data

(60) Provisional application No. 61/809,627, filed on Apr. 8, 2013.

(51) Int. Cl.
| A61K 31/513 | (2006.01) |
| A61K 45/06  | (2006.01) |
| A61K 9/28   | (2006.01) |
| A61K 9/20   | (2006.01) |
| A61K 31/133 | (2006.01) |
| A61K 31/565 | (2006.01) |
| A61K 31/417 | (2006.01) |

(52) U.S. Cl.
CPC .......... *A61K 31/513* (2013.01); *A61K 9/2059* (2013.01); *A61K 9/2866* (2013.01); *A61K 31/133* (2013.01); *A61K 31/417* (2013.01); *A61K 31/565* (2013.01); *A61K 45/06* (2013.01)

(58) Field of Classification Search
CPC .................................................... A61K 31/513
USPC ........................................................ 514/274
See application file for complete search history.

(56) References Cited

U.S. PATENT DOCUMENTS

| 2,969,364 | A | 1/1961 | Lyttle |
| 3,299,104 | A | 1/1967 | Fex et al. |
| 4,925,662 | A | 5/1990 | Oguchi et al. |
| 5,035,878 | A | 7/1991 | Borch et al. |
| 5,093,330 | A | 3/1992 | Caravatti et al. |
| 5,461,076 | A | 10/1995 | Stanek et al. |
| 5,747,498 | A | 5/1998 | Schnur et al. |
| 6,011,069 | A | 1/2000 | Inomata et al. |
| 6,121,245 | A | 9/2000 | Firshein |
| 6,277,835 | B1 | 8/2001 | Brown |
| 6,326,390 | B1 | 12/2001 | Leung et al. |
| 6,326,469 | B1 | 12/2001 | Ullrich et al. |
| 6,413,494 | B1 * | 7/2002 | Lee ......................... A61K 9/286 127/29 |
| 6,443,898 | B1 | 9/2002 | Unger et al. |
| 6,930,115 | B2 | 8/2005 | Fujii et al. |
| 7,318,931 | B2 | 1/2008 | Okumu et al. |
| 7,557,107 | B2 | 7/2009 | Zhu et al. |
| 7,619,005 | B2 | 11/2009 | Epstein et al. |
| 7,652,038 | B2 | 1/2010 | Cooke et al. |
| 7,691,887 | B2 | 4/2010 | Balkovec et al. |
| 7,700,773 | B2 | 4/2010 | Mallams et al. |
| 7,728,042 | B2 | 6/2010 | Eros et al. |
| 7,732,436 | B2 | 6/2010 | Tepe |
| 7,740,846 | B2 | 6/2010 | Gerber et al. |
| 7,750,007 | B2 | 7/2010 | Bearss et al. |
| 7,763,253 | B2 | 7/2010 | Hedlund et al. |
| 7,825,129 | B2 | 11/2010 | Pellicciari et al. |
| 7,879,896 | B2 | 2/2011 | Allegretti et al. |
| 7,910,621 | B2 | 3/2011 | Chen et al. |
| 7,928,105 | B2 | 4/2011 | Gangloff et al. |
| 7,928,248 | B2 | 4/2011 | Do et al. |
| 7,956,064 | B2 | 6/2011 | Chua et al. |
| 3,008,281 | A1 | 8/2011 | Prendergast et al. |
| 3,008,491 | A1 | 8/2011 | Jiang et al. |

(Continued)

FOREIGN PATENT DOCUMENTS

| WO | 9702266 A1 | 1/1997 |
| WO | 9739768 A1 | 10/1997 |

(Continued)

OTHER PUBLICATIONS

Kennedy et al., "Uracil Mustard Revisited," Cancer 85: 2265-2272 (1999).*

(Continued)

*Primary Examiner* — Nizal S Chandrakumar

(74) *Attorney, Agent, or Firm* — Ditthavong, Steiner & Mlotkowski

(57) ABSTRACT

The present invention describes methods and compositions for improving the therapeutic efficacy of therapeutic agents previously limited by suboptimal therapeutic performance by either improving efficacy as monotherapy or reducing side effects. Such methods and compositions are particularly applicable to mustard-based alkylating agents such as uracil mustard and analogs, derivatives, or prodrugs thereof, including 6-methyluracil mustard and 6-ethyluracil mustard.

2 Claims, No Drawings

(56) References Cited

U.S. PATENT DOCUMENTS

| | | |
|---|---|---|
| 3,012,976 A1 | 9/2011 | Wang et al. |
| 8,034,834 B2 | 10/2011 | Du et al. |
| 8,039,273 B2 | 10/2011 | Jeffrey |
| 8,058,275 B2 | 11/2011 | Xu et al. |
| 8,084,471 B2 | 12/2011 | Hamilton et al. |
| 8,088,749 B2 | 1/2012 | Simeone et al. |
| 8,088,760 B2 | 1/2012 | Chu et al. |
| 8,088,803 B2 | 1/2012 | Combs et al. |
| 8,106,197 B2 | 1/2012 | Cui et al. |
| 8,119,652 B2 | 2/2012 | Hamblett et al. |
| 8,119,654 B2 | 2/2012 | Jagtap et al. |
| 8,119,685 B2 | 2/2012 | Heidebrecht et al. |
| 8,129,399 B2 | 3/2012 | Binch et al. |
| 8,143,251 B2 | 3/2012 | Zhuo et al. |
| 8,148,393 B2 | 4/2012 | Van Dalen et al. |
| 8,158,616 B2 | 4/2012 | Rodgers et al. |
| 8,158,672 B2 | 4/2012 | Muller et al. |
| 8,178,125 B2 | 5/2012 | Wen et al. |
| 8,183,245 B2 | 5/2012 | Guerin et al. |
| 8,183,250 B2 | 5/2012 | Penning et al. |
| 8,188,075 B2 | 5/2012 | Ying et al. |
| 8,188,103 B2 | 5/2012 | Van Der Aa et al. |
| 8,193,182 B2 | 6/2012 | Ren et al. |
| 8,207,143 B2 | 6/2012 | Cheng |
| 8,207,169 B2 | 6/2012 | Furuyama et al. |
| 8,207,186 B2 | 6/2012 | Jewell et al. |
| 8,207,195 B2 | 6/2012 | Navratil et al. |
| 8,217,070 B2 | 7/2012 | Zhu et al. |
| 8,217,076 B2 | 7/2012 | Williams et al. |
| 8,222,269 B2 | 7/2012 | Dinsmore et al. |
| 8,222,451 B2 | 7/2012 | Kozikowski et al. |
| 8,227,605 B2 | 7/2012 | Shipps, Jr. et al. |
| 8,227,636 B2 | 7/2012 | Miller et al. |
| 8,231,898 B2 | 7/2012 | Oshlack et al. |
| 8,232,318 B2 | 7/2012 | Lee et al. |
| 8,236,543 B2 | 8/2012 | Roiz et al. |
| 8,236,802 B2 | 8/2012 | Xu et al. |
| 8,236,812 B2 | 8/2012 | Honigberg et al. |
| 8,242,080 B2 | 8/2012 | Kuriyan et al. |
| 8,242,103 B2 | 8/2012 | Lewis et al. |
| 8,242,104 B2 | 8/2012 | Blaquiere et al. |
| 8,242,106 B2 | 8/2012 | Howbert et al. |
| 8,242,109 B2 | 8/2012 | Glick |
| 8,242,252 B2 | 8/2012 | McDonagh et al. |
| 8,242,270 B2 | 8/2012 | Lajeunesse et al. |
| 8,247,416 B2 | 8/2012 | Menear et al. |
| 8,252,930 B2 | 8/2012 | Stoit et al. |
| 8,258,256 B2 | 9/2012 | Denmeade et al. |
| 8,268,811 B2 | 9/2012 | Mortimore et al. |
| 8,268,819 B2 | 9/2012 | Jin et al. |
| 8,268,827 B2 | 9/2012 | Branca et al. |
| 8,269,017 B2 | 9/2012 | Sun et al. |
| 8,277,807 B2 | 10/2012 | Gallagher et al. |
| 8,299,077 B2 | 10/2012 | Berthel et al. |
| 8,299,088 B2 | 10/2012 | Matteucci et al. |
| 8,299,256 B2 | 10/2012 | Vialard et al. |
| 8,309,573 B2 | 11/2012 | Fujio et al. |
| 8,318,719 B2 | 11/2012 | Dewdney et al. |
| 8,324,200 B2 | 12/2012 | Li et al. |
| 8,324,211 B2 | 12/2012 | Dewdney et al. |
| 8,324,262 B2 | 12/2012 | Yuan et al. |
| 8,324,282 B2 | 12/2012 | Gerson et al. |
| 8,329,736 B2 | 12/2012 | Chimmanamada et al. |
| 8,338,477 B2 | 12/2012 | Duncan et al. |
| 8,344,162 B2 | 1/2013 | Jung et al. |
| 8,372,451 B2 | 2/2013 | Vuckovic |
| 8,372,830 B2 | 2/2013 | Liu et al. |
| 8,372,979 B2 | 2/2013 | Welzig et al. |
| 8,377,897 B2 | 2/2013 | Teng et al. |
| 8,377,938 B2 | 2/2013 | Matsushima et al. |
| 8,377,943 B2 | 2/2013 | Sapountzis et al. |
| 8,377,961 B2 | 2/2013 | Lacrampe et al. |
| 8,377,962 B2 | 2/2013 | Parsy et al. |
| 8,378,108 B2 | 2/2013 | Corkey et al. |
| 8,378,117 B2 | 2/2013 | Liotta et al. |
| 8,435,539 B2 | 5/2013 | McBride et al. |
| 8,470,323 B2 | 6/2013 | Stanley et al. |
| 8,476,284 B2 | 7/2013 | Honigberg et al. |
| 8,492,383 B2 | 7/2013 | Panasci et al. |
| 8,497,277 B2 | 7/2013 | Honigberg et al. |
| 8,501,724 B1 | 8/2013 | Chen et al. |
| 8,501,751 B2 | 8/2013 | Honigberg et al. |
| 8,518,371 B2 | 8/2013 | Lee et al. |
| 8,530,434 B2 | 9/2013 | Ba et al. |
| 8,552,010 B2 | 10/2013 | Honigberg et al. |
| 8,563,563 B2 | 10/2013 | Honigberg et al. |
| 8,568,728 B2 | 10/2013 | Jeffrey |
| 8,580,782 B2 | 11/2013 | Guzi et al. |
| 8,591,886 B2 | 11/2013 | Ponath et al. |
| 8,591,892 B2 | 11/2013 | Alinari et al. |
| 8,613,930 B2 | 12/2013 | Chari et al. |
| 8,632,752 B2 | 1/2014 | McBride et al. |
| 8,637,490 B2 | 1/2014 | Peng et al. |
| 8,652,484 B2 | 2/2014 | McBride et al. |
| 8,658,653 B2 | 2/2014 | Honigberg et al. |
| 8,664,278 B2 | 3/2014 | Monso et al. |
| 8,680,243 B2 | 3/2014 | Funahashi |
| 9,066,918 B2 * | 6/2015 | Brown ................... A61K 31/44 |
| 9,687,466 B2 * | 6/2017 | Bacha .................. C12Q 1/6886 |
| 2001/0049349 A1 | 12/2001 | Chinery et al. |
| 2002/0131967 A1 | 9/2002 | Nakamura et al. |
| 2003/0158118 A1 | 8/2003 | Weidner |
| 2004/0023290 A1 | 2/2004 | Griffin et al. |
| 2004/0072889 A1 | 4/2004 | Masferrer |
| 2006/0100226 A1 | 5/2006 | Sikorski et al. |
| 2006/0229277 A1 | 10/2006 | Joshi |
| 2007/0207952 A1 | 9/2007 | Silva et al. |
| 2008/0039429 A1 | 2/2008 | Allen et al. |
| 2008/0125397 A1 | 5/2008 | Lui et al. |
| 2008/0125398 A1 | 5/2008 | Ma et al. |
| 2008/0166428 A1 | 7/2008 | Brown et al. |
| 2008/0213249 A1 | 9/2008 | Sinha et al. |
| 2008/0269133 A1 | 10/2008 | Zhang et al. |
| 2009/0074762 A1 | 3/2009 | Culp |
| 2009/0105233 A1 | 4/2009 | Chua et al. |
| 2009/0202540 A1 | 8/2009 | Gant |
| 2009/0258847 A1 | 10/2009 | Schreiner et al. |
| 2009/0274698 A1 | 11/2009 | Bhagwat et al. |
| 2009/0275519 A1 | 11/2009 | Nash et al. |
| 2010/0022482 A1 | 1/2010 | Baumann et al. |
| 2010/0048579 A1 | 2/2010 | Arista |
| 2010/0069458 A1 | 3/2010 | Atadja et al. |
| 2010/0075963 A1 | 3/2010 | Lehr et al. |
| 2010/0093647 A1 | 4/2010 | Liu et al. |
| 2010/0098691 A1 | 4/2010 | Goh et al. |
| 2010/0111901 A1 | 5/2010 | Gant et al. |
| 2010/0150896 A1 | 6/2010 | Gant et al. |
| 2010/0151003 A1 | 6/2010 | Trikha et al. |
| 2010/0166872 A1 | 7/2010 | Singh et al. |
| 2010/0173013 A1 | 7/2010 | Drygin et al. |
| 2010/0184706 A1 | 7/2010 | Bachovchin et al. |
| 2010/0190749 A1 | 7/2010 | Ren et al. |
| 2010/0209420 A1 | 8/2010 | Lamb et al. |
| 2010/0209479 A1 | 8/2010 | Carroll et al. |
| 2010/0227831 A1 | 9/2010 | Saha |
| 2010/0261758 A1 | 10/2010 | Arista et al. |
| 2010/0278833 A1 | 11/2010 | Stengel et al. |
| 2010/0286178 A1 | 11/2010 | Ibrahim et al. |
| 2010/0291025 A1 | 11/2010 | Rao et al. |
| 2010/0310503 A1 | 12/2010 | Li et al. |
| 2010/0311678 A1 | 12/2010 | Bean et al. |
| 2011/0021440 A1 | 1/2011 | Martin et al. |
| 2011/0028422 A1 | 2/2011 | Aloyz et al. |
| 2011/0039840 A1 | 2/2011 | Varasi et al. |
| 2011/0046071 A1 | 2/2011 | Karasik et al. |
| 2011/0053968 A1 | 3/2011 | Zhang |
| 2011/0071115 A1 | 3/2011 | Haddach et al. |
| 2011/0071136 A1 | 3/2011 | Haddach et al. |
| 2011/0086113 A1 | 4/2011 | Velasco Diez et al. |
| 2011/0105474 A1 | 5/2011 | Thaler et al. |
| 2011/0110936 A1 | 5/2011 | Nam et al. |
| 2011/0152240 A1 | 6/2011 | Haddach et al. |
| 2011/0165154 A1 | 7/2011 | Afar |
| 2011/0190509 A1 | 8/2011 | Chen et al. |

(56) References Cited

U.S. PATENT DOCUMENTS

| | | |
|---|---|---|
| 2011/0195066 A1 | 8/2011 | Zhang |
| 2011/0206661 A1 | 8/2011 | Zhang et al. |
| 2011/0212102 A1 | 9/2011 | Lehmann-Lintz et al. |
| 2011/0212103 A1 | 9/2011 | Heckel et al. |
| 2011/0256241 A1 | 10/2011 | Ramirez De Molina et al. |
| 2011/0263526 A1 | 10/2011 | Satyam |
| 2011/0268658 A1 | 11/2011 | Crawford et al. |
| 2011/0275607 A1 | 11/2011 | Shacham et al. |
| 2011/0288023 A1 | 11/2011 | Kamei et al. |
| 2011/0301184 A1 | 12/2011 | Lane |
| 2011/0305777 A1 | 12/2011 | Condon et al. |
| 2011/0318430 A1 | 12/2011 | Meruelo et al. |
| 2012/0028266 A1 | 2/2012 | Wells et al. |
| 2012/0065230 A1 | 3/2012 | Ba et al. |
| 2012/0087892 A1 | 4/2012 | Gutkind et al. |
| 2012/0114676 A1 | 5/2012 | Thompson et al. |
| 2012/0114765 A1 | 5/2012 | Cao et al. |
| 2012/0122838 A1 | 5/2012 | Ren et al. |
| 2012/0122885 A1 | 5/2012 | Salituro et al. |
| 2012/0128686 A1 | 5/2012 | Austen et al. |
| 2012/0129881 A1 | 5/2012 | Burke et al. |
| 2012/0164075 A1 | 6/2012 | Ahmad et al. |
| 2012/0165329 A1 | 6/2012 | Ibrahim et al. |
| 2012/0177748 A1 | 7/2012 | Charrier et al. |
| 2012/0183596 A1 | 7/2012 | Boulikas |
| 2012/0207857 A1 | 8/2012 | Siede et al. |
| 2012/0213844 A1 | 8/2012 | Huang et al. |
| 2012/0213854 A1 | 8/2012 | Feizer |
| 2012/0219541 A1 | 8/2012 | Chen et al. |
| 2012/0230991 A1 | 9/2012 | Graham et al. |
| 2013/0142867 A1 | 6/2013 | Yu et al. |
| 2013/0157257 A1 | 6/2013 | Bachinger |
| 2013/0164816 A1 | 6/2013 | Chang et al. |
| 2013/0195852 A1 | 8/2013 | Buggy et al. |
| 2013/0195987 A1 | 8/2013 | Breitenkamp et al. |
| 2013/0210756 A1 | 8/2013 | Kim et al. |
| 2013/0216531 A1 | 8/2013 | Jain et al. |
| 2013/0231359 A1 | 9/2013 | Chong et al. |
| 2013/0266666 A1 | 10/2013 | Moneo Ocana et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0005148 A1 | 1/2014 | Neelakantan et al. |
| 2014/0031535 A1 | 1/2014 | Jeffrey |
| 2014/0039186 A1 | 2/2014 | Honigberg et al. |
| 2014/0079690 A1 | 3/2014 | Buggy et al. |
| 2014/0080844 A1 | 3/2014 | Chen et al. |
| 2014/0086832 A1 | 3/2014 | McBride et al. |
| 2014/0088021 A1 | 3/2014 | Riggs-Sauthier et al. |

FOREIGN PATENT DOCUMENTS

| | | | | |
|---|---|---|---|---|
| WO | 9835958 A1 | 8/1998 | | |
| WO | 9917804 A1 | 4/1999 | | |
| WO | 0009495 A1 | 2/2000 | | |
| WO | 0059509 A1 | 10/2000 | | |
| WO | 0222577 A2 | 3/2002 | | |
| WO | 02092599 A1 | 11/2002 | | |
| WO | 03070823 A2 | 8/2003 | | |
| WO | 2004043466 A1 | 5/2004 | | |
| WO | WO 2012024367 | * | 2/2012 | ............. A01N 31/00 |

OTHER PUBLICATIONS

Institoris, Biochem. J. (1980) 185, 659-666.*
Chuten Cancer 47:442-451, 1981.*
Kerpel-Fronius, Cancer Chemother Pharmacol (1986) 16: 264-268.*
Janes, Adv Drug Deliv Rev, 47, 1, pp. (83-97), 0169-409.*
Coviello, J Control Release, 119, 1, pp. (5-24), 1873-4995.*
Mischler, 1979 Cancer Treatment Reviews 6: 191-204.*
Colvin in Cancer Medicine, Holland-Frei Cancer Medicine. 6th edition. Kufe et al., editors.Hamilton (ON): BC Decker; 2003.*
Bjergaard, Blood, Jun. 1, 2000 • vol. 95, No. 11.*
Kohn, Nucleic Acids Research (1987), 15(24), 10531-49.*
Venkatesh et al., J. Pharm. Sci. 89, 145-54 (2000).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Gawin, Bioorganic & Medicinal Chemistry 16 (2008) 8379-8389, p. 8381.*
Dorwald F. A. Side Reactions in Organic Synthesis, 2005, Wiley: VCH, Weinheim p. IX of Preface p. 1-15.*
Ellis et al., "Progress in Medicinal Chemistry", E-Book: Elsevier Science & Technology, 1971, vol. 8, pp. 101-104.
Maliepaard et al., "Overexpression of the BCRP/MXR/ABCP Gene in a topotecan-selected ovarian tumor cell line", Cancer Research, Sep. 15, 1999, vol. 59, No. 18, retrieved on Apr. 21, 2016 from http://cancerres.aacrjournals.org/content/59/18/4559.full.pdf, 6 Pages.
Ng et al., "Antiangiogenic activity of N-substituted and tetrafluorinated thalidomide analogues", American Association for Cancer Research, Jun. 15, 2003, vol. 63, No. 12, retrieved on Apr. 21, 2016 from http://cancerres.aacrjournals.org/content/63/12/3189.full.pdf, 7 Pages.
Baraldi et al., "Design, Synthesis, and Biological Activity of Hybrid Compounds between Uramustine and DNA Minor Groove Binder Distamycin A", Journal of Medicinal Chemistry, Jul. 13, 2002, vol. 45, No. 17, 9 Pages.
Fabrissin et al., "Synthesis and Anticancer Activity of 5-Diethylaminomethyl Derivatives and Nitrogen Mustards of Uracil and 2-Thiouracils", Journal of Medicinal Chemistry, May 1976, vol. 19, No. 5, 4 Pages.
Mattes et al., "DNA Sequence Selectivity of Guanine-N7 Alkylation by Nitrogen Mustards", Article in Nucleic Acids Research, Apr. 11, 1986, vol. 14, No. 7, 17 Pages.
O'Connor et al., "Comparative Pharmacokinetics of DNA Lesion Formation and Removal Following Treatment of L1210 Cells with Nitrogen Mustards", Article in Cancer Communications, 1990, vol. 2, No. 12, 5 Pages.
Kennedy et al., "Uracil Mustard Revisited", Cancer, May 15, 1999, vol. 85, No. 10, retrieved on Apr. 21, 2016 from http://onlinelibrary.wiley.com/doi/10.1002/(SICI)1097-0142(19990515)85:10%3C2265::AID-CNCR23%3E3.0.CO;2-9/pdf, 8 Pages.
Wertins et al., "In Vitro Evaluation of Dimethane Sulfonate Analogues with Potential Alkylating Activity and Selective Renal Cell Carcinoma cytotoxicity", Molecular Cancer Therapeutics, Jul. 2004, vol. 3, No. 7, retrieved on Apr. 21, 2016 from http://mct.aacrjournals.org/content/3/7/849.full.pdf, 13 Pages.
Shah et al., "Multiple BCR-ABL Kinase Domain Mutations Confer Polyclonal Resistance to the Tyrosine Kinase Inhibitor Imatinib (STI571) in Chronic Phase and Blast Crisis Chronic Myeloid Leukemia", Cancer Cell, Aug. 2002, Vo. 2, No. 2, pp. 117-125.
Gaurnier-Hausser et al., "NEMO-Binding Domain Peptide Inhibits Constitutive NF-kB Activity and Reduces Tumor Burden in a Canine Model of Relapsed, Refractory Diffuse Large B-Cell Lymphoma", Clinical Cancer Research, May 24, 2011, vol. 17, No. 14, 12 Pages.
Rusch et al., "Overexpression of the Epidermal Growth Factor Receptor and its Ligand Transforming Growth Factor Alpha is Frequent in Resectable Non-Small Cell Lung Cancer but Does Not Predict Tumor Progression", Clinical Cancer Research, Apr. 1997, vol. 3, No. 4, retrieved on Apr. 21, 2016 from http://clincancerres.aacrjournals.org/content/3/4/515.full.pdf, 9 Pages.
Yong-Chao et al., "Identification of the Binding Site for Gqα on its Effector Bruton's Tyrosine Kinase", Article in Proceedings of the National Academy of Sciences, Oct. 13, 1998, vol. 95, No. 21, retrieved on Apr. 21, 2016 from http://www.pnas.org/content/95/21/12197.full.pdf, 5 Pages.
Calabretta et al., "Altered Expression of G1-Specific Genes in Human Malignant Myeloid Cells", Article in Proceedings of the National Academy of Sciences, Mar. 1986, vol. 83, No. 5, retrieved on Apr. 21, 2016 from http://europepmc.org/backend/ptpmcrender.fcgi?accid=PMC323103&blobtype=pdf, 4 Pages.
Yasuda et al., "Cbl-b Positively Regulates Btk-Mediated Activation of Phospholipase C-γ2 in B cells", The Journal of Experimental Medicine, Jun. 24, 2002, vol. 196, No. 1, retrieved on Apr. 21, 2016 from http://jem.rupress.org/content/196/1/51.full.pdf, 13 Pages.

(56) References Cited

OTHER PUBLICATIONS

Akinleye et al., "Ibrutinib and Novel BTK Inhibitors in Clinical Development", Journal of Hematology & Oncology, Aug. 18, 2013, vol. 6, No. 59, 9 Pages.

Child et al., "High-Dose Chemotherapy with Hematopoietic Stem-Cell Rescue for Multiple Myeloma", The New England Journal of Medicine, May 8, 2003, vol. 348, No. 19, retrieved on Apr. 21, 2016 from http://myeloma.org/pdrs/10_Steps/Step05/2003-NEJM-Child-High-Dose-Chemotherapy-with-hematopoietic%20stem-cell%20rescue-in-MM.pdf, 9 Pages.

Hideshima et al., "The Proteasome Inhibitor PS-341 Inhibits Growth, Induces Apoptosis, and Overcomes Drug Resistance in Human Multiple Myeloma Cells", Cancer Research, Apr. 1, 2001, vol. 61, No. 7, retrieved on Apr. 21, 2016 from http://cancerres.aacrjournals.org/content/61/7/3071.full.pdf, 7 Pages.

Vuyyuri et al., "Evaluation of D-Methionine as a Novel Oral Radiation Protector for Prevention of Mucositis", Clinical Cancer Research, Apr. 1, 2008, vol. 14, No. 7, 11 Pages.

Hingorani et al., "Inhibition of Repair of Radiation-Induced DNA Damage Enhances Gene Expression from Replication-Defective Adenoviral Vectors", Cancer Research, Dec. 1, 2008, vol. 68, 9 Pages.

Seynhaeve et al., "Tumor Necrosis Factor a Mediates Homogeneous Distribution of Liposomes in Murine Melanoma that Contributes to a Better Tumor Response", Cancer Research, Oct. 1, 2007, vol. 67, No. 19, 9 Pages.

Aghajanian et al., "A Phase I Trial of the Novel Proteasome Inhibitor PS341 in Advanced Solid Tumor Malignancies", Clinical Cancer Research, Aug. 2002, vol. 8, No. 8, retrieved on Apr. 21, 2016 from http://clincancerres.aacrjournals.org/content/8/8/2505.full.pdf, 8 Pages.

Gao et al., "Differential and Antagonistic Effects of v-Jun and c-Jun", Cancer Research, Sep. 15, 1996, vol. 56, No. 18, retrieved on Apr. 21, 2016 from http://cancerres.aacrjournals.org/content/56/18/4229.full.pdf, 8 Pages.

Office Action for the related Japanese Application No. 2016-507620, dated Jan. 26, 2018, 18 pages.

Frommeyer Jr. et al., "Comparison of cyclophosphamide (cytoxan) and uracil mustard (U-8344) in chronic granulocytic leukemia", Published in Cancer, vol. 17, Issue Mar. 3, 1964, pp. 288-296.

Booth et al., "Sarcoma 180 Inhibition by Combinations of 6-Thioguanine and Uracil Mustard", Published in Science Oct. 26, 1962: vol. 138, Issue 3539, pp. 518-519.

Soma et al., "In Vivo Enhanced Antitumor Activity of Carmustine [N,N'-Bis(2-chloroethyl)-N-nitrosourea] by Simvastatin", Publuished in Cancer Research, 1995, vol. 23, pp. 597-602.

Bergenheim et al., "Radiosensitizing effect of estramustine in malignant gliomain vitro andin vivo", Published in Journal of Neuro-Oncology, Oct. 1995, vol. 23, Issue 3, pp. 191-200.

Baraldi et al., "Design, Synthesis, and Biological Activity of Hybrid Compounds between Uramustine and DNA Minor Groove Binder Distamycin A", Published in J.Med. Chem., 2002, vol. 45, pp. 3630-3638.

Ellis et al., "Some Pyrimidines of Biological and Medicinal Interest—Part III", Published in Progress in Medicinal Chemistry, 1971, vol. 8, pp. 61-117.

\* cited by examiner

THERAPEUTIC BENEFIT OF SUBOPTIMALLY ADMINISTERED CHEMICAL COMPOUNDS

CROSS-REFERENCES TO RELATED APPLICATION

This application claims the benefit of U.S. Provisional Application Ser. No. 61/809,627 by Dennis M. Brown, entitled "Compositions and Methods to Improve the Therapeutic Benefit of Suboptimally Administered Chemical Compounds Including Alkylating Agents Such as Uracil Mustard for the Treatment of Immunological, Metabolic, Infectious, and Benign or Malignant Hyperproliferative Disease Conditions" and filed Apr. 8, 2013, the contents of which are incorporated herein in their entirety by this reference.

FIELD OF THE INVENTION

The present invention relates to the general field of treatment of immunological, metabolic, infectious, and benign or neoplastic hyperproliferative disease conditions, including oncology applications, with a focus on novel methods and compositions for the improved utility of chemical agents, compounds, dosage forms limited by suboptimal human therapeutic performance including alkylating agents including uracil mustard (also known as uramustine) and related mustard-based alkylating agents.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infectious diseases, conditions affecting the immune system, metabolic diseases and conditions, and other diseases and conditions.

Since the "War on Cancer" begun in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, as well as other clinical approaches.

The work supported by the NCI and other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other studies remain critical for the discovery and development of any new therapeutic agent.

Unfortunately, many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, cardiotoxicity, gastrointestinal toxicities, or other significant toxicities).

In many cases, after the great time and expense of developing and moving an investigational compound into human clinical trials and where clinical failure has occurred, the tendency has been to return to the laboratory to create a better analog, look for agents with different structures but potentially related mechanisms of action, or undertake other research strategies. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance in many clinical contexts.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, and genetic makeup of the patient, the opportunity for cures in the near term remains elusive. Moreover, the incidence of cancer continues to rise with an approximate 4% increase predicted for 2003 in the United States by the American Cancer Society such that over 1.3 million new cancer cases are estimated. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving the therapeutic benefit of suboptimally administered chemical compounds including alkylating agents such as uracil mustard (uramustine) and related mustard-based alkylating agents.

Relevant literature includes Foye, W. O., "Cancer Chemotherapeutic Agents," American Chemical Society, 1995, and Dorr, R. T., and Von Hoff, D. D., "Cancer Chemotherapy Handbook," Appleton and Lange, 1994.

SUMMARY OF THE INVENTION

This invention relates to novel compositions and methods to improve the utility of chemical agents with suboptimal performance in patients suffering with immunological disease, metabolic disease, infection, or hyperproliferative diseases including cancer. The invention describes novel improvements, pharmaceutical ingredients, dosage forms, excipients, solvents, diluents, drug delivery systems, preservatives, more accurate drug administration, improved dose determination and schedules, toxicity monitoring and amelioration, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches. The invention also relates to the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some case, the use of these suboptimal therapeutics in conjunction with radiation or other conventional chemotherapeutic agents or biotherapeutic agents such as antibodies, vaccines, cytokines, lymphokines, gene and antisense therapies, or other biotherapeutic agents, would provide novel approaches and significant improvement.

In the inventive compositions and methods, the term suboptimal therapy includes agents where Phase I toxicity precluded further human clinical evaluation. It also includes those agents from Phase II trials where limited (<25% response rates) or no significant tumor responses were identified. Also, suboptimal therapy includes those agents, the subject of Phase III clinical trials the outcome of which was either medically or statistically not significant to warrant regulatory submission or approval by government agencies for commercialization or commercialized agents whose clinical performance (i.e. response rates) as a monotherapy are less than 25%, or whose side-effects are severe enough to limit wide utility. Agents with suboptimal clinical activity include but are not limited to the following: mustard-based alkylating agents, including uracil mustard and analogs and derivatives thereof. More specifically, the inventive methods and compositions also focus on improvements for mustard-based alkylating agents, including uracil mustard and analogs and derivatives thereof.

One aspect of the present invention is a method to improve the efficacy and/or reduce the side effects of suboptimally administered drug therapy comprising the steps of:

(1) identifying at least one factor or parameter associated with the efficacy and/or occurrence of side effects of the drug therapy; and (2) modifying the factor or parameter to improve the efficacy and/or reduce the side effects of the drug therapy;

wherein the drug therapy comprises administration of an alkylating agent selected from the group consisting of: (i) a mustard-based alkylating agent; and (ii) an alkylating agent having either: (1) a nitrosourea moiety therein and having one haloalkyl moiety covalently bound to the nitrogen of the nitrosourea moiety not bound to the oxygen; or (2) two haloalkyl moieties bound to a nitrogen atom.

In one alternative, the drug therapy comprises administration of uracil mustard (uramustine). In another alternative, the drug therapy comprises administration of a derivative or analog of uracil mustard. The derivative or analog of uracil mustard can be selected from the group consisting of 6-methyluracil mustard and 6-ethyluracil mustard.

In yet another alternative, the drug therapy comprises administration of a mustard-based alkylating agent selected from the group consisting of:

(1) uracil mustard;
(2) 6-methyluracil mustard;
(3) 6-ethyluracil mustard;
(4) 6-propyluracil mustard;
(5) 3-[1-methyl-4-[1-methyl-4-[1-methyl-4-[N1-[5-bis(2-chloroethyl)amino-2,4-(1H,3H)pyrimidinedione]acetylamino]-pyrrole-2-carboxamido]pyrrole-2-carboxamido]pyrrole-2-carboxamido]propionamidine hydrochloride;
(6) 3-[1-methyl-4-[1-methyl-4-[1-methyl-4-[N1-[5-bis(2-chloroethyl)amino-2,4-(1H,3H)pyrimidinedione]propanoylamino]-pyrrole-2-carboxamido]pyrrole-2-carboxamido]pyrrole-2-carboxamido]propionamidine hydrochloride
(7) 3-[1-methyl-4-[1-methyl-4-[1-methyl-4-[N1-[5-bis(2-chloroethyl)amino-2,4-(1H,3H)pyrimidinedione]butanoylamino]-pyrrole-2-carboxamido]pyrrole-2-carboxamido]pyrrole-2-carboxamido]propionamidine hydrochloride;
(8) 3-[1-methyl-4-[1-methyl-4-[1-methyl-4-[N1-[5-bis(2-chloroethyl)amino-2,4-(1H,3H)pyrimidinedione]pentanoylamino]-pyrrole-2-carboxamido]pyrrole-2-carboxamido]pyrrole-2-carboxamido]propionamidine hydrochloride;
(9) 3-[1-methyl-4-[1-methyl-4-[1-methyl-4-[N1-[5-bis(2-chloroethyl)amino-2,4-(1H,3H)pyrimidinedione]hexanoylamino]-pyrrole-2-carboxamido]pyrrole-2-carboxamido]pyrrole-2-carboxamido]propionamidine hydrochloride;
(10) 3-[1-methyl-4-[1-methyl-4-[1-methyl-4-[N1-[5-bis(2-chloroethyl)amino-2,4-(1H,3H)pyrimidinedione]heptanoylamino]-pyrrole-2-carboxamido]pyrrole-2-carboxamido]pyrrole-2-carboxamido]propionamidine hydrochloride;
(11) estramustine;
(12) derivatives of estramustine;

(13) quinacrine mustard dihydrochloride;
(14) derivatives of quinacrine mustard dihydrochloride;
(15) phosphoramide mustard;
(16) derivatives of phosphoramide mustard;
(17) spiromustine;
(18) derivatives of spiromustine;
(19) mustamine;
(20) derivatives of mustamine;
(21) phenylalanine mustard;
(22) derivatives of phenylalanine mustard;
(23) mannomustine;
(24) derivatives of mannomustine;
(25) 5-((bis(2-chloroethyl)amino)methyl)-pyrimidine-2,4(1H,3H)-dione;
(26) 5-((bis(2-chloroethyl)amino)methyl)-6-methylpyrimidine-2,4(1H,3H)-dione;
(27) 5-((bis(2-chloroethyl)amino)methyl)-1-methylpyrimidine-2,4(1H,3H)-dione;
(28) 5-((bis(2-chloroethyl)amino)methyl)-1,3-dimethylpyrimidine-2,4(1H,3H)-dione;
(29) 5-((bis(2-chloroethyl)amino)methyl)-6-propylpyrimidine-2,4(1H,3H)-dione;
(30) 5-((bis(2-chloroethyl)amino)methyl)-6-methyl-2-thioxo-2,3-dihydropyrimidin-4(1H)-one;
(31) nitrouracil;
(32) 5,6-dihydro-5-nitrouracil;
(33) 5,6-dihydro-5-nitro-1-(4-nitrophenyl)uracil;
(34) 5-nitro-1-(4-nitrophenyl)uracil;
(35) 5,6-dihydro-5-nitro-1(β-D-ribofuranuronic acid ethyl ester)uracil;
(36) 5-nitro-1(β-D-ribofuranuronic acid ethyl ester)uracil;
(37) 5-nitrouracil N-oxide;
(38) prednimustine;
(39) derivatives of prednimustine;
(40) nimustine;
(41) derivatives of nimustine;
(42) ranimustine;
(43) derivatives of ranimustine;
(44) carmustine;
(45) derivatives of carmustine;
(46) lomustine;
(47) derivatives of lomustine;
(48) fotemustine;
(49) derivatives of fotemustine;
(50) ribomustine;
(51) derivatives of ribomustine;
(52) cystemustine;
(53) derivatives of cystemustine;
(54) 4-chlorouracil mustard;
(55) 4-substituted uracil mustard derivatives;
(56) 4-cyanouracil mustard;
(57) 4-nitrouracil mustard;
(58) derivatives of 4-chlorouracil mustard;
(59) derivatives of 4-substituted uracil mustard derivatives;
(60) derivatives of 4-cyanouracil mustard;
(61) derivatives of 4-nitrouracil mustard; and
(62) a derivative or analog of uracil mustard or of alternatives (1)-(61) including one or more optional substituents, provided that the optionally substituted amonafide derivative or analog possesses substantially equivalent pharmacological activity to uracil mustard as determined by DNA alkylation activity;
and the derivatives, active metabolites, bioisosteres, salts, and solvates thereof.

The factor or parameter can be selected from the group consisting of:
(a) dose modification;
(b) route of administration;
(c) schedule of administration;
(d) indications for use;
(e) selection of disease stage;
(f) other indications;
(g) patient selection;
(h) patient/disease phenotype;
(i) patient/disease genotype;
(j) pre/post-treatment preparation
(k) toxicity management;
(l) pharmacokinetic/pharmacodynamic monitoring;
(m) drug combinations;
(n) chemosensitization;
(o) chemopotentiation;
(p) post-treatment patient management;
(q) alternative medicine/therapeutic support;
(r) bulk drug product improvements;
(s) diluent systems;
(t) solvent systems;
(u) excipients;
(v) dosage forms;
(w) dosage kits and packaging;
(x) drug delivery systems;
(y) drug conjugate forms;
(z) compound analogs;
(aa) prodrugs;
(ab) multiple drug systems;
(ac) biotherapeutic enhancement;
(ad) biotherapeutic resistance modulation;
(ae) radiation therapy enhancement;
(af) novel mechanisms of action;
(ag) selective target cell population therapeutics; and
(ah) use with an agent enhancing its activity.

The drug therapy can be administered to treat a hyperproliferative disease, such as cancer; the cancer can be selected from the group consisting of chronic lymphocytic leukemia, follicular lymphoma, lymphocytic lymphoma, chronic myelogenous leukemia, polycythemia vera, ovarian carcinoma, and carcinoma of the lung. Other cancers can also be treated by administration of drug therapy according to the present invention.

Another aspect of the invention is a composition to improve the efficacy and/or reduce the side effects of suboptimally administered drug therapy comprising an alternative selected from the group consisting of:
(i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;
(ii) a composition comprising:
(a) a therapeutically effective quantity of a therapeutic agent, a modified therapeutic agent or a derivative, analog, or prodrug of a therapeutic agent or modified therapeutic agent; and
(b) at least one additional therapeutic agent, therapeutic agent subject to chemosensitization, therapeutic agent subject to chemopotentiation, diluent, excipient, solvent system, drug delivery system, or agent for enhancing the activity or efficacy of the therapeutic agent, the modified therapeutic agent or the derivative, analog, or prodrug of a therapeutic agent or modified therapeutic agent of (a), wherein the composition possesses increased therapeutic efficacy or reduced side effects as compared with an unmodified therapeutic agent;

(iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and (v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent;

wherein the unmodified therapeutic agent is a mustard-based alkylating agent or an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom, the modified therapeutic agent is a modification of a mustard-based alkylating agent or of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom, and the derivative, analog, or prodrug is a derivative, analog, or prodrug of a mustard-based alkylating agent, of a modification of a mustard-based alkylating agent, of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom, or of a modification of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom.

DETAILED DESCRIPTION OF THE INVENTION

This invention relates to novel compositions and methods to improve the utility of chemical agents including uracil mustard or other mustard-based alkylating agents with suboptimal performance for patients with cancer and with other diseases and conditions, including metabolic diseases, immunological diseases, and infectious diseases. The invention describes the novel development of improved pharmaceutical ingredients, dosage forms, excipients, solvents, diluents, drug delivery systems, preservatives, more accurate drug administrations, improved dose determination and schedules, toxicity monitoring and ameliorization, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches, the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some cases, the inventive examples include the use of these sub-optimal therapeutics in conjunction with radiation or other conventional chemotherapeutic agents or biotherapeutic agents such as antibodies, vaccines, cytokines, lymphokines, gene and antisense therapies, or other biotherapeutic agents.

By definition, the term "suboptimal therapy" includes agents where Phase I toxicity precluded further human clinical evaluation. It also includes those agents from Phase II trials where limited or no significant tumor responses were identified. In addition, it also includes those agents, the subject of Phase III clinical trials, whose outcome was either medically or statistically not significant to warrant submission or approval by regulatory agencies for commercialization or commercialized agents whose response rates as a monotherapy are less than 25% or whose side-effects are severe enough to limit wider utility. Agents with suboptimal activity include but are not limited to the following: uracil mustard. More specifically, the inventive methods and compositions also focus on improvements for mustard-based alkylating agents including uracil mustard and analogs and derivatives thereof; other mustard-based alkylating agents, including analogs and derivatives thereof, are described below.

Uracil mustard, also known as uramustine, has the systematic name 5-[bis(2-chloroethyl)amino]-1H-pyrimidine-2,4-dione and the structure of Formula (I), below

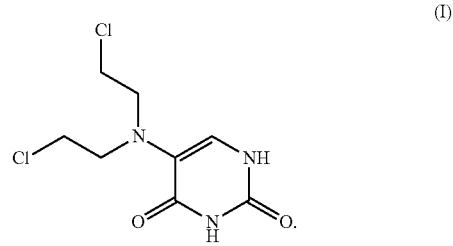 [SMILES: O=c1[nH]cc(N(CCCl)CCCl)c(=O)[nH]1]

Uracil mustard is a polyfunctional alkylating agent that is not cell cycle-specific. The drug binds covalently to DNA to inhibit DNA synthesis and thereby induce cell death (R. T. Dorr & D. D. Von Hoff, "Cancer Chemotherapy Handbook" (2$^{nd}$ ed., 1994, Appleton & Lange), pp. 945, incorporated herein by this reference).

Uracil mustard exhibits a sequence specificity in DNA alkylation unique for nitrogen mustards (W. B. Mattes et al., "DNA Sequence Selectivity of Guanine-N7 Alkylation by Nitrogen Mustards," *Nucl. Acids Res.* 14: 2971-2987 (1986), incorporated herein by this reference). Nitrogen mustards are known to alkylate almost exclusively the guanine $N^7$ position in double-stranded DNA (P. D. Lawley et al., "Interstrand Cross-Linking of DNA by Difunctional Alkylating Agents," *J. Mol. Biol.* 25: 143-160 (1967), incorporated herein by this reference; B. Singer, "The Chemical Effects of Nucleic Acid Alkylation and Their Relation to Mutagenesis and Carcinogenesis," *Prog. Nucl. Acid Res. Mol. Biol.* 15: 219-284 (1975), incorporated herein by this reference) and to preferentially alkylate guanines in oligoguanine sequences (Mattes et al. (1986), supra). This observation has been explained by the influence of nearest neighbor base pairs on the molecular electrostatic potential in the vicinity of guanine-$N^7$ positions in B-DNA (K. W. Kohn et al., "Mechanisms of DNA Sequence Selective Alkylation of Guanine-N7 Positions by Nitrogen Mustards," *Nucl. Acid Res.* 15: 10531-10548 (1987), incorporated herein by this reference; Mattes et al. (1986), supra; A. Pullman & B. Pullman, "Molecular Electrostatic Potential of the Nucleic Acids," *Quart. Rev. Biophys.* 14: 289-380 (1981), incorporated herein by this reference). The sequence specificity of DNA alkylation by uracil mustard exhibits a further detail (5'-YGC-3') which cannot be explained by electrostatics alone. Computer modeling studies have suggested an interaction between the uracil-$O^4$ and the NH of 3'-C as a possible explanation for the observed specificity (Kohn et al. (1987), supra).

The sequence specificity of DNA alkylation by uracil mustard was examined using a novel three-dimensional QSAR method known as HASL, or the hypothetical active site lattice (A. M. Doweyko, "The Hypothetical Active Site Lattice. An Approach to Modelling Active Sites from Data on Inhibitor Molecules," *J. Med. Chem.* 31: 1396-1406 (1988), incorporated herein by this reference). The structures of a variety of tetrameric sequences obtained from the plasmid pBR322 and SV40 were related to their degree of guanine-$N^7$ alkylation by uracil mustard. The resulting correlations were found to point to a significant contribution from bases on the 3'-side of the target guanine nucleotide. The HASL models derived from the analysis of 52 guanine-containing tetramer sequence were used to highlight those atomic features in the favored TGCC sequence that were found most important in determining specificity. It was found that the $NH_2$—O systems present in the two CG base pairs on the 3'-side of the target guanine were significantly correlated to the degree of alkylation by uracil mustard. This finding is consistent with a prealkylation binding event occurring between these sites along the major groove and the uracil mustard $O^2/O^4$ system (A. M. Doweyko & W. B. Mattes, "An Application of 3D-QSAR to the Analysis of the Sequence Specificity of DNA Alkylation by Uracil Mustard," *Biochemistry* 31: 9388-9392 (1992), incorporated herein by this reference).

Uracil mustard can be administered at a dosage of 1 mg/day continuously for greater than three months. Dose-limiting toxicities at high dosages are typically myelosuppression or gastrointestinal effects.

Previously, uracil mustard was considered effective in the palliative treatment of symptomatic chronic lymphocytic leukemia, the palliative treatment of lymphomas of the follicular or lymphocytic type, the palliative treatment of some forms of Hodgkin's disease, and possibly in the palliative treatment of patients with reticulum cell sarcoma, lymphoblastic lymphoma, and mycosis fungoides. Uracil mustard was also considered possibly effective in the palliative treatment of patients with chronic myelogenous leukemia, but was stated to be ineffective in acute blastic crisis or in patients with acute leukemia. Uracil mustard was also stated to be possibly effective in the palliative treatment of early stages of polycythemia vera before the development of leukemia or myelofibrosis. Uracil mustard was also stated to be possibly beneficial in adjunctive treatment of patients with carcinoma of the lung or carcinoma of the ovary.

Uracil mustard has been shown to be active in chronic lymphocytic leukemia (B. J. Kennedy & A. Theologides, "Uracil Mustard, a New Alkylating Agent for Oral Administration in the Management of Patients with Leukemia and Lymphoma," *New Engl. J. Med.* 264: 790-793 (1961), incorporated herein by this reference.) Uracil mustard has been shown to be active in Hodgkin's lymphoma (G. L. Gold et al., "The Use of Mechlorethamine, Cyclophosphamide, and Uracil Mustard in Neoplastic Disease: A Cooperative Study," *J. Clin. Pharmacol.* 10: 110-120 (1970), incorporated herein by this reference). Uracil mustard has also been shown to be active in non-Hodgkin's lymphoma, Hodgkin's lymphoma, and chronic lymphocytic leukemia (B. J. Kennedy et al., "Uracil Mustard Revisited," *Cancer* 85: 2265-2272 (1999), incorporated herein by this reference.

In view of this background, there are a number of potential indications for uracil mustard. As provided below, however, these potential indications are not the only potential indications for uracil mustard and analogs and derivatives thereof.

Chronic lymphocytic leukemia (CLL) is characterized by functionally incompetent lymphocytes. The leukemic lymphocytes have a monoclonal origin. CLL is the most common leukemia in Western countries. There is no standard of care for relapsed disease; nucleoside analogs, alemtuzumab, and bendamustine are used.

Follicular lymphoma is the most common of the indolent lymphomas. In follicular lymphoma, the malignant cells are positive for CD10, CD19, CD20, and CD22. For a second or greater relapse, the standard of care can involve the use of a single agent or combination, transplantation, or radioimmunotherapy.

Mycosis fungoides is an extranodal, indolent disease of T cell origin. It initially involves the skin but ultimately involves lymph nodes, blood, and visceral organs. For relapsed disease, at stage $IVA_1MF$, the standard of care involves systemic therapy with or without skin-directed therapy. For relapsed disease, at stage $IVA_2MF$, the standard of care involves romidepsin, denileukin diftitox, or systemic chemotherapy.

Chronic myelocytic leukemia (CML) is characterized by the uncontrolled proliferation of granulocytes with fairly normal differentiation. It is associated with the fusion of two genes: BCR (on chromosome 22) and ABL1 (on chromosome 9) resulting in a BCL-ABL1 fusion gene. For relapsed disease, the standard of care is second-generation tyrosine kinase inhibitors (TKI).

The cytotoxic potency and antitumor efficacy of nitrogen mustards generally require bifunctionality, which allows the formation of crosslinks in DNA or between DNA and proteins. Nitrogen mustards react with DNA predominantly at the $N^7$-position of guanine forming monoadducts or crosslinks. Crosslinking can occur between two adjacent guanines in the same strand (intrastrand crosslinks), in opposite strands (interstrand crosslinks, ISC), or between DNA and protein (DNA-protein crosslinks, DPC).

Uracil mustard was found to exhibit unusual sequence preferences to alkylate 5'-YGC-3', suggesting that uracil mustard might induce ISC more efficiently than other nitrogen mustards. This specific alkylation preference of uracil mustard for 5'-YGC-3' sites is abolished when a methyl group is added to the $C^6$-position of uracil mustard.

Derivatives of uracil mustard include: (1) 6-methyluracil mustard, described in P. M. O'Connor & K. W. Kohn, "Comparative Pharmacokinetics of DNA Lesion Formation and Removal Following Treatment of L1210 Cells with Nitrogen Mustards," *Cancer Commun.* 2: 387-394 (1990), incorporated herein by this reference, and with the structure of Formula (II), below:

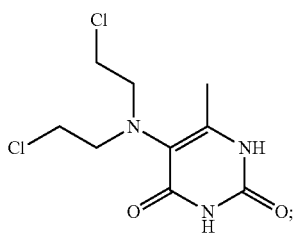

(3) 6-ethyluracil mustard, a homolog of 6-methyluracil mustard with an ethyl group replacing the methyl group at the 6-position of the uracil moiety; and (4) 6-propyluracil mustard, a homolog of 6-methyluracil mustard with a propyl group replacing the methyl group at the 6-position of the uracil moiety; and (5) derivatives of uracil mustard conjugated to the DNA minor groove binder distamycin A, described in P. G. Baraldi et al., "Design, Synthesis, and Biological Activity of Hybrid Compounds Between Uramustine and DNA Minor Groove Binder Distamycin A," *J. Med. Chem.* 45: 3630-3638 (2002), incorporated herein by this reference, and including 3-[1-methyl-4-[1-methyl-4-[1-methyl-4-[N1-[5-bis(2-chloroethyl)amino-2,4-(1H,3H)pyrimidinedione]acetylamino]-pyrrole-2-carboxamido]pyrrole-2-carboxamido]pyrrole-2-carboxamido] propionamidine hydrochloride, 3-[1-methyl-4-[1-methyl-4-[1-methyl-4-[N1-[5-bis(2-chloroethyl)amino-2,4-(1H,3H) pyrimidinedione]propanoylamino]-pyrrole-2-carboxamido] pyrrole-2-carboxamido]pyrrole-2-carboxamido] propionamidine hydrochloride, 3-[1-methyl-4-[1-methyl-4-[1-methyl-4-[N1-[5-bis(2-chloroethyl)amino-2,4-(1H,3H) pyrimidinedione]butanoylamino]-pyrrole-2-carboxamido] pyrrole-2-carboxamido]pyrrole-2-carboxamido] propionamidine hydrochloride, 3-[1-methyl-4-[1-methyl-4-[1-methyl-4-[N1-[5-bis(2-chloroethyl)amino-2,4-(1H,3H) pyrimidinedione]pentanoylamino]-pyrrole-2-carboxamido] pyrrole-2-carboxamido]pyrrole-2-carboxamido] propionamidine hydrochloride, 3-[1-methyl-4-[1-methyl-4-[1-methyl-4-[N1-[5-bis(2-chloroethyl)amino-2,4-(1H,3H) pyrimidinedione]hexanoylamino]-pyrrole-2-carboxamido] pyrrole-2-carboxamido]pyrrole-2-carboxamido] propionamidine hydrochloride, and 3-[1-methyl-4-[1-methyl-4-[1-methyl-4-[N1-[5-bis(2-chloroethyl)amino-2,4-(1H,3H)pyrimidinedione]heptanoylamino]-pyrrole-2-carboxamido]pyrrole-2-carboxamido]pyrrole-2-carboxamido]propionamidine hydrochloride.

Additional mustard-based alkylating agents that are within the scope of the present invention include: (1) estramustine, a derivative of estrogen (specifically, estradiol) with a nitrogen mustard-carbamate ester moiety that makes it an alkylating agent, shown in Formula (III), below, and described in U.S. Pat. No. 3,299,104 to Fex et al., incorporated herein by this reference:

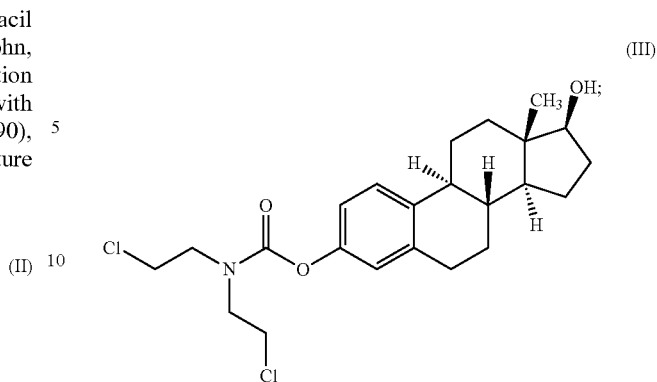

(2) derivatives of estramustine of Formula (IV), wherein each of $R_1$, $R_2$, and $R_3$ are independently selected from the group consisting of hydrogen, lower alkyl, and hydroxy, each of $R_4$, $R_5$, $R_6$, $R_7$, $R_8$, and $R_9$ are independently selected from the group consisting of hydrogen, lower alkyl, and hydroxyl, and each of $X_1$ and $X_2$ are independently selected from the group consisting of chloro, bromo, and iodo; for estramustine itself, each of $R_1$, $R_2$, and $R_3$ is hydrogen, each of $R_4$, $R_5$, $R_6$, $R_7$, $R_8$, and $R_9$ is hydrogen, and each of $X_1$ and $X_2$ is chloro;

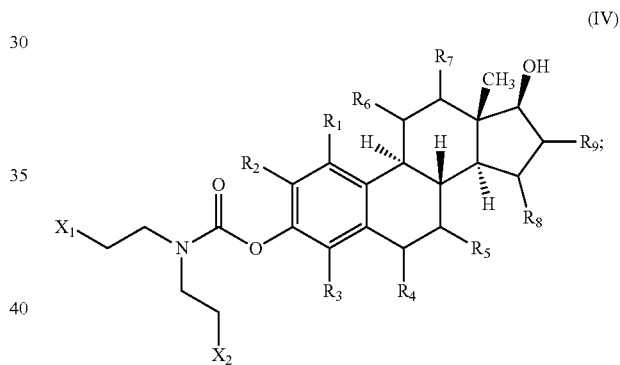

(3) quinacrine mustard dihydrochloride, which has the structure shown below as Formula (V)

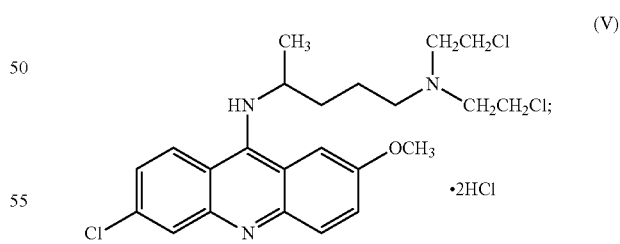

(4) derivatives of quinacrine mustard dihydrochloride of Formula (VI), wherein each of $R_1$, $R_2$, $R_3$, $R_4$, $R_5$, and $R_6$ is independently selected from the group consisting of hydrogen, lower alkyl, and hydroxy, $R_7$ is lower alkyl, $R_8$ is selected from the group consisting of hydrogen and lower alkyl, Q is selected from the group consisting of chloro, bromo, and iodo, and each of $X_1$ and $X_2$ are independently selected from the group consisting of chloro, bromo, and iodo; for quinacrine mustard dihydrochloride itself, each of $R_1$, $R_2$, $R_3$, $R_4$, $R_5$, and $R_6$ is hydrogen, $R_7$ is methyl, $R_8$ is hydrogen, Q is chloro, and each of $X_1$ and $X_2$ is chloro;

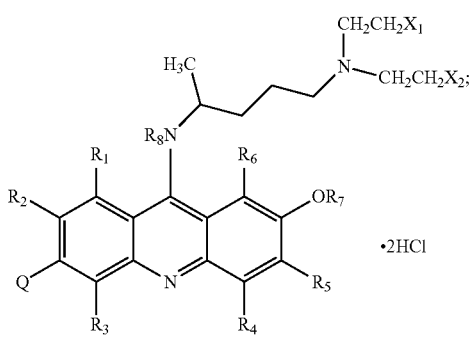

(VI)

·2HCl (5) phosphoramide mustard, which has the structure shown below as Formula (VII)

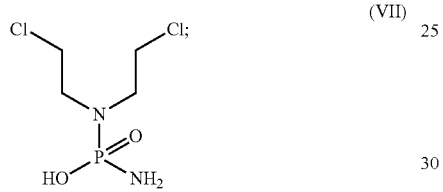

(VII)

(6) derivatives of phosphoramide mustard of Formula (VIII), wherein each of $X_1$ and $X_2$ is selected from the group consisting of chloro, bromo, and iodo;

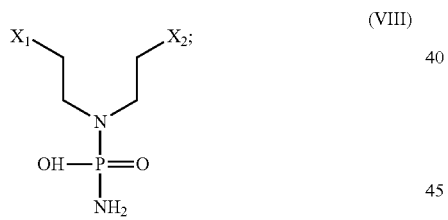

(VIII)

(7) spiromustine, which has the structure shown below as Formula (IX)

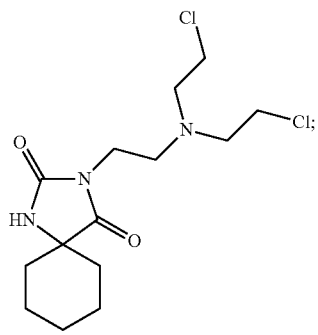

(IX)

(8) analogs of spiromustine of Formula (X), wherein each of $R_1$, $R_2$, $R_3$, $R_4$, and $R_5$ is independently selected from the group consisting of hydrogen, lower alkyl, and hydroxy, and $X_1$ and $X_2$ are each independently selected from the group consisting of chloro, bromo and alkyl. For spiromustine itself, each of $R_1$, $R_2$, $R_3$, $R_4$, and $R_5$ is hydrogen, and each of $X_1$ and $X_2$ is chloro;

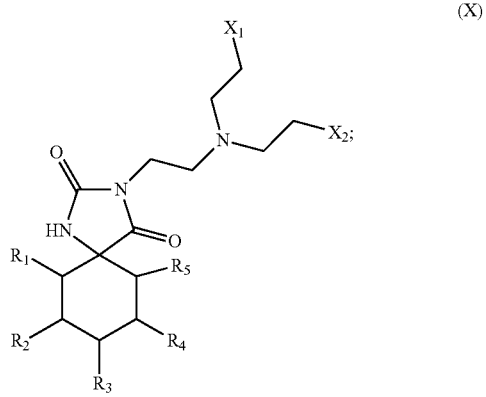

(X)

(9) mustamine (NSC 364989), which has the structure shown below as Formula (XI)

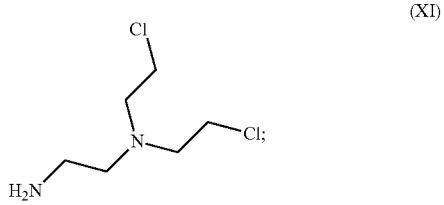

(XI)

(10) analogs of mustamine of Formula (XII), wherein each of $R_1$ and $R_2$ are independently selected from the group consisting of hydrogen and lower alkyl, and each of $X_1$ and $X_2$ are independently selected from the group consisting of chloro, bromo, and iodo; for mustamine itself, each of $R_1$ and $R_2$ is hydrogen and each of $X_1$ and $X_2$ is chloro;

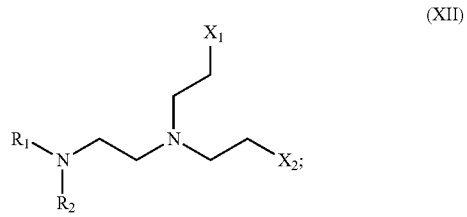

(XII)

(11) phenylalanine mustard (melphalan), which has the structure shown below as Formula (XIII)

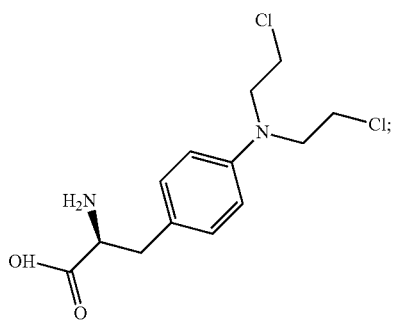

(XIII)

(12) analogs of phenylalanine mustard of Formula (XIV), wherein each of $R_1$, $R_2$, $R_3$, and $R_4$ are independently selected from the group consisting of hydrogen, lower alkyl, and hydroxy, $R_5$ is selected from the group consisting of hydrogen and lower alkyl, each of $R_6$ and $R_7$ are independently selected from the group consisting of hydrogen and lower alkyl, and each of $X_1$ and $X_2$ are independently selected from the group consisting of chloro, bromo, and iodo; for phenylalanine mustard itself, each of $R_1$, $R_2$, $R_3$, and $R_4$ is hydrogen, $R_5$ is hydrogen, each of $R_6$ and $R_7$ is hydrogen, and each of $X_1$ and $X_2$ is chloro;

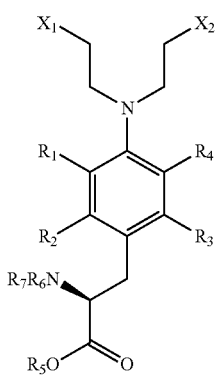

(XIV)

(13) mannomustine, which has the structure shown below as Formula (XV)

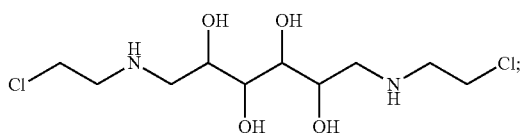

(XV)

(14) analogs of mannomustine of Formula (XVI), wherein each of $R_1$, $R_2$, $R_3$, and $R_4$ are independently selected from the group consisting of hydrogen and lower alkyl and each of $X_1$ and $X_2$ is independently selected from the group consisting of chloro, bromo, and iodo; for mannomustine itself, each of $R_1$, $R_2$, $R_3$, and $R_4$ is hydrogen and each of $X_1$ and $X_2$ is chloro;

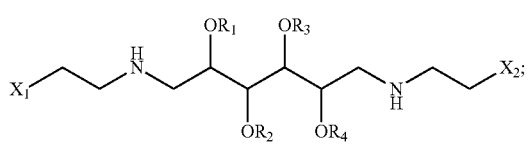

(XVI)

(15) nitrouracil (5-nitrouracil or 2,4-dihydroxy-5-nitropyrimidine), which has the structure shown in Formula (XVII);

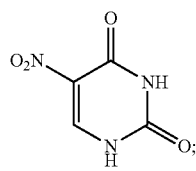

(XVII)

(16) derivatives and analogs of nitrouracil, including products of reduction reactions, including 5,6-dihydro-5-nitrouracil; 5,6-dihydro-5-nitro-1-(4-nitrophenyl)uracil, 5-nitro-1-(4-nitrophenyl)uracil, 5,6-dihydro-5-nitro-1(β-D-ribofuranuronic acid ethyl ester)uracil, and 5-nitro-1(β-D-ribofuranuronic acid ethyl ester)uracil (R. A. Long et al., "Synthesis and Antimicrobial Evaluation of Substituted 5,6-Dihydro-5-Nitrouracils," *J. Med. Chem.* 19: 1072-1074 (1976, incorporated herein by this reference)), and additional pyrimidine derivatives with nitro at the 5-position disclosed in U.S. Pat. No. 8,324,200 to Li et al., incorporated herein by this reference;

(17) 5-nitrouracil N-oxide, which has the structure shown in Formula (XVIII)

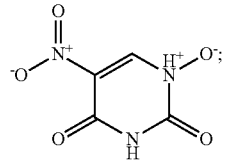

(XVIII)

(18) prednimustine, which has the structure shown in Formula (XIX) (U.S. Pat. No. 8,299,088 to Mateucci et al., incorporated herein by this reference)

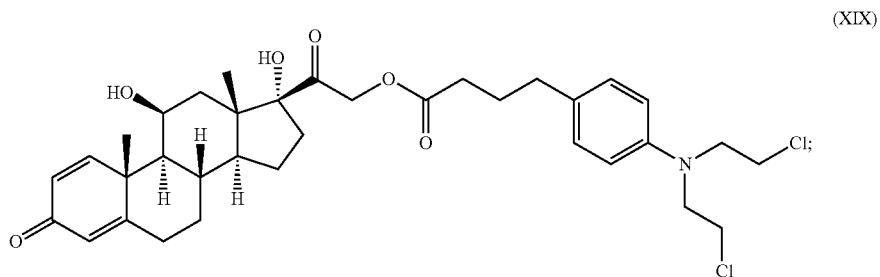

(19) derivatives of prednimustine of Formula (XXII) wherein $R_1$ and $R_2$ are each independently selected from hydrogen and lower alkyl; $R_3$, $R_4$, $R_5$, and $R_6$ are each independently selected from the group consisting of hydrogen, lower alkyl, hydroxy, and lower alkoxy, and $X_1$ and $X_2$ are each independently selected from the group consisting of chloro, bromo, and iodo; in prednimustine itself, $R_1$ and $R_2$ are each hydrogen, $R_3$, $R_4$, $R_5$, and $R_6$ are each hydrogen, and $X_1$ and $X_2$ are each chloro;

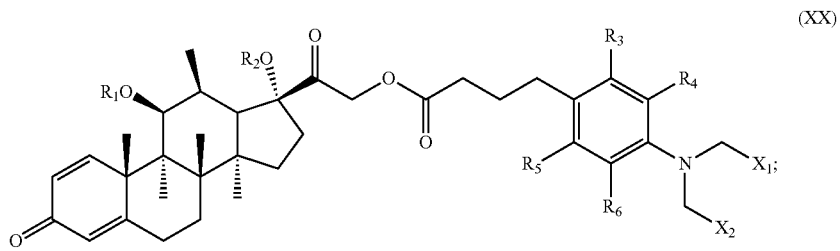

(20) nimustine, which is a nitrosourea alkylating agent having the structure shown in Formula (XXI)

(21) derivatives of nimustine of Formula (XXII) wherein each of $R_1$, $R_2$, and $R_3$ is independently selected from the group consisting of hydrogen and lower alkyl, and X is selected from the group consisting of chloro, bromo, and iodo; for nimustine itself, each of $R_1$, $R_2$, and $R_3$ is hydrogen, and X is chloro;

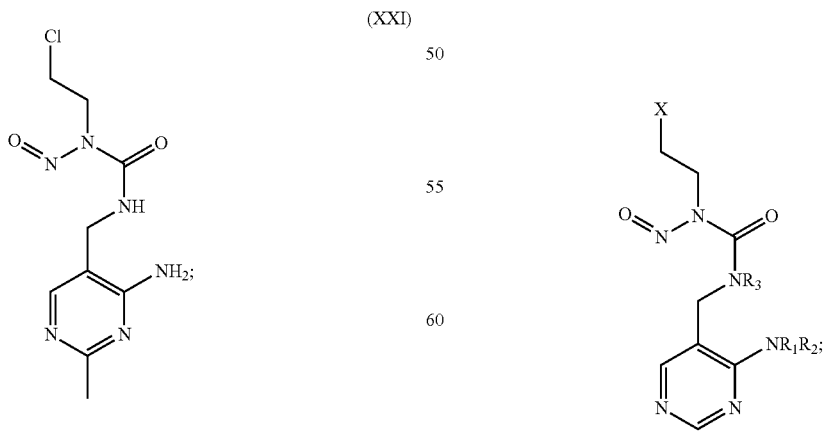

(22) ranimustine, which has the structure of Formula (XXIII)

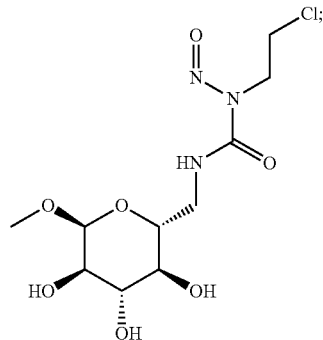
(XXIII)

(23) derivatives of ranimustine of Formula (XXIV) wherein $R_1$ is lower alkyl, each of $R_2$, $R_3$, and $R_4$ is independently selected from the group consisting of hydroxy and lower alkoxy, $R_5$ is selected from the group consisting of hydrogen and lower alkyl, and X is selected from the group consisting of chloro, bromo, and iodo; for ranimustine itself, $R_1$ is methyl, each of $R_2$, $R_3$, and $R_4$ are hydrogen, $R_5$ is hydrogen, and X is chloro;

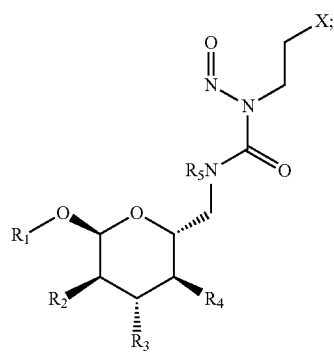
(XXIV)

(24) carmustine, which has the structure of Formula (XXV);

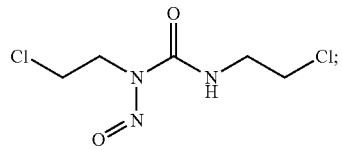
(XXV)

(25) derivatives of carmustine of Formula (XXVI) wherein $R_1$ is selected from the group consisting of hydrogen and lower alkyl, and each of $X_1$ and $X_2$ is independently selected from the group consisting of chloro, bromo, and iodo; in carmustine itself, $R_1$ is hydrogen, and each of $X_1$ and $X_2$ is chloro;

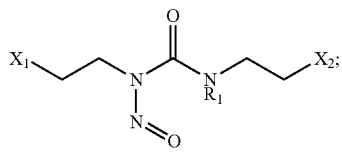
(XXVI)

(26) lomustine, which has the structure of Formula (XXVII);

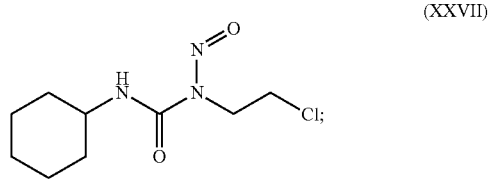 [SMILES: O=NN(CCCl)C(=O)NC1CCCCC1]
(XXVII)

(27) derivatives of lomustine of Formula (XXVIII) wherein $R_1$ is selected from the group consisting of hydrogen and lower alkyl, each of $R_2$, $R_3$, $R_4$, $R_5$, and $R_6$ is independently selected from the group consisting of hydrogen, hydroxy, lower alkyl, and lower alkoxy, and X is selected from the group consisting of chloro, bromo, and iodo; in lomustine itself, $R_1$ is hydrogen, each of $R_2$, $R_3$, $R_4$, $R_5$, and $R_6$ is hydrogen, and X is chloro;

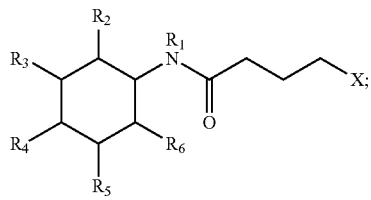
(XXVIII)

(28) fotemustine, which exists in two stereoisomers and is typically administered as the RS racemic mixture, has the structure (showing both enantiomers) of Formula (XXIX);

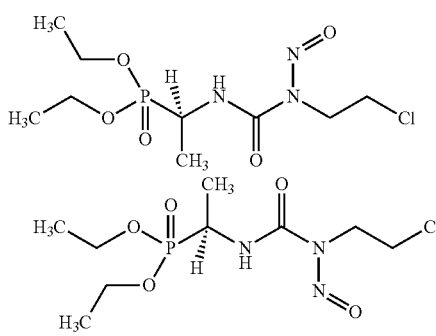
(XXIX)

(29) derivatives of fotemustine having the structure of Formula (XXX) (for each enantiomer; both enantiomers are shown in Formula (XXX)) wherein $R_1$ is selected from the group consisting of hydrogen and lower alkyl; and X is selected from the group consisting of chloro, bromo, and iodo; in fotemustine, $R_1$ is hydrogen and X is chloro;

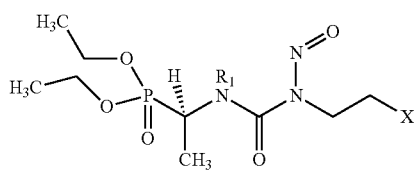

(XXX)

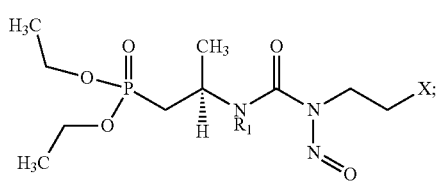

(30) ribomustine, which has the structure of Formula (XXXI);

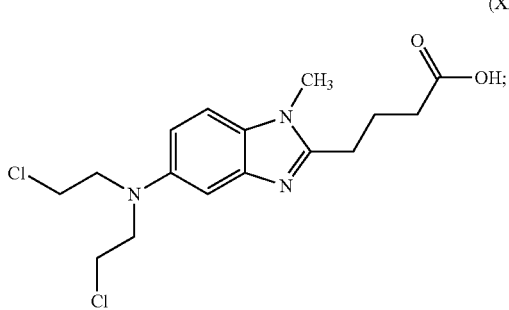

(XXXI)

(31) derivatives of ribomustine of formula (XXXII) wherein $R_1$ is selected from the group consisting of hydrogen and lower alkyl, and each of $X_1$ and $X_2$ is independently selected from the group consisting of chloro, bromo, and iodo; in ribomustine itself, $R_1$ is hydrogen and each of $X_1$ and $X_2$ is chloro;

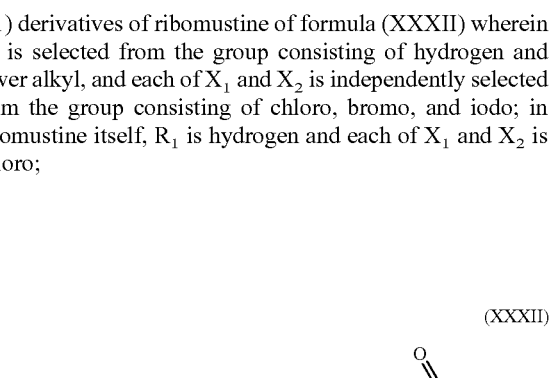

(XXXII)

(32) cystemustine (N'-(2-chloroethyl)-N-(2-(methylsulfonyl)-ethyl)-N'-nitrosourea) which has the structure of Formula (XXXIII);

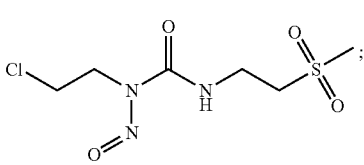

(XXXIII)

(33) derivatives of cystemustine of the structure of Formula (XXXIV) wherein $R_1$ is selected from the group consisting of hydrogen and lower alkyl, and X is selected from the group consisting of chloro, bromo, and iodo. For cystemustine itself, $R_1$ is hydrogen and X is chloro;

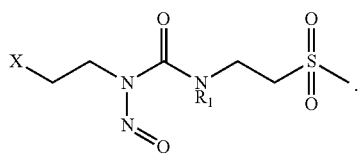

(XXXIV)

Still additional mustard-based alkylating agents that are within the scope of the present invention are the compounds disclosed in S. Fabrissin et al., "Synthesis and Anticancer Activity of 5-Diethylaminoethyl Derivatives and Nitrogen Mustards of Uracil and 2-Thiouracils," *J. Med. Chem.* 19: 639-642 (1976), incorporated herein by this reference. These compounds are the compounds of Formula (XXXV), Formula (XXXVI), Formula (XXXVII), Formula (XXXVIII), Formula (XXXIX), and Formula (XL), below:

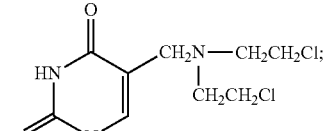

(XXXV)

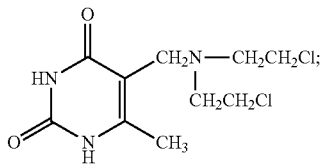

(XXXVI)

(XXXVII)

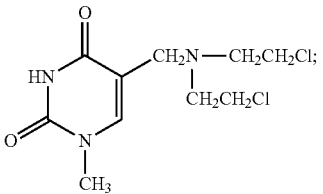

(XXXVIII)

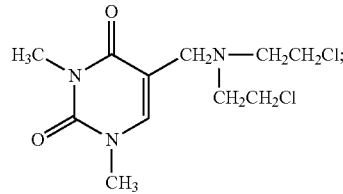

-continued

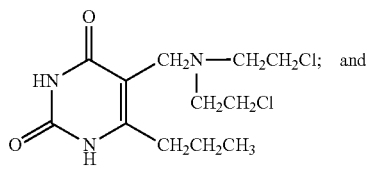

(XXXIX)

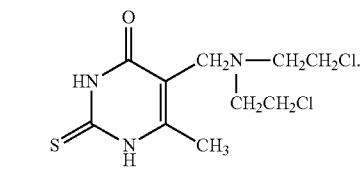

(XL)

The compound of Formula (XXXV) is 5-((bis(2-chloroethyl)amino)methyl)-pyrimidine-2,4(1H,3H)-dione; the compound of Formula (XXXVI) is 5-((bis(2-chloroethyl)amino)methyl)-6-methylpyrimidine-2,4(1H,3H)-dione; the compound of Formula (XXXVII) is 5-((bis(2-chloroethyl)amino)methyl)-1-methylpyrimidine-2,4(1H,3H)-dione; the compound of Formula (XXXVIII) is 5-((bis(2-chloroethyl)amino)methyl)-1,3-dimethylpyrimidine-2,4(1H,3H)-dione; the compound of Formula (XXXIX) is 5-((bis(2-chloroethyl)amino)methyl)-6-propylpyrimidine-2,4(1H,3H)-dione; and the compound of Formula (XL) is 5-((bis(2-chloroethyl)amino)methyl)-6-methyl-2-thioxo-2,3-dihydropyrimidin-4(1H)-one.

Still other alkylating agents that are within the scope of the present invention include alkylating agents having either: (1) a nitrosourea moiety therein and having one haloalkyl moiety covalently bound to the nitrogen of the nitrosourea group not bound to the oxygen; or (2) two haloalkyl moieties bound to a nitrogen atom.

Additional mustard-based alkylating agents include 4-chlorouracil mustard, 4-substituted uracil mustard, 4-cyanouracil mustard, and 4-nitrouracil mustard. These compounds are described further below.

The synthesis of 4-chlorouracil mustard is shown in Reaction Scheme A, shown below.

Reaction Scheme A

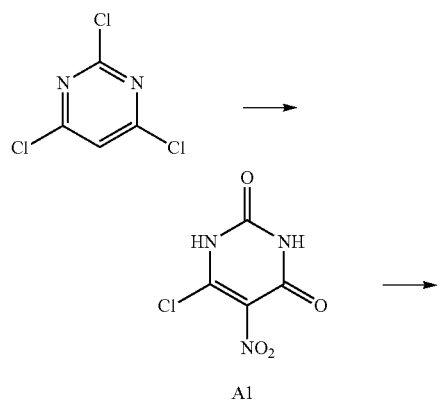

A1

-continued

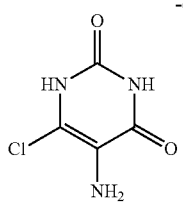

A2

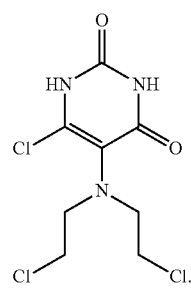

P1

In Reaction Scheme A, the starting material is 2,4,6-trichloropyrimidine. The starting material 2,4,6-trichloropyrimidine is transformed into 4-chloro-5-nitrouracil (A1) (R. M. Cresswell & H. C. S. Wood, *J. Chem. Soc.* 4768-4775 (1960), incorporated herein by this reference). Reduction of the nitro group can be accomplished by reaction with sodium dithionite to give product A2 (A. Talukdar et al., *Bioorg. Med. Chem.* 18: 3518-3534 (2010), incorporated herein by this reference). Chloroethylation of the amino group of product A2 can then be achieved by using the procedure described in United States Patent Application 2011/0190509 by Chen et al., incorporated herein by this reference, to produce 4-chlorouracil mustard (Formula (XLI))

(XLI)

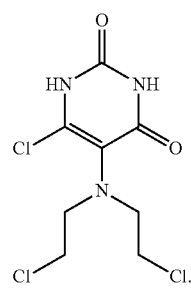

The synthesis of 4-substituted uracil mustards is shown in Reaction Scheme B, shown below.

Reaction Scheme B

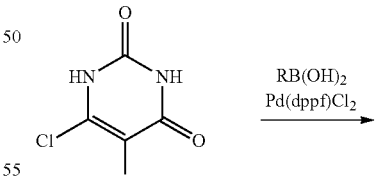

A1

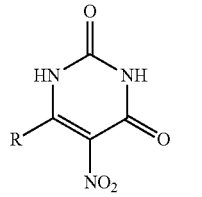

A3

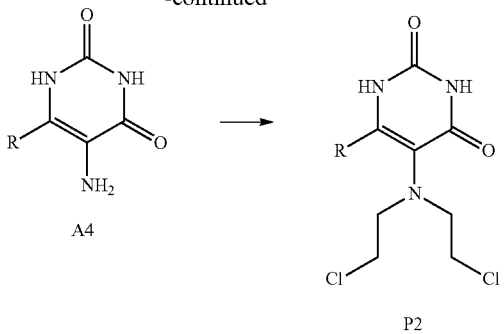

A4 → P2

In Reaction Scheme B, 4-chloro-5-nitrouracil (A1) can undergo Suzuki coupling (N. Miyaura & A. Suzuki, Chem. Rev. 95: 2457-2483 (1995), incorporated herein by this reference), to yield compounds of formula A3, wherein R is selected from the group consisting of aryl, heteroaryl, alkenyl, alkynyl, alkyl, hydroxyaryl, hydroxyheteroaryl, hydroxyalkenyl, hydroxyalkynyl, hydroxyalkyl, haloaryl, haloheteroaryl, haloalkenyl, haloalkynyl, and haloalkyl, which can themselves be further optionally substituted. In general, for optional substitutions on aryl or heteroaryl groups, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino ($NR^1R^2$), nitro, —SR, —S(O)R, —S(O$_2$)R, —S(O$_2$)NR$^1$R$^2$, and —CONR$^1$R$^2$. In general, for optional substitutions on alkyl, alkenyl, and alkynyl groups, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino (NR$^1$R$^2$), nitro, —SR, —S(O)R, —S(O$_2$)R, —S(O$_2$)NR$^1$R$^2$, and —CONR$^1$R$^2$. Further descriptions of potential optional substituents are provided below. Reduction of the nitro group of A3 can be accomplished by reaction with sodium dithionite to give product A4 (A. Talukdar et al., Bioorg. Med. Chem. 18: 3518-3534 (2010), incorporated herein by this reference). Chloroethylation of product A4 can then be accomplished by using the procedure outlined in U.S. Pat. No. 2,969,364 to Lyttle to give 4-substituted uracil mustard (P2 in Reaction Scheme B).

The 4-substituted uracil mustard has the structure shown in Formula (XLII)

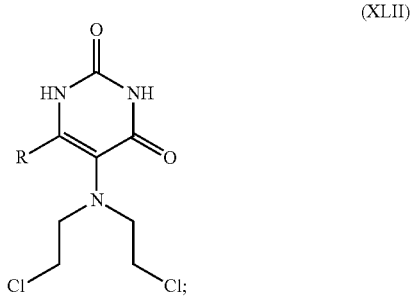

(XLII)

wherein R is selected from the group consisting of aryl, heteroaryl, alkenyl, alkynyl, alkyl, hydroxyaryl, hydroxyheteroaryl, hydroxyalkenyl, hydroxyalkynyl, hydroxyalkyl, haloaryl, haloheteroaryl, haloalkenyl, haloalkynyl, and haloalkyl.

As described above, and as detailed more generally below, derivatives and analogs of uracil mustard can be optionally substituted with one or more groups that do not substantially affect the pharmacological activity of the derivative or analog. These groups are generally known in the art. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicyclic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Aromatic rings have a delocalized π-electron system containing 4n+2π electrons, where n is an integer. Aromatic rings can be formed from 5, 6, 8, 9, or more than 9 atoms. Aromatics can be optionally substituted. Unless further limited, the term "aromatic" includes both carbocyclic aryl (e.g., phenyl) and heterocyclic aryl ("heteroaryl") groups (e.g., pyridine). Unless further limited, the term also includes both monocyclic and fused-ring polycyclic groups (i.e., rings that share adjacent pairs of carbon atoms). Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxyheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the suffix "ene" appended to a group indicates that such a group is a diradical. For example, and not by way of limitation, a methylene is a diradical of a methyl group and has the structure —$CH_2$—, and an ethylene is a diradical of an ethyl group and has the structure —$CH_2CH_2$—.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valiences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, =S⁻, —$NZ^cZ^c$, =$NZ^b$, =N—$OZ^b$, trihalomethyl, —$CF_3$, —CN, —OCN, —SCN, —NO, —$NO_2$, =$N_2$, —$N_3$, —$S(O)_2Z^b$, —$S(O)_2NZ^b$, —$S(O_2)O^-$, —$S(O_2)OZ^b$, —$OS(O_2)OZ^b$, —$OS(O_2)O^-$, —$OS(O_2)OZ^b$, —$P(O)(O^-)_2$, —$P(O)(OZ^b)$ $(O^-)_2$, —$P(O)(OZ^b)(OZ^b)$, —$C(O)Z^b$, —$C(S)Z^b$, —$C(NZ^b)$ $Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)Z^b$, —$NZ^bC(S)Z^b$, —$NZ^bC(O)O^-$, —$NZ^bC(O)Oz^b$, —$NZ^bC(S)OZ^b$, —$NZ^bC$ $(O)NZ^cZ^c$, —$NZ^bC(NZ^b)Z^b$, —$NZ^bC(NZ^b)NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —$NZ^cZ^c$ is meant to include —$NH_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-$C(O)OZ^b$, -alkylene-$C(O)NZ^bZ^b$, and —$CH_2$—$CH_2$—$C(O)$—$CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$N_3$, —$S(O)_2Z^b$, —$S(O_2)O^-$, —$S(O_2)OZ^b$, —$OS(O_2)OZ^b$, —$OS(O_2)O^-$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)O^-$, —$C(O)$ $OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)$ $OZ^b$, —$NZ^bC(O)OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$S(O)_2Z^b$, —$S(O_2)O^-$, —$S(O_2)OZ^b$, —$OS(O_2)OZ^b$, —$OS(O_2)O^-$, —$P(O)(O)_2$, —$P(O)(OZ^b)(O^-)$, —$P(O)(OZ^b)(OZ^b)$, —$C(O)Z^b$, —$C(S)$ $Z^b$, —$C(NZ^b)Z^b$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)OZ^b$, —$OC(S)OZ^b$, —$NZ^bO(O)Z^b$, —$NZ^bC(S)Z^b$, —$NZ^bC(O)$ $OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted olefin isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolyzable esters of the present compounds are the compounds whose carboxyls are present in the form of hydrolyzable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the "hetero" terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S, more typically from N, O, and S.

As used herein, the term "alkanoyl" refers to an alkyl group covalently linked to a carbonyl (C=O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)($Alk_3$), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —S(O)$_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is CH$_3$CH$_2$OC(O)—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

The synthesis of 4-cyanouracil mustard is shown in Reaction Scheme C, shown below.

In Reaction Scheme C, 4-cyano-5-nitrouracil can be synthesized by a palladium-catalyzed reaction with Zn(CN)$_2$ and Pd(PPh$_3$)$_4$ as described in A. Anbarasan et al., *Chem. Soc. Rev.* 40: 5049-5067 (2011), incorporated herein by this reference, to give product A5 in Reaction Scheme C. Reduction of the nitro group in product A5 with sodium dithionite (A. Talukdar et al., *Bioorg. Med. Chem.* 18: 3518-3534 (2010), incorporated herein by this reference) affords product A6. Chloroethylation of the amino group in product A6 can then be accomplished by using the procedure outlined in U.S. Pat. No. 2,969,364 to give 4-cyanouracil mustard (P3 in Reaction Scheme C).

The structure of 4-cyanouracil mustard is shown in Formula (XLIII)

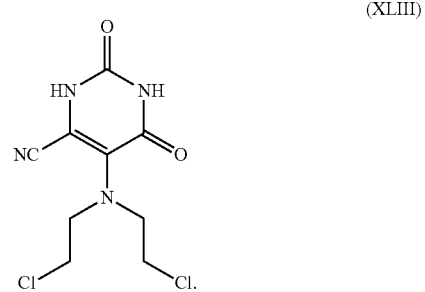 [SMILES: N#Cc1[nH]c(=O)[nH]c(=O)c1N(CCCl)CCCl]

Finally, the synthesis of 4-nitrouracil mustard is shown in Reaction Scheme D.

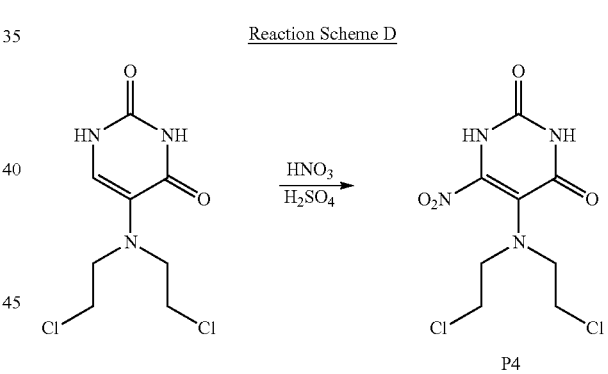

In Reaction Scheme D, 4-nitrouracil mustard (P4) is prepared by nitration of uracil mustard according to the procedure described in M. A. Zajac et al., *Synth. Commun.* 33: 3291-3297 (2003), incorporated herein by this reference. To prepare 4-nitrouracil mustard, to solid uracil mustard (10 mmol) at 0° C. is slowly added concentrated sulfuric acid (20 mL). The mixture is then warmed to room temperature, and stirred for 30 min. The mixture is then recooled to 0° C. and fuming nitric acid (5 mL) is slowly added. The mixture is gradually warmed to room temperature, and stirred at room temperature for 2 hours. The mixture is then poured into ice (100 g), and stirred for 30 min. The precipitate is then collected via filtration and dried under high vacuum to afford 4-nitrouracil mustard.

The structure of 4-nitrouracil mustard is shown in Formula (XLIV).

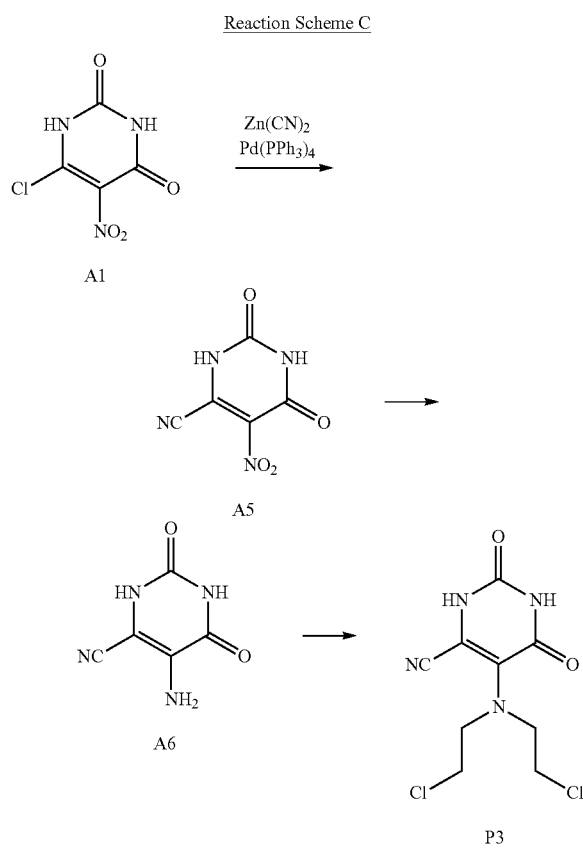

(XLIV)

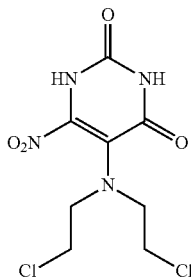

In addition, mustard-based alkylating agents that are within the scope of the present invention include derivatives of 4-chlorouracil mustard, 4-substituted uracil mustard, 4-cyanouracil mustard, and 4-nitrouracil mustard, shown in Formulas (XLV), (XLVI), (XLVII), and (XLVIII), below. In the derivatives of Formulas (XLV), (XLVI), (XLVII), and (XLVIII), $X_1$ and $X_2$ are each independently selected from the group consisting of chloro, bromo, and iodo, and $Q_1$ and $Q_2$ are each selected from the group consisting of hydrogen and lower alkyl.

(XLV)

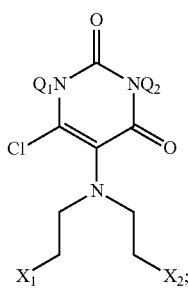

(XLVI)

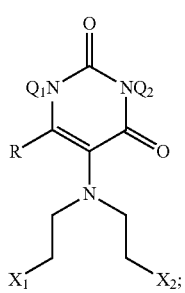

(XLVII)

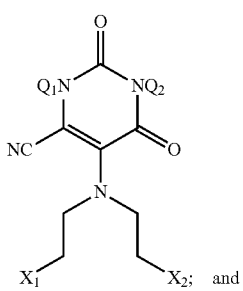
and (XLVIII)

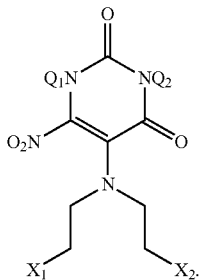

Other mustard-based alkylating agents that are within the scope of the present invention are known in the art and can be used in methods and compositions according to the present invention as described below.

Accordingly, the following mustard-based alkylating agents are within the scope of the present invention:
(1) uracil mustard;
(2) 6-methyluracil mustard;
(3) 6-ethyluracil mustard;
(4) 6-propyluracil mustard;
(5) 3-[1-methyl-4-[1-methyl-4-[1-methyl-4-[N1-[5-bis(2-chloroethyl)amino-2,4-(1H,3H)pyrimidinedione]acetylamino]-pyrrole-2-carboxamido]pyrrole-2-carboxamido]pyrrole-2-carboxamido]propionamidine hydrochloride;
(6) 3-[1-methyl-4-[1-methyl-4-[1-methyl-4-[N1-[5-bis(2-chloroethyl)amino-2,4-(1H,3H)pyrimidinedione]propanoylamino]-pyrrole-2-carboxamido]pyrrole-2-carboxamido]pyrrole-2-carboxamido]propionamidine hydrochloride
(7) 3-[1-methyl-4-[1-methyl-4-[1-methyl-4-[N1-[5-bis(2-chloroethyl)amino-2,4-(1H,3H)pyrimidinedione]butanoylamino]-pyrrole-2-carboxamido]pyrrole-2-carboxamido]pyrrole-2-carboxamido]propionamidine hydrochloride;
(8) 3-[1-methyl-4-[1-methyl-4-[1-methyl-4-[N1-[5-bis(2-chloroethyl)amino-2,4-(1H,3H)pyrimidinedione]pentanoylamino]-pyrrole-2-carboxamido]pyrrole-2-carboxamido]pyrrole-2-carboxamido]propionamidine hydrochloride;
(9) 3-[1-methyl-4-[1-methyl-4-[1-methyl-4-[N1-[5-bis(2-chloroethyl)amino-2,4-(1H,3H)pyrimidinedione]hexanoylamino]-pyrrole-2-carboxamido]pyrrole-2-carboxamido]pyrrole-2-carboxamido]propionamidine hydrochloride;
(10) 3-[1-methyl-4-[1-methyl-4-[1-methyl-4-[N1-[5-bis(2-chloroethyl)amino-2,4-(1H,3H)pyrimidinedione]heptanoylamino]-pyrrole-2-carboxamido]pyrrole-2-carboxamido]pyrrole-2-carboxamido]propionamidine hydrochloride;
(11) estramustine;
(12) derivatives of estramustine;
(13) quinacrine mustard dihydrochloride;
(14) derivatives of quinacrine mustard dihydrochloride;
(15) phosphoramide mustard;
(16) derivatives of phosphoramide mustard;
(17) spiromustine;
(18) derivatives of spiromustine;
(19) mustamine;
(20) derivatives of mustamine;
(21) phenylalanine mustard;
(22) derivatives of phenylalanine mustard;
(23) mannomustine;
(24) derivatives of mannomustine;

(25) 5-((bis(2-chloroethyl)amino)methyl)-pyrimidine-2,4(1H,3H)-dione;
(26) 5-((bis(2-chloroethyl)amino)methyl)-6-methylpyrimidine-2,4(1H,3H)-dione;
(27) 5-((bis(2-chloroethyl)amino)methyl)-1-methylpyrimidine-2,4(1H,3H)-dione;
(28) 5-((bis(2-chloroethyl)amino)methyl)-1,3-dimethylpyrimidine-2,4(1H,3H)-dione;
(29) 5-((bis(2-chloroethyl)amino)methyl)-6-propylpyrimidine-2,4(1H,3H)-dione;
(30) 5-((bis(2-chloroethyl)amino)methyl)-6-methyl-2-thioxo-2,3-dihydropyrimidin-4(1H)-one;
(31) nitrouracil;
(32) 5,6-dihydro-5-nitrouracil;
(33) 5,6-dihydro-5-nitro-1-(4-nitrophenyl)uracil;
(34) 5-nitro-1-(4-nitrophenyl)uracil;
(35) 5,6-dihydro-5-nitro-1(β-D-ribofuranuronic acid ethyl ester)uracil;
(36) 5-nitro-1(β-D-ribofuranuronic acid ethyl ester)uracil;
(37) 5-nitrouracil N-oxide;
(38) prednimustine;
(39) derivatives of prednimustine;
(40) nimustine;
(41) derivatives of nimustine;
(42) ranimustine;
(43) derivatives of ranimustine;
(44) carmustine;
(45) derivatives of carmustine;
(46) lomustine;
(47) derivatives of lomustine;
(48) fotemustine;
(49) derivatives of fotemustine;
(50) ribomustine;
(51) derivatives of ribomustine;
(52) cystemustine;
(53) derivatives of cystemustine;
(54) 4-chlorouracil mustard;
(55) 4-substituted uracil mustard derivatives;
(56) 4-cyanouracil mustard;
(57) 4-nitrouracil mustard;
(58) derivatives of 4-chlorouracil mustard;
(59) derivatives of 4-substituted uracil mustard derivatives;
(60) derivatives of 4-cyanouracil mustard;
(61) derivatives of 4-nitrouracil mustard; and
(62) a derivative or analog of uracil mustard or of alternatives (1)-(61) including one or more optional substituents, provided that the optionally substituted amonafide derivative or analog possesses substantially equivalent pharmacological activity to uracil mustard as determined by DNA alkylation activity;
and the derivatives, active metabolites, bioisosteres, salts, and solvates thereof.

Still other derivatives or analogs of uracil mustard, including conjugates with other therapeutically active agents, are within the scope of the invention.

(I) Suboptimal Therapeutics

In general, examples of compounds with suboptimal therapeutic activity may include antimetabolites, DNA/nucleic acid binding/reactive agents, topoisomerase inhibitors, anti-tubulin agents, signal transduction inhibitors, protein synthesis inhibitors, inhibitors of DNA transcribing enzymes, DNA/RNA intercalating agents, DNA minor groove binders, drugs that block steroid hormone action, photochemically active agents, immune modifying agents, hypoxia selective cytotoxins, chemical radiation sensitizers and protectors, antisense nucleic acids, oligonucleotide and polynucleotide therapeutic agents, immune modifying agents, antitumor antibiotics, and other classes of therapeutic agents having antineoplastic, antiproliferative, or immune-system-modulating activity. Specific examples include: fluoropyrimidines, thiopurines, inhibitors of nucleoside diphosphate reductase, 2'-deoxyribonucleoside analogs, nucleosides, folic acid analogs, methotrexate, 6-diazo-5-oxo-norleucine, L-asparaginase, N-(phosphoacetyl)-L-aspartic acid, nitrogen mustard, mechlorethamine, chlorambucil, melphalan, cyclophosphamide, estramustine, platinum complexes, nitrosoureas, BCNU, CCNU, streptozotocin, alkyl sulfonates, busulfan, clomesone, triazenylimidazoles and related triazenes, mitozolomide, temozolomide, aziridines, tris(1-aziridinyl)phosphine sulfide, aziridinylphosphines, 3,6-diaziridinyl-2,5-bis(carboethoxyamino)-1,4-benzoquinone (Diaziquone) (AZQ), AZQ analogs, procarbazine, hexamethylamine, topoisomerase I inhibitors, camptothecin, camptothecin analogs, topoisomerase II inhibitors, anthracyclines, doxorubicin, epirubicin, etoposide, DNA intercalating agents, amsacrine, CI-921, 1'-carbamate analogs of amsacrine, 9-aminoacridine-4-carboxamides, acridine carboxamide, tricyclic carboxamides, 1-nitroacridine, acridine derivatives, diacridines, triacridines, podophyllotoxins, ellipticine, merbarone, benzisoquinolinediones, etoposide, teniposide, aminoanthraquinones, inhibitors of DNA-transcribing enzymes, transcription inhibitors, replication inhibitors, RNA replication inhibitors, polymerase inhibitors, rifamycins, actinomycins, DNA minor groove binding compounds, Hoechst 33258, mitomycins, CC-1065, mithramycins, chloromycins, olivomycins, phthalanilides, anthramycins, antimitotic agents, vinca alkaloids, vinblastine and analogs, vincristine and analogs, navelbine, colchicine and analogs, bleomycin and analogs, estramustine, aromatase inhibitors, tamoxifen, LHRH antagonists and analogs, porfimer, hematoporphyrins, electron-affinic oxygen mimetics, nitoaromatics, nitroheterocyclics, nitroimidizaoles, tirapazamine, mitomycins, menadione and analogs, napthoquinones, aziridoquinones, amine oxides, N-oxides, metal complexes, bioreductive agents, bioreductive alkylating agents, metal complexes, radiation sensitizers, radiation protectors, antisense agents, antigene agents, transcription factor inhibitors, ODN complexes, ribozymes, double stranded RNA, antitumor antibiotics, acivicin, aclararubicin, acodazole, acronycine, adozelesin, alanosine, allopurinol, altretamine, aminoglutethimide, amonafide, amsacrine, androgens, anguidine, aphidicolin glycinate, asaley, 5-azacitidine, azathioprine, Baker's Antifol, β-2'-deoxythioguanosine, bisantrene HCl, bleomycin sulfate, busulfan, buthionine sulfoximine (BSO), BWA 773U82, BW 502U83 HCl, BW 7U85 mesylate, caracemide, carbetimer, carboplatin, carmustine, chlorambucil, chloroquinoxaline sulfonamide, chlorozotocin, chromomycin A3, cisplatin, cladribine, carboplatin, oxaliplatin, rhodamine compounds, corticosteroids, CPT-11, cristanol, cyclocytidine, cyclophosphamide, cytarabine, cytembena, dabis maleate, dacarbazine, dactinomycin, daunorubicin HCl, deazauridine, dexrazoxane, dianhydrogalactitol (DAG), diaziquone (AZQ), dibromodulcitol, didemnin B, diethyldithiocarbamate, diglycoaldehyde, dihydro-5-azacytidine, doxorubicin, echinomycin, edatrexate, edelfosine, eflornithine, elsamitrucin, epirubicin, esorubicin, estramustine phosphate, estrogens, etanidazole, ethiofos, etoposide, fadrazole, fazarabine, fenretinide, finasteride, flavone acetic acid, floxuridine, fludarabine phosphate, 5-fluorouracil, flutamide, gallium nitrate, gemcitabine, goserelin acetate, hepsulfam, hexamethylene bisacetamide, amonafide, hydrazine sulfate, 4-hydroxyandrostenedione, hydroxyurea, idarubicin HCl, ifosfamide, 4-ipomeanol, iproplatin, isotretinoin, leuproloide acetate, levamisole, liposomal daunorubicin, liposomal doxorubicin, lomustine, lonidamine, maytansine, mechloethamine hydrochloride, melphalan, menogaril, 6-mercaptopurine, mesna, methotrexate, N-methylformamide, mifepristone, mitoguazone, mitomycin C, mitotane, mitoxantrone hydrochloride, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, plicamycin, porfimer sodium, predimustine, procarbazine, progestins, pyrazofurin, razoxane, sargramostim, semustine, spirogermanium, streptonigrin, streptozocin, sulofenur, suramin sodium, tamoxifen, taxotere, tegafur, teniposide, terephthalamidine, teroxirone, thioguanine, thiotepa, thymidine, tiazofurin, topotecan, tormifene, treinoin, trifluoroperazine hydrochloride, trifluridine, trimetrexate, uracil mustard, vinblastine sulfate, vincristine sulfate, vindesine, vinorelbine, vinzolidine, Yoshi 864, zorubicin, 2-Cl-2'-deoxyadenosine, 3-deazauridine, 4-nitroestrone, 6-methylmercaptopurine riboside, 9-aminocamotothecin, nitrocamptothecin, irinotecan, CPT-11, acivicin, acodazole HCl, ADR-529, ICRF-187, amasacrine, aminothiadiazole, ADTA, antibiotic FR901228, aphidicolin glycinate, azacytidine, AZT, bizelesin, brefeldins, wortmannins, cantharidins, bromodeoxyuridines, bryostatin, BSO, CAI, caracemide, chlorosulfaquinoxaline, sulfonamide, clomesone, cyclocytidine HCl, cyclodisone, cyclopentenylcytosine, deoxyspergualin, DHAC, diaziquone, didemnin B, dideoxy-β-fluorouracil, dideoxyadenosine, dideoxyinosine, dihydrotriazine benzene sulfonyl fluoride, dolastatin 10, ecteinascidin 743, etanidazole, ethiofos (WR-2721), fazarabine, flavone acetic acid, flavopiridol, fludarabine phosphate, fostriecin, genistein, hepsulfam, HMBA, amonafide, hydrazine sulfate, iododeoxyuridine, ipomeanol, KNI-272, leucovorin calcium, levamisole, menogaril, merbarone, methotrexate, misonidazole, mitoguazone, mitoxantrone HCl, mitozolomide, N-methylformamide, O6-benzylguanine, PALA, pancratistatin, penclomedine, pentamethylmelamine HCl, pentamidine isethionate, pentostatin, perillyl alcohol, phyllanthoside, pibenzimole HCl, piroxantrone, pyrazine diazohydroxide, pyrazoloacridine, quinocarmycins, rebeccamycins, rhizoxin, semustine (methyl CCNU), suramin sodium, Taxol, terephthalamidine, teroxirone, thioguanine, thymidine, tiazofurin, TMCA, topotecan, 5-fluorouracil, methotrexate, cyclophosphamide, ras inhibitors, farnesylation inhibitors, bromodeoxyuridine, tetracycline compounds, arsenic trioxide, combretastatins, 2-methoxyestradiol, thalidomide and analogs, cephalotaxine derivatives, gleevec, stributyrin, triciribine phosphate, trimetrexate, UCN-01, 7-hydroxystaurosporine, uridine, lycurium, ritrosulfan, artemisinin, artesunate, lonidamine, mesna, bromomannitol, hydrazine sulfate, pipobroman, phenesterin, pyrazine diazohydroxide, cytembena, spirogermanium, terephthalamidine, bufalin, gemcitabine, FMDC, colchicine, thiocolchicine, colchicine analogs, LHRH analogs, paclitaxel, MGBG, meisoindigo, indirubin analogs, metformin, phlorizin, and other compounds, including homoharringtonine (HHT).

In particular, the present invention is directed to mustard-based alkylating agents. In one particularly preferred embodiment, the mustard-based alkylating agent is uracil mustard (uramustine). In another alternative, the mustard-based alkylating agent is selected from the group consisting of:

(1) uracil mustard;
(2) 6-methyluracil mustard;
(3) 6-ethyluracil mustard;
(4) 6-propyluracil mustard;
(5) 3-[1-methyl-4-[1-methyl-4-[1-methyl-4-[N1-[5-bis(2-chloroethyl)amino-2,4-(1H,3H)pyrimidinedione]acetylamino]-pyrrole-2-carboxamido]pyrrole-2-carboxamido]pyrrole-2-carboxamido]propionamidine hydrochloride;
(6) 3-[1-methyl-4-[1-methyl-4-[1-methyl-4-[N1-[5-bis(2-chloroethyl)amino-2,4-(1H,3H)pyrimidinedione]propanoylamino]-pyrrole-2-carboxamido]pyrrole-2-carboxamido]pyrrole-2-carboxamido]propionamidine hydrochloride
(7) 3-[1-methyl-4-[1-methyl-4-[1-methyl-4-[N1-[5-bis(2-chloroethyl)amino-2,4-(1H,3H)pyrimidinedione]butanoylamino]-pyrrole-2-carboxamido]pyrrole-2-carboxamido]pyrrole-2-carboxamido]propionamidine hydrochloride;
(8) 3-[1-methyl-4-[1-methyl-4-[1-methyl-4-[N1-[5-bis(2-chloroethyl)amino-2,4-(1H,3H)pyrimidinedione]pentanoylamino]-pyrrole-2-carboxamido]pyrrole-2-carboxamido]pyrrole-2-carboxamido]propionamidine hydrochloride;
(9) 3-[1-methyl-4-[1-methyl-4-[1-methyl-4-[N1-[5-bis(2-chloroethyl)amino-2,4-(1H,3H)pyrimidinedione]hexanoylamino]-pyrrole-2-carboxamido]pyrrole-2-carboxamido]pyrrole-2-carboxamido]propionamidine hydrochloride;
(10) 3-[1-methyl-4-[1-methyl-4-[1-methyl-4-[N1-[5-bis(2-chloroethyl)amino-2,4-(1H,3H)pyrimidinedione]heptanoylamino]-pyrrole-2-carboxamido]pyrrole-2-carboxamido]pyrrole-2-carboxamido]propionamidine hydrochloride;
(11) estramustine;
(12) derivatives of estramustine;
(13) quinacrine mustard dihydrochloride;
(14) derivatives of quinacrine mustard dihydrochloride;
(15) phosphoramide mustard;
(16) derivatives of phosphoramide mustard;
(17) spiromustine;
(18) derivatives of spiromustine;
(19) mustamine;
(20) derivatives of mustamine;
(21) phenylalanine mustard;
(22) derivatives of phenylalanine mustard;
(23) mannomustine;
(24) derivatives of mannomustine;
(25) 5-((bis(2-chloroethyl)amino)methyl)-pyrimidine-2,4 (1H,3H)-dione;
(26) 5-((bis(2-chloroethyl)amino)methyl)-6-methylpyrimidine-2,4(1H,3H)-dione;
(27) 5-((bis(2-chloroethyl)amino)methyl)-1-methylpyrimidine-2,4(1H,3H)-dione;
(28) 5-((bis(2-chloroethyl)amino)methyl)-1,3-dimethylpyrimidine-2,4(1H,3H)-dione;
(29) 5-((bis(2-chloroethyl)amino)methyl)-6-propylpyrimidine-2,4(1H,3H)-dione;
(30) 5-((bis(2-chloroethyl)amino)methyl)-6-methyl-2-thioxo-2,3-dihydropyrimidin-4(1H)-one;
(31) nitrouracil;
(32) 5,6-dihydro-5-nitrouracil;
(33) 5,6-dihydro-5-nitro-1-(4-nitrophenyl)uracil;
(34) 5-nitro-1-(4-nitrophenyl)uracil;
(35) 5,6-dihydro-5-nitro-1(β-D-ribofuranuronic acid ethyl ester)uracil;
(36) 5-nitro-1(β-D-ribofuranuronic acid ethyl ester)uracil;
(37) 5-nitrouracil N-oxide;
(38) prednimustine;
(39) derivatives of prednimustine;
(40) nimustine;
(41) derivatives of nimustine;

(42) ranimustine;
(43) derivatives of ranimustine;
(44) carmustine;
(45) derivatives of carmustine;
(46) lomustine;
(47) derivatives of lomustine;
(48) fotemustine;
(49) derivatives of fotemustine;
(50) ribomustine;
(51) derivatives of ribomustine;
(52) cystemustine;
(53) derivatives of cystemustine;
(54) 4-chlorouracil mustard;
(55) 4-substituted uracil mustard derivatives;
(56) 4-cyanouracil mustard;
(57) 4-nitrouracil mustard;
(58) derivatives of 4-chlorouracil mustard;
(59) derivatives of 4-substituted uracil mustard derivatives;
(60) derivatives of 4-cyanouracil mustard;
(61) derivatives of 4-nitrouracil mustard;
(62) a derivative or analog of uracil mustard or of alternatives (1)-(61) including one or more optional substituents, provided that the optionally substituted amonafide derivative or analog possesses substantially equivalent pharmacological activity to uracil mustard as determined by DNA alkylation activity;
and the derivatives, active metabolites, bioisosteres, salts, and solvates thereof (referred to herein as "Alternatives (1)-(62)").

DNA alkylation activity can be determined by methods known in the art and described, for example, in S. D. Mertins et al., "In Vitro Evaluation of Dimethane Sulfonate Analogues with Potential Alkylating Activity and Selective Renal Cell Carcinoma Toxicity," *Mol. Cancer Ther.* 3: 849-860 (2004), incorporated herein by this reference.

In still another alternative, the therapeutic agent is an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom.

One aspect of the present invention is a method to improve the efficacy and/or reduce the side effects of suboptimally administered drug therapy comprising the steps of:
  (1) identifying at least one factor or parameter associated with the efficacy and/or occurrence of side effects of the drug therapy; and
  (2) modifying the factor or parameter to improve the efficacy and/or reduce the side effects of the drug therapy;
wherein the drug therapy comprises administration of a mustard-based alkylating agent.

The factor or parameter can be selected from the group consisting of:
  (1) dose modification;
  (2) route of administration;
  (3) schedule of administration;
  (4) indications for use;
  (5) selection of disease stage;
  (6) other indications;
  (7) patient selection;
  (8) patient/disease phenotype;
  (9) patient/disease genotype;
  (10) pre/post-treatment preparation;
  (11) toxicity management;
  (12) pharmacokinetic/pharmacodynamic monitoring;
  (13) drug combinations;
  (14) chemosensitization;
  (15) chemopotentiation;
  (16) post-treatment patient management;
  (17) alternative medicine/therapeutic support;
  (18) bulk drug product improvements;
  (19) diluent systems;
  (20) solvent systems;
  (21) excipients;
  (22) dosage forms;
  (23) dosage kits and packaging;
  (24) drug delivery systems;
  (25) drug conjugate forms;
  (26) compound analogs;
  (27) prodrugs;
  (28) multiple drug systems;
  (29) biotherapeutic enhancement;
  (30) biotherapeutic resistance modulation;
  (31) radiation therapy enhancement;
  (32) novel mechanisms of action;
  (33) selective target cell population therapeutics; and
  (34) use with an agent to enhance its activity.

II. Dose Modification

Improvements for suboptimal chemotherapeutics including substituted alkylating agents such as uracil mustard are made by alterations to the time that the compound is administered, the use of dose-modifying agents that control the rate of metabolism of the compound, normal tissue protective agents, or other alterations. General examples include: variations of infusion schedules (e.g., bolus i.v. versus continuous infusion), the use of lymphokines (e.g., G-CSF, GM-CSF, EPO) to increase leukocyte count for improved immune response or to prevent anemia caused by myelosuppressive agents, rescue agents such as leucovorin for 5-FU or thiosulfate for cisplatin treatment. Specific inventive examples for substituted alkylating agents such as uracil mustard include: continuous i.v. infusion for hours to days; biweekly administration; doses greater than 5 mg/m$^2$/day; progressive escalation of dosing from 1 mg/m$^2$/day based on patient tolerance; doses less than 1 mg/m$^2$ for greater than 14 days; use of caffeine to modulate metabolism; use of isoniazid to modulate metabolism; selected and intermittent boost dose administrations; bolus single and multiple doses of 1-5 mg/m$^2$; oral dosing including multiple daily dosing; micro-dosing; immediate release dosing; slow release dosing; controlled release dosing; dosages of 0.15 mg/kg; dosages of 0.30 mg/kg; dosages of 0.45 mg/kg; dosages of 0.60 mg/kg; doses above 0.15 mg/kg/wk to 1 mg/kg/wk; doses above 1 mg/day to 4 mg/day; or doses above 2 mg/kg every 2 weeks to 1 mg/kg for three days per week.

III. Route of Administration

Improvements for suboptimal chemotherapeutics including substituted alkylating agents such as uracil mustard are made by alterations in the route that the compound is administered. General examples include: changing route from oral to intravenous administration and vice versa or the use of specialized routes such as subcutaneous, intramuscular, intraarterial, intraperitoneal, intralesional, intralymphatic, intratumoral, intrathecal, oral dosing including immediate and controlled release, intravesicular, intracranial. Specific inventive examples for substituted alkylating agents such as uracil mustard include: topical administration; intravesicular administration for bladder cancer; oral administration; slow release oral delivery; intrathecal administration; intraarterial administration; continuous infusion; or intermittent infusion.

IV. Schedule of Administration

Improvements for suboptimal chemotherapeutics including substituted alkylating agents such as uracil mustard are made by alterations to the time that the compound is administered. General examples include: changing from a monthly administration to a weekly or daily dosing or variations of the schedule. Specific inventive examples for substituted alkylating agents such as uracil mustard include: daily administration; weekly administration; weekly administration for three weeks; weekly administration for two weeks; biweekly administration; biweekly administration for three weeks with a 1-2 week rest period; intermittent boost dose administration; or administration daily for one week then once per week for multiple weeks.

V. Indications for Use

Improvements for suboptimal chemotherapeutics including substituted alkylating agents such as uracil mustard are made by alterations in the types of disease, clinical stage of disease that the compound is administered. General examples include: the use of solid tumor agents for leukemias and vice versa, the use of antitumor agents for the treatment of benign hyperproliferative disease such as psoriasis or benign prostate hypertrophy, metabolic diseases, immunological diseases or infection. Specific inventive examples for substituted alkylating agents such as uracil mustard include: use for the treatment of leukemias; use for the treatment of myelodysplastic syndrome; use for the treatment of angiogenic diseases; use for the treatment of benign prostate hypertrophy; use for the treatment of psoriasis; use for the treatment of gout; use for the treatment of autoimmune conditions; use for the prevention of transplantation rejection; use for restenosis prevention in cardiovascular disease; use for the treatment of mycosis fungoides; use in bone marrow transplantation; use as an anti-infective agent; use in treatment for AIDS; use in treatment for lymphoma generally; use in treatment for occurrence of a blast crisis in chronic myelocytic leukemia (CML); use in treatment for cutaneous T-cell lymphoma; use in treatment for reticulum cell sarcoma; use in treatment for large cell lymphoma; use in treatment for lung cancer characterized by overexpression of EGFR; use in treatment for ovarian cancer characterized by resistance to topoisomerase I inhibitors; and use in treatment for cancers characterized by resistance to platinum-containing chemotherapeutic agents, such as ovarian cancer and lung cancer.

VI. Disease Stages

Improvements for suboptimal chemotherapeutics including substituted alkylating agents such as uracil mustard are made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for substituted alkylating agents such as uracil mustard include: use for the treatment of localized polyp stage colon cancer; use for treatment of leukoplakia in the oral cavity; use to induce angiogenesis inhibition to prevent or limit metastatic spread; use against chronic myelogenous leukemia (CML) either together with tyrosine kinase inhibitors such as imatinib or homoharringtonine or subsequent to administration of tyrosine kinase inhibitors such as imatinib or homoharringtonine; use against lymphoma either together with rituximab or bendamustine or subsequent to administration of rituximab or bendamustine; or use against chronic lymphocytic leukemia either together with rituximab or bendamustine or subsequent to administration of rituximab or bendamustine.

VII. Other Indications

Improvements for suboptimal chemotherapeutics including substituted alkylating agents such as uracil mustard are made by using the compound for non-malignant diseases and conditions. General examples include: premalignant conditions, benign hyperproliferative conditions, treatment of infections, treatment of parasites, usage to relieve pain, control of pleural effusions. Specific inventive examples for substituted alkylating agents such as uracil mustard include: use as an anti-infective agent; use as an antiviral agent; use as an antibacterial agent; use for control of pleural effusions; use as an antifungal agent; use as an antiparasitic agent; use for treatment of eczema; use for treatment of shingles; use for treatment of condylomata; use as an anti-human papilloma virus (HPV) agent; use against HIV with AZT, DDI, or reverse transcriptase inhibitors; or use as an anti-herpes simplex virus (HPV) agent.

VIII. Patient Selection

Improvements for suboptimal chemotherapeutics including substituted alkylating agents such as uracil mustard are made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other disease conditions that may uniquely exploit a feature of the compound. Specific inventive examples for substituted alkylating agents such as uracil mustard include: patients with disease conditions with high levels of metabolic enzymes such as histone deacetylase, protein kinases, ornithine decarboxylase; patients with disease conditions with low levels of metabolic enzymes such as histone deacetylase, protein kinases, or ornithine decarboxylase; patients with low or high susceptibility to thrombocytopenia or neutropenia; patients intolerant of GI toxicities; patients characterized by over- or under-expression of jun, GPCRs, signal transduction proteins, VEGF, prostate specific genes, protein kinases, or telomerase; patients failing to respond to or refractory to inhibitors of Bruton's tyrosine kinase (BTK), such as ibrutinib; patients with hepatic impairment who are not candidates for BTK inhibitors; patients with hepatic impairment who are not candidates for chlorambucil, cyclophosphamide, or bendamustine; or patients intolerant to, not a candidate for, or refractory to anti-CD20 antibodies.

IX. Patient/Disease Phenotype

Improvements for suboptimal chemotherapeutics including substituted alkylating agents such as uracil mustard are made by more precise identification of a patient's ability to tolerate, metabolize and exploit the use of the compound. General examples include: use of diagnostic tools and kits to better characterize a patient's ability to process/metabolize a chemotherapeutic agent or the susceptibility of the patient to toxicity caused by potential specialized cellular, metabolic, or organ system phenotypes. Specific inventive examples for substituted alkylating agents such as uracil mustard include: use of a diagnostic tool, a diagnostic technique, a diagnostic kit, or a diagnostic assay to confirm a patient's particular phenotype; use of a method for measurement of a marker selected from the group consisting of histone deacetylase, ornithine decarboxylase, VEGF, a protein that is a gene product of a prostate specific gene, a protein that is a gene product of jun, a protein kinase, desmoglein-3, and a caspase-derived neo-epitope; surrogate compound dosing; or low dose pre-testing for enzymatic status.

X. Patient/Disease Genotype

Improvements for suboptimal chemotherapeutics including substituted alkylating agents such as uracil mustard are made by testing and analyzing a patient's genotype for unique features that may be of value to predict efficacy, toxicity, metabolism, or other factors related to the response to the substituted alkylating agent or to metabolites of the substituted alkylating agent. General examples include: biopsy samples of tumors or normal tissues (e.g., white blood cells) may also be taken and analyzed to specifically tailor or monitor the use of a particular drug against a gene target, unique tumor gene expression pattern, or a SNP (single nucleotide polymorphism) or pattern of SNPs, to enhance efficacy or to avoid particular drug-sensitive normal tissue toxicities. Specific inventive examples for substituted alkylating agents such as uracil mustard include: diagnostic tools, techniques, kits and assays to confirm a patient's particular genotype; gene/protein expression chips and analysis; Single Nucleotide Polymorphisms (SNPs) assessment; SNPs for histone deacetylase ornithine decarboxylase, GPCR's, protein kinases, telomerase, jun; or identification and measurement of metabolism enzymes and metabolites.

XI. Pre/Post-Treatment Preparation

Improvements for suboptimal chemotherapeutics including substituted alkylating agents such as uracil mustard are made by specialized preparation of a patient prior to or after the use of a chemotherapeutic agent. General examples include: induction or inhibition of metabolizing enzymes, specific protection of sensitive normal tissues or organ systems. Specific inventive examples for substituted alkylating agents such as uracil mustard include: the use of colchicine or analogs; use of diuretics; use of uricosuric agents such as probenecid; use of uricase; non-oral use of nicotinamide; use of sustained release forms of nicotinamide; use of inhibitors of polyADP ribose polymerase; use of caffeine; leucovorin rescue; infection control; or use of antihypertensives.

XII. Toxicity Management

Improvements for suboptimal chemotherapeutics including substituted alkylating agents such as uracil mustard are made by use of additional drugs or procedures to prevent or reduce potential side effects or toxicities. General examples include: the use of anti-emetics, anti-nausea, hematological support agents to limit or prevent neutropenia, anemia, or thrombocytopenia, vitamins, antidepressants, treatments for sexual dysfunction, or other agents or methods to reduce potential side effects or toxicities. Specific inventive examples for substituted alkylating agents such as uracil mustard include: the use of colchicine or analogs; use of uricosurics such as probenecid; the use of diuretics; the use of uricase; the non-oral use of nicotinamide; the use of sustained release forms of nicotinamide; the use of inhibitors of poly ADP-ribose polymerase; the use of caffeine; leucovorin rescue; the use of sustained release allopurinol; the use of non-oral use of allopurinol; the administration of bone marrow transplant stimulants, blood, platelet infusions, Neupogen, G-CSF, or GM-CSF; pain management; the administration of anti-inflammatories; the administration of fluids; the administration of corticosteroids; the administration of insulin control medications; the administration of antipyretics; the administration of anti-nausea treatments; the use of anti-diarrheal treatment; the administration of N-acetylcysteine; the administration of antihistamines; the administration of agents for reduction of gastric toxicity; or the administration of agents to reduce myelosuppression.

XIII. Pharmacokinetic/Pharmacodynamic Monitoring

Improvements for suboptimal chemotherapeutics including substituted alkylating agents such as uracil mustard are made by the use of monitoring drug levels after dosing in an effort to maximize a patient's drug plasma level, to monitor the generation of toxic metabolites, monitoring of ancillary medicines that could be beneficial or harmful in terms of drug-drug interactions. General examples include: the monitoring of drug plasma protein binding, the monitoring of specific metabolites or breakdown products, or other products of biotransformation. Specific inventive examples for substituted alkylating agents such as uracil mustard include: multiple determinations of drug plasma levels; or multiple determinations of metabolites in the blood or urine.

XIV. Drug Combinations

Improvements for suboptimal chemotherapeutics including substituted alkylating agents such as uracil mustard are made by exploiting unique drug combinations that may provide a more than additive or synergistic improvement in efficacy or side-effect management. General examples include: alkylating agents with anti-metabolites, topoisomerase inhibitors with antitubulin agents. Specific inventive examples for substituted alkylating agents such as uracil mustard include: use with topoisomerase inhibitors; use with fraudulent nucleosides; use with fraudulent nucleotides; use with thymidylate synthetase inhibitors; use with signal transduction inhibitors; use with cisplatin or platinum analogs; use with alkylating agents; use with anti-tubulin agents; use with antimetabolites; use with berberine; use with apigenin; use with colchicine and analogs; use with genistein; use with etoposide; use with cytarabine; use with camptothecins; use with vinca alkaloids; use with 5-fluorouracil; use with curcumin; use with NF-κB inhibitors; use with rosmarinic acid; use with mitoguazone, use with meisoindigo; use with imatinib; use with dastanib; use with nilotinib; use with epigenetic modulators; use with transcription factor inhibitors; use with taxol; use with homoharringtonine; use with pyridoxal; use with spirogermanium; use with caffeine; use with nicotinamide; use with methylglyoxalbisguanylhydrazone; use with Rho kinase inhibitors; use with 1,2,4-benzotriazine oxides; use with an alkylglycerol; use with an inhibitor of a Mer, Ax1, or Tyro-3 receptor kinase; use with an inhibitor of ATR kinase; use with a modulator of Fms kinase, Kit kinase, MAP4K4 kinase, TrkA kinase, or TrkB kinase; use with endoxifen; use with a mTOR inhibitor; use with an inhibitor of Mnk1a kinase, Mkn1 b kinase, Mnk2a kinase, or Mnk2b kinase; use with a modulator of pyruvate kinase M2; use with a modulator of phosphoinositide 3-kinases; use with a cysteine protease inhibitor; use with phenformin; use with Sindbis virus-based vectors; use with peptidomimetics that act as mimetics of Smac and inhibit IAPs to promote apoptosis; use with a Raf kinase inhibitor; use with a nuclear transport modulator; use with an acid ceramidase inhibitor and a choline kinase inhibitor; use with tyrosine kinase inhibitors; use with anti-CS1 antibodies; use with inhibitors of protein kinase CK2; use with anti-guanylyl cyclase C (GCC) antibodies; use with histone deacetylase inhibitors; use with cannabinoids; use with glucagon-like peptide-1 (GLP-1) receptor agonists; use with inhibitors of Bcl-2 or Bcl-xL; use with Stat3 pathway inhibitors; use with inhibitors of polo-like kinase 1 (Plk1); use with GBPAR1 activators; use with modulators of serine-threonine protein kinase and poly(ADP-ribose) polymerase (PARP) activity; use with taxanes; use with inhibitors of dihydrofolate reductase; use with inhibitors of aromatase; use with benzimidazole-based anti-neoplastic agents; use with an O6-methylguanine-DNA-methyltransferase (MGMT) inhibitor; use with CCR9 inhibitors; use with acid sphingomyelinase inhibitors; use with peptidomimetic macrocycles; use with cholanic acid amides; use with substituted oxazaphosphorines; use with anti-TWEAK receptor antibodies; use with an ErbB3 binding protein; use with a glutathione S-transferase-activated anti-neoplastic compound; use with substituted phosphorodiamidates; use with inhibitors of MEKK protein kinase; use with COX-2 inhibitors; use with cimetidine and a cysteine derivative; use with anti-IL-6 receptor antibody; use with an antioxidant; use with an isoxazole inhibitor of tubulin polymerization; use with PARP inhibitors; use with Aurora protein kinase inhibitors; use with peptides binding to prostate-specific membrane antigen; use with CD19 binding agents; use with benzodiazepines; use with Toll-like receptor (TLR) agonists; use with bridged bicyclic sulfamides; use with inhibitors of epidermal growth factor receptor kinase; use with a ribonuclease of the T2 family having actin-binding activity; use with myrsinoic acid A or an analog thereof; use with inhibitors of a cyclin-dependent kinase; use with inhibitors of the interaction between p53 and MDM2; use with inhibitors of the receptor tyrosine kinase MET; use with largazole or largazole analogs; use with inhibitors of AKT protein kinase; use with 2'-fluoro-5-methyl-β-L-arabinofuranosyluridine or L-deoxythymidine; use with HSP90 modulators; use with inhibitors of JAK kinases, especially JAK-2; use with inhibitors of PDK1 protein kinase; use with PDE4 inhibitors; use with inhibitors of proto-oncogene c-Met tyrosine kinase; use with inhibitors of indoleamine 2,3-dioxygenase; use with agents that inhibit expression of ATDC (TRIM29); use with proteomimetic inhibitors of the interaction of nuclear receptor with coactivator peptides; use with antagonists of XIAP family proteins; use with tumor-targeted superantigens; use with inhibitors of Pim kinases; use with inhibitors of CHK1 or CH2 kinases; use with inhibitors of angiopoietin-like 4 protein; use with Smo antagonists; use with nicotinic acetylcholine receptor antagonists; use with farnesyl protein transferase inhibitors; use with adenosine A3 receptor antagonists; use with Bruton's tyrosine kinase (BTK) inhibitors; use with FLT-3 inhibitors; use with cancer vaccines; use with biologics; use with anti-nausea therapies; use with cyclophosphamide; use with doxorubicin; use with vincristine (including liposomal formulations); use with prednisone (including delayed release formulations); use with bleomycin; use with dacarbazine; use with bendamustine hydrochloride; use with alemtuzumab; use with ofatumumab; use with obinutuzumab; use with rituximab; use with lenalidomide; use with pomalidomide; use with aprenilast; use with vorinostat; use with pralatrexate; use with panobinostat; use with brentuximab vedotin; use with fludarabine; use with stem cell therapies; use with cyclin-dependent kinase inhibitors such as substituted pyrazolo[1,5-a]pyrimidines; use with 4-(4-methylpiperazin-1-ylmethyl)-N-[4-methyl-3-(4-pyridin-3-yl)pyrimidin-2-ylamino)phenyl]-benzamide; use with CXCR4 inhibitors; or use with tryptamicidin. In the case of vaccines, biologics, BTK inhibitors, JAK-2 inhibitors, or FLT-3 inhibitors, the substituted alkylating agent can be administered either simultaneously with the vaccine, biologic, BTK inhibitor, JAK-2 inhibitor, or FLT-3 inhibitor or subsequent to the administration of the vaccine, biologic, BTK inhibitor, JAK-2 inhibitor, or FLT-3 inhibitor.

XV. Chemosensitization

Improvements for suboptimal chemotherapeutics including substituted alkylating agents such as uracil mustard are made by exploiting them as chemosensitizers where no measurable activity is observed when used alone but in combination with other therapeutics a more than additive or synergistic improvement in efficacy is observed. General examples include: misonidazole with alkylating agents, tirapazamine with cisplatin. Specific inventive examples for substituted alkylating agents such as uracil mustard include: as a chemosensitizer in combination with topoisomerase inhibitors; as a chemosensitizer in combination with fraudulent nucleosides; as a chemosensitizer in combination with fraudulent nucleotides; as a chemosensitizer in combination with thymidylate synthetase inhibitors; as a chemosensitizer in combination with signal transduction inhibitors; as a chemosensitizer in combination with cisplatin or platinum analogs; as a chemosensitizer in combination with alkylating agents; as a chemosensitizer in combination with anti-tubulin agents; as a chemosensitizer in combination with antimetabolites; as a chemosensitizer in combination with berberine; as a chemosensitizer in combination with apigenin; as a chemosensitizer in combination with colchicine or colchicine analogs; as a chemosensitizer in combination with genistein; as a chemosensitizer in combination with etoposide; as a chemosensitizer in combination with cytarabine; as a chemosensitizer in combination with camptothecins; as a chemosensitizer in combination with vinca alkaloids; as a chemosensitizer in combination with topoisomerase inhibitors; as a chemosensitizer in combination with 5-fluorouracil; as a chemosensitizer in combination with curcumin; as a chemosensitizer in combination with NF-κB inhibitors; as a chemosensitizer in combination with rosmarinic acid; or as a chemosensitizer in combination with mitoguazone.

XVI. Chemopotentiation

Improvements for suboptimal chemotherapeutics including substituted alkylating agents such as uracil mustard are made by exploiting them as chemopotentiators where minimal therapeutic activity is observed alone but in combination with other therapeutics a more than additive or synergistic improvement in efficacy is observed. General examples include: uracil mustard with cisplatin or 5-FU. Specific inventive examples for substituted alkylating agents such as uracil mustard include: as a chemopotentiator in combination with topoisomerase inhibitors; as a chemopotentiator in combination with fraudulent nucleosides; as a chemopotentiator in combination with fraudulent nucleotides; as a chemopotentiator in combination with thymidylate synthetase inhibitors; as a chemopotentiator in combination with signal transduction inhibitors; as a chemopotentiator in combination with cisplatin or platinum analogs; as a chemopotentiator in combination with other alkylating agents; as a chemopotentiator in combination with anti-tubulin agents; as a chemopotentiator in combination with antimetabolites; as a chemopotentiator in combination with berberine; as a chemopotentiator in combination with apigenin; as a chemopotentiator in combination with colchicine or analogs of colchicine; as a chemopotentiator in combination with genistein; as a chemopotentiator in combination with etoposide; as a chemopotentiator in combination with cytarabine; as a chemopotentiator in combination with camptothecins; as a chemopotentiator in combination with vinca alkaloids; as a chemopotentiator in combination with 5-fluorouracil; as a chemopotentiator in combination with curcumin; as a chemopotentiator in combination with NF-κB inhibitors; as a chemopotentiator in combination with rosmarinic acid; or as a chemopotentiator in combination with mitoguazone.

XVII. Post-Treatment Patient Management

Improvements for suboptimal chemotherapeutics including substituted alkylating agents such as uracil mustard are made by drugs, treatments and diagnostics to allow for the maximum benefit to patients treated with a compound. General examples include: pain management, nutritional support, anti-emetics, anti-nausea therapies, anti-anemia therapy, anti-inflammatories. Specific inventive examples for substituted alkylating agents such as uracil mustard include: use with therapies associated with pain management; nutritional support; anti-emetics; anti-nausea therapies; anti-anemia therapy; anti-inflammatories: antipyretics; or immune stimulants.

XVIII. Alternative Medicine/Therapeutic Support

Improvements for suboptimal chemotherapeutics including substituted alkylating agents such as uracil mustard are made by the use of unapproved/non-conventional therapeutics or methods to enhance effectiveness or reduce side effects. General examples include: hypnosis, acupuncture, meditation, herbal medications and extracts, applied kinesiology. Specific inventive examples for substituted alkylating agents such as uracil mustard include: hypnosis; acupuncture; meditation; herbal medications created either synthetically or through extraction including NF-κB inhibitors (such as parthenolide, curcumin, or rosmarinic acid); natural anti-inflammatories (including rhein or parthenolide); immunostimulants (such as those found in *Echinacea*); antimicrobials (such as berberine); flavonoids and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); or applied kinesiology.

XIX. Bulk Drug Product Improvements

Improvements for suboptimal chemotherapeutics including substituted alkylating agents such as uracil mustard are made by alterations in the pharmaceutical bulk substance. General examples include: salt formation, homogeneous crystalline structure, pure isomers. Specific inventive examples for substituted alkylating agents such as uracil mustard include: the free base; salt formation; homogeneous crystalline structure; amorphous structure, pure isomers; increased purity; polymorphs; or lower residual solvents and heavy metals.

XX. Diluent Systems

Improvements for suboptimal chemotherapeutics including substituted alkylating agents such as uracil mustard are made by alterations in the diluents used to solubilize and deliver/present the compound for administration. General examples include: Cremophor-EL, cyclodextrins for poorly water soluble compounds. Specific inventive examples for substituted alkylating agents such as uracil mustard include: use of emulsions; dimethylsulfoxide (DMSO); N-methylformamide (NMF); dimethylformamide (DMF); dimethylacetamide (DMA); ethanol; benzyl alcohol; dextrose-containing water for injection; Cremophor; cyclodextrins; or PEG.

XXI. Solvent Systems

Improvements for suboptimal chemotherapeutics including substituted alkylating agents such as uracil mustard are made by alterations in the solvents used or required to solubilize a compound for administration or for further dilution. General examples include: ethanol, dimethylacetamide (DMA). Specific inventive examples for substituted alkylating agents such as uracil mustard include: the use of emulsions; DMSO; NMF; DMF; DMA; ethanol; benzyl alcohol; dextrose-containing water for injection; Cremophor; PEG; or salt systems.

XXII. Excipients

Improvements for suboptimal chemotherapeutics including substituted alkylating agents such as uracil mustard are made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for substituted alkylating agents such as uracil mustard include: the use of mannitol; the use of albumin; the use of EDTA; the use of sodium bisulfite; the use of benzyl alcohol; the use of carbonate buffers; the use of phosphate buffers; the use of polyethylene glycol (PEG); the use of vitamin A; the use of vitamin D; the use of vitamin E; the use of esterase inhibitors; the use of cytochrome P450 inhibitors; the use of multi-drug resistance (MDR) inhibitors; the use of organic resins; the use of detergents; the use of perillyl alcohol or an analog thereof; or the use of activators of channel-forming receptors.

XXIII. Dosage Forms

Improvements for suboptimal chemotherapeutics including substituted alkylating agents such as uracil mustard are made by alterations in the potential dosage forms of the compound dependent on the route of administration, duration of effect, plasma levels required, exposure to normal tissues potentially resulting in side effects, and exposure to metabolizing enzymes. General examples include: tablets, capsules, topical gels, creams, patches, suppositories. Specific inventive examples for substituted alkylating agents such as uracil mustard include: the use of tablets; the use of capsules; the use of topical gels; the use of topical creams; the use of patches; the use of suppositories; the use of lyophilized dosage fills; the use of immediate-release formulations; the use of slow-release formulations; the use of controlled-release formulations; the use of liquid in capsules; the use of 1-mg capsules; the use of 5-mg capsules; the use of 10-mg capsules; the use of 1-mg tablets; the use of 5-mg tablets; the use of 10-mg tablets; the use of coated tablets; the use of lyophilized dosages suitable for intravenous administration; the use of stable liquid formulations; or the use of stabilized compositions comprising uracil mustard and a non-aqueous carrier.

XXIV. Dosage Kits and Packaging

Improvements for suboptimal chemotherapeutics including substituted alkylating agents such as uracil mustard are made by alterations in the dosage forms, container/closure systems, accuracy of mixing and dosage preparation and presentation. General examples include: amber vials to protect from light, stoppers with specialized coatings. Specific inventive examples for substituted alkylating agents such as uracil mustard include: the use of amber vials to protect from light; or the use of stoppers with specialized coatings to improve shelf-life stability.

XXV. Drug Delivery Systems

Improvements for suboptimal chemotherapeutics including substituted alkylating agents such as uracil mustard are made by the use of delivery systems to improve the potential attributes of a pharmaceutical product such as convenience, duration of effect, or reduction of toxicities. General examples include: nanocrystals, bioerodible polymers, liposomes, slow release injectable gels, microspheres. Specific inventive examples for substituted alkylating agents such as uracil mustard include: the use of oral dosage forms; the use of nanocrystals; the use of nanoparticles; the use of cosolvents; the use of slurries; the use of syrups, the use of bioerodible polymers; the use of liposomes; the use of slow release injectable gels; the use of microspheres; the use of targeting compositions with epidermal growth factor receptor-binding peptides; the use of bispecific antibody pretargeting; the use of single chain variable region antibody fragments cloned by phage display as delivery agents for uracil mustard; or the use of polymeric micelles for drug delivery.

XXVI Drug Conjugate Forms

Improvements for suboptimal chemotherapeutics including substituted alkylating agents such as uracil mustard are made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, multivalent linkers. Specific inventive examples for substituted alkylating agents such as uracil mustard include: the use of polymer systems such as polyethylene glycols; the use of polylactides; the use of polyglycolides; the use of amino acids; the use of peptides; the use of multivalent linkers; the use of immunoglobulins; the use of cyclodextrin polymers; the use of modified transferrin; the use of hydrophobic or hydrophobic-hydrophilic polymers; the use of conjugates with a phosphonoformic acid partial ester; the use of conjugates with a cell-binding agent incorporating a charged cross-linker; the use of conjugates with β-glucuronides through a linker; the use of conjugates with anti-CD49 antibodies; the use of conjugates with activatable compounds; the use of conjugates with targetable constructs; the use of charged or pro-charged conjugates of cell binding agents and uracil mustard; the use of conjugates with anti-CD74 antibodies, typically with the administration of fingolimod; the use of conjugates with anti-GITR antibodies; the use of hypoxia-selective, weakly basic 2-nitroimidazole delivery agents covalently linked to uracil mustard; the use of a water-soluble non-peptidic polymer linked to uracil mustard; the use of a hydrohalide salt of a multi-arm water-soluble polyethylene glycol-uracil mustard conjugate; the use of pheophorbide-α conjugates with uracil mustard; the use of conjugates of uracil mustard with cancer-targeting peptides, in which the cancer-targeting peptides have a $PX_1LX_2$ motif, in which $X_1$ is His or an amino acid residue with a hydrophobic side chain and $X_2$ is Pro, Phe, or Trp; the use of a bioactive assembly formed using dock-and-lock methodology which takes advantage of the specific binding interaction between dimerization and docking domains (DDD) and anchoring domains (AD) to form the assembly conjugated to uracil mustard; or the use of a hexavalent molecular building block, wherein the linkage of additional moieties to the amino and carboxyl terminals of monomers comprising the NC2 domain of collagen IX promotes the directed association of those moieties via the trimerization initiating and stagger determining capacity of the NC2 domain of collagen IX, and wherein the NC2 domain of collagen X is conjugated to uracil mustard.

XVII Compound Analogs

Improvements for suboptimal chemotherapeutics including substituted alkylating agents such as uracil mustard are made are made by alterations to the parent structure of a molecule with additional chemical functionalities that may alter efficacy, reduce toxicity, improve pharmacological performance, be compatible with a particular route of administration, or alter the metabolism of the therapeutic agent. General examples include: alteration of side chains to increase or decrease lipophilicity, additional chemical functionalities to alter reactivity, electron affinity, binding capacity; salt forms. Specific inventive examples for substituted alkylating agents such as uracil mustard include: alteration of side chains to increase or decrease lipophilicity; additional chemical functionalities to alter reactivity, electron affinity, or binding capacity; salt forms; or attachment of nitroxide free-radical-containing groups.

XVIII Prodrug Systems

Improvements for suboptimal chemotherapeutics including substituted alkylating agents such as uracil mustard are made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for substituted alkylating agents such as uracil mustard include: the use of enzyme sensitive esters; the use of dimers; the use of Schiff bases; the use of pyridoxal complexes; the use of caffeine complexes; the use of nitric oxide-releasing prodrugs; or the use of prodrugs with fibroblast activation protein α-cleavable oligopeptides.

XXIX. Multiple Drug Systems

Improvements for suboptimal chemotherapeutics including substituted alkylating agents such as uracil mustard are made by the use of additional compounds, biological agents that when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for substituted alkylating agents such as uracil mustard include: the use of inhibitors of multi-drug resistance; the use of specific drug resistance inhibitors; the use of specific inhibitors of selective enzymes; the use of signal transduction inhibitors; the use of meisoindigo; the use of imatinib; the use of hydroxyurea; the use of dasatinib; the use of capecitabine; the use of nilotinib, the use of repair inhibition; the use of topoisomerase inhibitors with non-overlapping side effects; or the use of anti-nausea medications.

XXX. Biotherapeutic Enhancement

Improvements for suboptimal chemotherapeutics including substituted alkylating agents such as uracil mustard are made by its use in combination as sensitizers/potentiators with biological response modifiers. General examples include: use in combination as sensitizers/potentiators with biological response modifiers, cytokines, lymphokines, therapeutic antibodies, antisense therapies, gene therapies. Specific inventive examples for substituted alkylating agents such as uracil mustard include: use in combination as sensitizers/potentiators with biological response modifiers; use in combination as sensitizers/potentiators with cytokines; use in combination as sensitizers/potentiators with lymphokines; use in combination as sensitizers/potentiators with therapeutic antibodies; use in combination as sensitizers/potentiators with antisense therapies; use in combination as sensitizers/potentiators with gene therapies; use in combination as sensitizers/potentiators with ribozymes; or use in combination as sensitizers/potentiators with RNA interference.

XXXI. Biotherapeutic Resistance Modulation

Improvements for suboptimal chemotherapeutics including substituted alkylating agents such as uracil mustard are made by exploiting their selective use to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for substituted alkylating agents such as uracil mustard include: use against tumors resistant to the effects of biological response modifiers; use against tumors resistant to the effects of cytokines; use against tumors resistant to the effects of lymphokines; use against tumors resistant to the effects of therapeutic antibodies; use against tumors resistant to the effects of antisense therapies; use against tumors resistant to the effects of gene therapies; use against tumors resistant to the effects of ribozymes; or use against tumors resistant to the effects of RNA interference.

XXXII. Radiation Therapy Enhancement

Improvements for suboptimal chemotherapeutics including substituted alkylating agents such as uracil mustard are made by exploiting their use in combination with ionizing radiation, phototherapies, heat therapies, radio-frequency generated therapies. General examples include: hypoxic cell sensitizers, radiation sensitizers/protectors, photosensitizers, radiation repair inhibitors. Specific inventive examples for substituted alkylating agents such as uracil mustard include: use with hypoxic cell sensitizers; use with radiation sensitizers/protectors; use with photosensitizers; use with radiation repair inhibitors; use with thiol depletion; use with vaso-targeted agents; use with radioactive seeds; use with radionuclides; use with radiolabeled antibodies; or use with brachytherapy.

XXIII. Novel Mechanisms of Action

Improvements for suboptimal chemotherapeutics including substituted alkylating agents such as uracil mustard are made by optimizing their utility by determining the various mechanisms of actions, biological targets of a compound for greater understanding and precision to better exploit the utility of the molecule. General examples include: Gleevec for chronic myelocytic leukemia (CML), arsenic trioxide for acute promyelocytic leukemia (APL), retinoic acid for APL. Specific inventive examples for substituted alkylating agents such as uracil mustard include: use with inhibitors of poly-ADP ribose polymerase; use with agents that effect vasculature; use with agents that promote vasodilation; use with oncogenic targeted agents; use with signal transduction inhibitors; use with agents inducing EGFR inhibition; use with agents inducing Protein Kinase C inhibition; use with agents inducing Phospholipase C downregulation; use with agents inducing jun downregulation; use with agents modulating expression of histone genes; use with agents modulating expression of VEGF; use with agents modulating expression of ornithine decarboxylase; use with agents modulating expression of jun D; use with agents modulating expression of v-jun; use with agents modulating expression of GPCRs; use with agents modulating expression of protein kinase A; use with agents modulating expression of telomerase; use with agents modulating expression of prostate specific genes; use with agents modulating expression of protein kinases other than protein kinase A; or use with agents modulating expression of histone deacetylase.

XXIV. Selective Target Cell Population Therapeutics

Improvements for suboptimal chemotherapeutics including substituted alkylating agents such as uracil mustard are made by more precise identification and exposure of the compound to those select cell populations where the compounds effect can be maximally exploited. General examples include: tirapazamine and mitomycin c for hypoxic cells, vinca alkaloids for cells entering mitosis. Specific inventive examples for substituted alkylating agents such as uracil mustard include: use against radiation sensitive cells; use against radiation resistant cells; use against energy depleted cells; or use against endothelial cells.

XXXV. Use with Agents to Enhance Activity

Improvements for suboptimal chemotherapeutics including substituted alkylating agents such as uracil mustard are made by use of agents to enhance activity of the substituted alkylating agent. General examples include: use with nicotinamide, caffeine, tetandrine, or berberine. Specific inventive examples for substituted alkylating agents such as uracil mustard include: use with nicotinamide; use with caffeine; use with tetandrine; or use with berberine.

Accordingly, one aspect of the present invention is a method to improve the efficacy and/or reduce the side effects of suboptimally administered drug therapy comprising the steps of:

(1) identifying at least one factor or parameter associated with the efficacy and/or occurrence of side effects of the drug therapy; and (2) modifying the factor or parameter to improve the efficacy and/or reduce the side effects of the drug therapy;

wherein the drug therapy is administration of a mustard-based alkylating agent.

Typically, the factor or parameter is selected from the group consisting of:

(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation;
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics; and
(34) use with an agent enhancing its activity.

In one alternative, the suboptimally administered drug therapy is administration of uracil mustard.

In another alternative, the suboptimally administered drug therapy is administration of a mustard-based alkylating agent selected from the group consisting of:

(1) uracil mustard;
(2) 6-methyluracil mustard;
(3) 6-ethyluracil mustard;
(4) 6-propyluracil mustard;
(5) 3-[1-methyl-4-[1-methyl-4-[1-methyl-4-[N1-[5-bis(2-chloroethyl)amino-2,4-(1H,3H)pyrimidinedione]acetylamino]-pyrrole-2-carboxamido]pyrrole-2-carboxamido]pyrrole-2-carboxamido]propionamidine hydrochloride;
(6) 3-[1-methyl-4-[1-methyl-4-[1-methyl-4-[N1-[5-bis(2-chloroethyl)amino-2,4-(1H,3H)pyrimidinedione]pro- (7) 3-[1-methyl-4-[1-methyl-4-[1-methyl-4-[N1-[5-bis(2-chloroethyl)amino-2,4-(1H,3H)pyrimidinedione]butanoylamino]-pyrrole-2-carboxamido]pyrrole-2-carboxamido]pyrrole-2-carboxamido]propionamidine hydrochloride;
(8) 3-[1-methyl-4-[1-methyl-4-[1-methyl-4-[N1-[5-bis(2-chloroethyl)amino-2,4-(1H,3H)pyrimidinedione]pentanoylamino]-pyrrole-2-carboxamido]pyrrole-2-carboxamido]pyrrole-2-carboxamido]propionamidine hydrochloride;
(9) 3-[1-methyl-4-[1-methyl-4-[1-methyl-4-[N1-[5-bis(2-chloroethyl)amino-2,4-(1H,3H)pyrimidinedione] hexanoylamino]-pyrrole-2-carboxamido]pyrrole-2-carboxamido]pyrrole-2-carboxamido]propionamidine hydrochloride;
(10) 3-[1-methyl-4-[1-methyl-4-[1-methyl-4-[N1-[5-bis(2-chloroethyl)amino-2,4-(1H,3H)pyrimidinedione]heptanoylamino]-pyrrole-2-carboxamido]pyrrole-2-carboxamido]pyrrole-2-carboxamido]propionamidine hydrochloride;
(11) estramustine;
(12) derivatives of estramustine;
(13) quinacrine mustard dihydrochloride;
(14) derivatives of quinacrine mustard dihydrochloride;
(15) phosphoramide mustard;
(16) derivatives of phosphoramide mustard;
(17) spiromustine;
(18) derivatives of spiromustine;
(19) mustamine;
(20) derivatives of mustamine;
(21) phenylalanine mustard;
(22) derivatives of phenylalanine mustard;
(23) mannomustine;
(24) derivatives of mannomustine;
(25) 5-((bis(2-chloroethyl)amino)methyl)-pyrimidine-2,4 (1H,3H)-dione;
(26) 5-((bis(2-chloroethyl)amino)methyl)-6-methylpyrimidine-2,4(1H,3H)-dione;
(27) 5-((bis(2-chloroethyl)amino)methyl)-1-methylpyrimidine-2,4(1H,3H)-dione;
(28) 5-((bis(2-chloroethyl)amino)methyl)-1,3-dimethylpyrimidine-2,4(1H,3H)-dione;
(29) 5-((bis(2-chloroethyl)amino)methyl)-6-propylpyrimidine-2,4(1H,3H)-dione;
(30) 5-((bis(2-chloroethyl)amino)methyl)-6-methyl-2-thioxo-2,3-dihydropyrimidin-4(1H)-one;
(31) nitrouracil;
(32) 5,6-dihydro-5-nitrouracil;
(33) 5,6-dihydro-5-nitro-1-(4-nitrophenyl)uracil;
(34) 5-nitro-1-(4-nitrophenyl)uracil;
(35) 5,6-dihydro-5-nitro-1-(β-D-ribofuranuronic acid ethyl ester)uracil;
(36) 5-nitro-1-(β-D-ribofuranuronic acid ethyl ester)uracil;
(37) 5-nitrouracil N-oxide;
(38) prednimustine;
(39) derivatives of prednimustine;
(40) nimustine;
(41) derivatives of nimustine;
(42) ranimustine;
(43) derivatives of ranimustine;
(44) carmustine;
(45) derivatives of carmustine;
(46) lomustine;
(47) derivatives of lomustine;
(48) fotemustine;
(49) derivatives of fotemustine;
(50) ribomustine;
(51) derivatives of ribomustine;
(52) cystemustine;
(53) derivatives of cystemustine;
(54) 4-chlorouracil mustard;
(55) 4-substituted uracil mustard derivatives;
(56) 4-cyanouracil mustard;
(57) 4-nitrouracil mustard;
(58) derivatives of 4-chlorouracil mustard;
(59) derivatives of 4-substituted uracil mustard derivatives;
(60) derivatives of 4-cyanouracil mustard;
(61) derivatives of 4-nitrouracil mustard;
(62) a derivative or analog of uracil mustard or of alternatives (1)-(61) including one or more optional substituents, provided that the optionally substituted amonafide derivative or analog possesses substantially equivalent pharmacological activity to uracil mustard as determined by DNA alkylation activity;
and the derivatives, active metabolites, bioisosteres, salts, and solvates thereof (referred to herein as "Alternatives (1)-(62)").

Additional derivatives or analogs of uracil mustard can be produced by covalently coupling a derivative or analog of uracil mustard to another therapeutically active agent. Such covalent coupling reactions are well known in the art and can include, but are not limited to, reactions of amines with isothiocyanates, reactions of amines with thiocyanates, reactions of amines with acyl azides, reactions of amines with N-hydroxysuccinimide esters, reactions of amines with sulfonyl chlorides, reactions of amines with aldehydes or glyoxals, reactions of amines with epoxides or oxirantes, reactions of amines with carbonates, reactions of amines with arylating agents, reactions of amines with imidoesters, reactions of amines with carbodiimides, reactions of amines with anhydrides, reactions of amines with fluorophenyl esters, reactions of thiols with haloacetyl and alkyl halide derivatives, reactions of thiols with maleimides, reactions of thiols with aziridines, reactions of thiols with acryloyl derivatives, reactions of thiols with arylating agents, reactions of carboxylates with diazoalkanes or diazoacetyl compounds, reactions of carboxylates with carbonyldiimidazole, reactions of carboxylates with carbodiimides, reactions of hydroxyls with epoxides or oxiranes, reactions of hydroxyls with carbonyldiimidazole, reactions of hydroxyls with N,N'-disuccinimidyl carbonate or N,N'-hydroxysuccinimidyl chloroformate, reactions of hydroxyls with alkyl halogens, reactions of hydroxyls with isocyanates, reactions of aldehydes or ketones with hydrazine derivatives, reaction of aldehydes or ketones with amines and compounds with active hydrogens (Mannich condensation), reactions involving the coupling of a diene with an alkene (Diels-Alder reaction), $Cu^{1+}$-promoted azide-alkyne[3+2] cycloaddition (click chemistry) and other reactions known in the art, such as the reactions described in G. T. Hermanson, "Bioconjugate Techniques" (2d ed., Academic Press, Amsterdam, 2008), pp. 169-212, incorporated hereby by this reference. Other reactions suitable for coupling are known in the art, including Michael addition. Such coupling can occur with the use of a linker or without the use of a linker. Suitable linkers are known in the art and can be, for example, peptide linkers, linkers consisting of alkyl groups, or other linkers. Linkers are described in United States Patent Application Publication No. 2008/0213249 by Sinha et al., incorporated herein by this reference.

In another alternative, the suboptimally administered drug therapy is administration of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom.

Typically, when the suboptimally administered drug therapy is used to treat a hyperproliferative disease, the hyperproliferative disease is cancer. Methods according to the present invention and compositions according to the present invention suitable for use in those methods are applicable to many forms of cancer, including, but not limited to: (A) breast cancer, including: (1) ductal carcinoma, including ductal carcinoma in situ (DCIS) (comedocarcinoma, cribriform, papillary, micropapillary), infiltrating ductal carcinoma (IDC), tubular carcinoma, mucinous (colloid) carcinoma, papillary carcinoma, metaplastic carcinoma, and inflammatory carcinoma; (2) lobular carcinoma, including lobular carcinoma in situ (LCIS) and invasive lobular carcinoma; and (3) Paget's disease of the nipple; (B) cancers of the female reproductive system, including: (1) cancers of the cervix uteri, including cervical intraepithelial neoplasia (Grade I), cervical intraepithelial neoplasia (Grade II), cervical intraepithelial neoplasia (Grade III) (squamous cell carcinoma in situ), keratinizing squamous cell carcinoma, nonkeratinizing squamous cell carcinoma, verrucous carcinoma, adenocarcinoma in situ, adenocarcinoma in situ, endocervical type, endometrioid adenocarcinoma, clear cell adenocarcinoma, adenosquamous carcinoma, adenoid cystic carcinoma, small cell carcinoma, and undifferentiated carcinoma; (2) cancers of the corpus uteri, including endometrioid carcinoma, adenocarcinoma, adenocanthoma (adenocarcinoma with squamous metaplasia), adenosquamous carcinoma (mixed adenocarcinoma and squamous cell carcinoma, mucinous adenocarcinoma, serous adenocarcinoma, clear cell adenocarcinoma, squamous cell adenocarcinoma, and undifferentiated adenocarcinoma; (3) cancers of the ovary, including serous cystadenoma, serous cystadenocarcinoma, mucinous cystadenoma, mucinous cystadenocarcinoma, endometrioid tumor, endometrioid adenocarcinoma, clear cell tumor, clear cell cystadenocarcinoma, and unclassified tumor; (4) cancers of the vagina, including squamous cell carcinoma and adenocarcinoma; and (5) cancers of the vulva, including vulvar intraepithelial neoplasia (Grade I), vulvar intraepithelial neoplasia (Grade II), vulvar intraepithelial neoplasia (Grade III) (squamous cell carcinoma in situ); squamous cell carcinoma, verrucous carcinoma, Paget's disease of the vulva, adenocarcinoma (NOS), basal cell carcinoma (NOS), and Bartholin's gland carcinoma; (C) cancers of the male reproductive system, including: (1) cancers of the penis, including squamous cell carcinoma; (2) cancers of the prostate, including adenocarcinoma, sarcoma, and transitional cell carcinoma of the prostate; (3) cancers of the testis, including seminomatous tumor, nonseminomatous tumor, teratoma, embryonal carcinoma, yolk sac tumor, and Choriocarcinoma; (D) cancers of the cardiac system, including sarcoma (angiosarcoma, fibrosarcoma, rhabdomyosarcoma, liposarcoma), myxoma, rhabdomyoma, fibroma, lipoma and teratoma; (E) cancers of the respiratory system, including squamous cell carcinoma of the larynx, primary pleural mesothelioma, and squamous cell carcinoma of the pharynx; (F) cancers of the lung, including squamous cell carcinoma (epidermoid carcinoma), variants of squamous cell carcinoma, spindle cell carcinoma, small cell carcinoma, carcinoma of other cells, carcinoma of intermediate cell type, combined oat cell carcinoma, adenocarcinoma, acinar adenocarcinoma, papillary adenocarcinoma, bronchiolo-alveolar carcinoma, solid carcinoma with mucus formation, large cell carcinoma, giant cell carcinoma, clear cell carcinoma, and sarcoma; (G) cancers of the gastrointestinal tract, including: (1) cancers of the ampulla of Vater, including primary adenocarcinoma, carcinoid tumor, and lymphoma; (2) cancers of the anal canal, including adenocarcinoma, squamous cell carcinoma, and melanoma; (3) cancers of the extrahepatic bile ducts, including carcinoma in situ, adenocarcinoma, papillary adenocarcinoma, adenocarcinoma, intestinal type, mucinous adenocarcinoma, clear cell adenocarcinoma, signet-ring cell carcinoma, adenosquamous carcinoma, squamous cell carcinoma, small cell (oat) carcinoma, undifferentiated carcinoma, carcinoma (NOS), sarcoma, and carcinoid tumor; (4) cancers of the colon and rectum, including adenocarcinoma in situ, adenocarcinoma, mucinous adenocarcinoma (colloid type; greater than 50% mucinous carcinoma), signet ring cell carcinoma (greater than 50% signet ring cell), squamous cell (epidermoid) carcinoma, adenosquamous carcinoma, small cell (oat cell) carcinoma, undifferentiated carcinoma, carcinoma (NOS), sarcoma, lymphoma, and carcinoid tumor; (5) cancers of the esophagus, including squamous cell carcinoma, adenocarcinoma, leiomyosarcoma, and lymphoma; (6) cancers of the gallbladder, including adenocarcinoma, adenocarcinoma, intestinal type, adenosquamous carcinoma, carcinoma in situ, carcinoma (NOS), clear cell adenocarcinoma, mucinous adenocarcinoma, papillary adenocarcinoma, signet-ring cell carcinoma, small cell (oat cell) carcinoma, squamous cell carcinoma, and undifferentiated carcinoma; (7) cancers of the lip and oral cavity, including squamous cell carcinoma; (8) cancers of the liver, including hepatoma (hepatocellular carcinoma), cholangiocarcinoma, hepatoblastoma, angiosarcoma, hepatocellular adenoma, and hemangioma; (9) cancers of the exocrine pancreas, including duct cell carcinoma, pleomorphic giant cell carcinoma, giant cell carcinoma, osteoclastoid type, adenocarcinoma, adenosquamous carcinoma, mucinous (colloid) carcinoma, cystadenocarcinoma, acinar cell carcinoma, papillary carcinoma, small cell (oat cell) carcinoma, mixed cell typed, carcinoma (NOS), undifferentiated carcinoma, endocrine cell tumors arising in the islets of Langerhans, and carcinoid; (10) cancers of the salivary glands, including acinic (acinar) cell carcinoma, adenoid cystic carcinoma (cylindroma), adenocarcinoma, squamous cell carcinoma, carcinoma in pleomorphic adenoma (malignant mixed tumor), mucoepidermoid carcinoma (well differentiated or low grade), and mucoepidermoid carcinoma (poorly differentiated or high grade); (11) cancers of the stomach, including adenocarcinoma, papillary adenocarcinoma, tubular adenocarcinoma, mucinous adenocarcinoma, signet ring cell carcinoma, adenosquamous carcinoma, squamous cell carcinoma, small cell carcinoma, undifferentiated carcinoma, lymphoma, sarcoma, and carcinoid tumor; and (12) cancers of the small intestine, including adenocarcinoma, lymphoma, carcinoid tumors, Kaposi's sarcoma, leiomyoma, hemangioma, lipoma, neurofibroma, and fibroma; (H) cancers of the urinary system, including: (1) cancers of the kidney, including renal cell carcinoma, carcinoma of Bellini's collecting ducts, adenocarcinoma, papillary carcinoma, tubular carcinoma, granular cell carcinoma, clear cell carcinoma (hypernephroma), sarcoma of the kidney, and nephroblastoma; (2) cancers of the renal pelvis and ureter, including transitional cell carcinoma, papillary transitional cell carcinoma, squamous cell carcinoma, and adenocarcinoma; (3) cancers of the urethra, including transitional cell carcinoma, squamous cell carcinoma, and adenocarcinoma; and (4) cancers of the urinary bladder, including carcinoma in situ, transitional urothelial cell carcinoma, papillary transitional cell carcinoma, squamous cell carcinoma, adenocarcinoma, undifferentiated; (I) cancers of muscle, bone, and soft tissue, including: (1) cancers of bone, including: (a) bone-forming: osteosarcoma; (b) cartilage-forming: chondrosarcoma and mesenchymal chondrosarcoma; (c) giant cell tumor, malignant; (d) Ewing's sarcoma; (e) vascular tumors: hemangioendothelioma, hemangiopericytoma, and angiosarcoma; (f) connective tissue tumors: fibrosarcoma, liposarcoma, malignant mesenchymoma, and undifferentiated sarcoma; and (g) other tumors: chordoma and adamantinoma of long bones; (2) cancers of soft tissues, including: alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, rhabdomyosarcoma, synovial sarcoma, and sarcoma (NOS); (3) cancers of the nervous system, including cancers of the skull (osteoma, hemangioma, granuloma, xanthoma, osteitis deformans), cancers of the meninges (meningioma, meningiosarcoma, gliomatosis), cancers of the brain (astrocytoma, medulloblastoma, glioma, ependymoma, germinoma (pilealoma), glioblastoma multiforme, oligodendroglioma, schwannoma, retinoblastoma, congenital tumors), and cancers of the spinal cord neurofibroma, meningioma, glioma, sarcoma); (4) hematologic cancers, including myeloid leukemia (acute and chronic), acute lymphoblastic leukemia, chronic lymphocytic leukemia, myeloproliferative diseases, multiple myeloma; myelodysplastic syndrome), Hodgkin's disease, and non-Hodgkin's lymphoma (malignant lymphoma); (5) cancers of the endocrine system, including: (a) cancers of the thyroid gland, including papillary carcinoma (including those with follicular foci), follicular carcinoma, medullary carcinoma, and undifferentiated (anaplastic) carcinoma; and (b) neuroblastomas, including sympathicoblastoma, sympathicogonioma, malignant ganglioneuroma, gangliosympathicoblastoma, and ganglioneuroma; (6) cancers of the skin, including squamous cell carcinoma, spindle cell variant of squamous cell carcinoma, basal cell carcinoma, adenocarcinoma developing from sweat or sebaceous gland, and malignant melanoma; (7) cancers of the eye, including: (a) cancers of the conjunctiva, including carcinoma of the conjunctiva; (b) cancers of the eyelid, including basal cell carcinoma, squamous cell carcinoma, melanoma of the eyelid, and sebaceous cell carcinoma; (c) cancers of the lacrimal gland, including adenocarcinoma, adenoid cystic carcinoma, carcinoma in pleomorphic adenoma, mucoepidermoid carcinoma, and squamous cell carcinoma; (d) cancers of the uvea, including spindle cell melanoma, mixed cell melanoma, and epithelioid cell melanoma; (e) cancers of the orbit, including sarcoma of the orbit, soft tissue tumor, and sarcoma of bone; and (f) retinoblastoma. In particular, uracil mustard is effective for treatment of chronic lymphocytic leukemia, lymphomas of the follicular or lymphocytic type, mycosis fungoides, chronic myelogenous leukemia, polycythemia vera, ovarian carcinoma, and carcinoma of the lung.

The following improvements all apply either to uracil mustard itself, to other mustard-based alkylating agents, or to alkylating agents having either: (1) a nitrosourea moiety therein and having one haloalkyl moiety covalently bound to the nitrogen of the nitrosourea group not bound to the oxygen; or (2) two haloalkyl moieties bound to a nitrogen atom as indicated with respect to the specific improvement indicated below, unless either uracil mustard or other mustard-based alkylating agents are specifically indicated.

When the improvement is made by dose modification, the dose modification can be, but is not limited to, at least one dose modification selected from the group consisting of:
(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) doses less than 1 mg/m$^2$ for greater than 14 days;
(f) use of caffeine to modulate metabolism;
(g) use of isoniazid to modulate metabolism;
(h) selected and intermittent boost dose administrations;
(i) bolus single and multiple doses of 1-5 mg/m$^2$;
(j) oral dosing including multiple daily dosing;
(k) micro-dosing;
(l) immediate release dosing;
(m) slow release dosing;
(n) controlled release dosing;
(o) dosages of 0.15 mg/kg;
(p) dosages of 0.30 mg/kg;
(q) dosages of 0.45 mg/kg;
(r) dosages of 0.60 mg/kg;
(s) dosages above 0.15 mg/kg/day to 1 mg/kg/wk;
(t) dosages above 1 mg/day to 4 mg/day; and
(u) dosages above 0.15 mg/kg every 2 weeks to 1 mg/kg for three days per week.

When the improvement is made by route of administration, the route of administration can be, but is not limited to, a route of administration selected from the group consisting of:
(a) topical administration;
(b) intravesicular administration for bladder cancer;
(c) oral administration;
(d) slow release oral delivery;
(e) intrathecal administration;
(f) intraarterial administration;
(g) continuous infusion; and
(h) intermittent infusion.

When the improvement is made by schedule of administration, the schedule of administration can be, but is not limited to, a schedule of administration selected from the group consisting of:
(a) daily administration;
(b) weekly administration;
(c) weekly administration for three weeks;
(d) weekly administration for two weeks;
(e) biweekly administration;
(f) biweekly administration for three weeks with a 1-2 week rest period;
(g) intermittent boost dose administration; and
(h) administration daily for one week then once per week for multiple weeks.

When the improvement is made by an indication for use, the indication for use can be, but is not limited to, an indication for use selected from the group consisting of:
(a) use for the treatment of leukemias;
(b) use for treatment of myelodysplastic syndrome;
(c) use for treatment of angiogenic diseases;
(d) use for treatment of benign prostate hypertrophy;
(e) use for treatment of psoriasis;
(f) use for treatment of gout;
(g) use for treatment of autoimmune conditions;
(h) use for prevention of transplantation rejection,
(i) use for restenosis prevention in cardiovascular disease;
(j) use for treatment of mycosis fungoides;
(k) use in bone marrow transplantation;
(l) use as an anti-infective agent;

(m) use in treatment for AIDS;
(n) use in treatment for lymphoma generally;
(o) use in treatment of blast crisis in chronic myelocytic lymphoma;
(p) use in treatment of cutaneous T-cell lymphoma;
(q) use in treatment of reticulum cell sarcoma;
(r) use in treatment of large cell lymphoma;
(s) use in treatment of lung cancer characterized by overexpression of EGFR;
(t) use in treatment of ovarian cancer resistant to topoisomerase I inhibitors; and
(u) use in treatment of cancers resistant to platinum-containing therapeutic agents, including ovarian cancer and lung cancer.

Blast crisis is the final phase in the evolution of chronic myelocytic leukemia, in which the disease behaves like an acute leukemia, with rapid progression and short survival (A. Tefferi, "Classification, Diagnosis and Management of Myeloproliferative Disorders in the JAK2V617F Era," *Hematol. Am. Soc. Hematol. Educ. Program* (2006), pp. 240-245, incorporated herein by this reference). Typically, blast crisis is diagnosed if any of the following is present in a patient with chronic myelocytic leukemia: >20% myeloblasts or lymphocytes in the blood or bone marrow; large clusters of blasts in the bone marrow on biopsy; or development of a chloroma (solid focus of leukemia outside the bone marrow) (M. K. Esfahani et al., "Blastic Phase of Chronic Myelogenous Leukemia," *Curr. Treat. Options Oncol.* 7: 189-199 (2006), incorporated herein by this reference). Although imatinib and other tyrosine kinase inhibitors are typically used in an attempt to control or manage blast crisis, in many cases, multiple BCR-ABL kinase domain mutations confer resistance to imatinib and other tyrosine kinase inhibitors (N. P. Shah et al., "Multiple BCR-ABL Kinase Domain Mutations Confer Polyclonal Resistance to the Tyrosine Kinase Inhibitor Imatinib (STI571) in Chronic Phase and Blast Crisis Chronic Myeloid Leukemia," *Cancer Cell* 2: 117-125 (2002), incorporated herein by this reference).

Cutaneous T-cell lymphoma is a class of non-Hodgkin's lymphomas. Unlike most non-Hodgkin's lymphomas, which are typically B-cell related, cutaneous T-cell lymphoma is caused by a mutation of T cells. The malignant T cells initially migrate to the skin, causing various lesions, typically appearing as a rash and then forming plaques and tumors that can metastasize. Currently improved treatments include denileukin diftitox, which is an engineered fusion protein combining interleukin-2 and diphtheria (F. Tuturro, "Denileukin Diftitox: A Biotherapeutic Paradigm Shift in the Treatment of Lymphoid-Derived Disorders," *Exp. Rev. Anticancer Ther.* 7: 11-17 (2007), incorporated herein by this reference); bexarotene, which is a retinoid; and vorinostat and romidepsin, which are cyclic peptide histone deacetylase inhibitors.

Large-cell lymphoma includes a number of types of lymphomas in which the aberrantly proliferating cells are of large diameter, typically about 17 μm to about 20 μm. These lymphomas include diffuse large B-cell lymphoma, angiocentric lymphoma, Burkitt's lymphoma, follicular large-cell lymphoma, immunoblastic lymphoma, intravascular large-cell lymphoma, primary mediastinal B-cell lymphoma, and primary central nervous system lymphoma. One treatment for at least some types of large-cell lymphomas is the NEMO-binding domain peptide (A. Gaurnier-Hausser et al., "NEMO-Binding Domain Peptide Inhibits Constitutive NF-κB Activity and Reduces Tumor Burden in a Canine Model of Relapsed, Refractory Diffuse Large B-Cell Lymphoma," *Clin. Cancer Res.* 17: 4661-4671 (2011), incorporated herein by this reference).

Overexpression of epidermal growth factor receptor (EGFR) and its ligand transforming growth factor α (TGFα) is common in many varieties of lung cancer, especially non-small-cell lung cancer (V. Rusch et al., "Overexpression of the Epidermal Growth Factor Receptor and Its Ligand Transforming Growth Factor Alpha Is Frequent in Resectable Non-Small Cell Lung Cancer but Does Not Predict Tumor Progression," *Clin. Cancer Res.* 3: 515 (1997), incorporated herein by this reference). Survival after EGFR inhibitor treatment may be influenced both by the degree of overexpression and mutations occurring in EGFR (S. M. Lee, "Is EGFR Expression Important in Non-Small Cell Lung Cancer," *Thorax* 61: 98-99 (2006), incorporated herein by this reference). In some cases, mutations in EGFR can increase sensitivity, at least temporarily, to gefitinib or erlotinib; typically, these mutations involved either in-frame deletions in exon 19, single missense mutations in exon 21, or in-frame duplications/insertions in exon 20. However, over time, relapse frequently occurs, and is typically associated with a second mutation, at position T790M, in the catalytic cleft of the EGFR tyrosine kinase domain, thereby preventing access by gefitinib.

Ovarian cancer may be resistant to topoisomerase I inhibitors, which are frequently used to treat ovarian cancer. Such resistance can occur to topotecan, SN-38 (the active metabolite of irinotecan), and 9-aminocamptothecin. Such resistance may be due to overexpression of the resistance protein/mitoxantrone resistance/placenta-specific ATP binding cassette (BCRP/MXR/ABCP) gene (M. Maliepaard et al., "Overexpression of the BCRP/MXR/ABCP Gene in a Topotecan-Selected Ovarian Tumor Cell Line," *Cancer Res.* 59: 4559-4563 (1999), incorporated herein by this reference).

Reticulum cell sarcoma, also known as histiocytic lymphoma, is a rare form of non-Hodgkin's lymphoma characterized by the presence of large tumor cells resembling histiocytes morphologically but considered to be lymphoid in origin, either of T-cell origin or B-cell origin.

A number of platinum-containing chemotherapeutic drugs are in common use. These drugs include cisplatin, carboplatin, oxaliplatin, satraplatin, picoplatin, nedaplatin, and triplatin tetranitrate. These drugs form adducts with DNA which in turn blocks cell division and stimulates apoptosis. However, resistance to these drugs is common, particularly in ovarian cancer and lung cancer. A number of mechanisms of resistance have been proposed, including changes in cellular uptake and efflux of the drug, inhibition of apoptosis, and increased DNA repair, clearing the adducts from the DNA. The existence of mechanisms that can promote resistance means that patients treated with such platinum-containing chemotherapeutic drugs are prone to incur relapse.

Accordingly, one aspect of the present invention is a method of treating blast crisis with a mustard-based alkylating agent selected from the group consisting of Alternatives (1)-(62), either as a single therapeutic agent, or with one or more additional therapeutic agents, such as, but not limited to, imatinib or another tyrosine kinase inhibitor. Another aspect of the present invention is a method of treating cutaneous T-cell lymphoma with a mustard-based alkylating agent selected from the group consisting of Alternatives (1)-(62), either as a single therapeutic agent, or with one or more additional therapeutic agents, such as, but not limited to, denileukin difitox, bexarotene, vorinostat, and romidepsin. Yet another aspect of the present invention is a method of treating large-cell lymphoma with a mustard-based alkylating agent selected from the group consisting of Alternatives (1)-(62), either as a single therapeutic agent, or with one or more additional therapeutic agents, such as, but not limited to, a NEMO-binding domain peptide. Yet another aspect of the present invention is a method of treating lung cancer characterized by overexpression of either or both of epidermal growth factor receptor (EGFR) and its ligand transforming growth factor α (TGFα) with a mustard-based alkylating agent selected from the group consisting of Alternatives (1)-(62), either as a single therapeutic agent, or with one or more additional therapeutic agents, such as, but not limited to, gefitinib and erlotinib. The lung cancer characterized by overexpression of either or both of epidermal growth factor receptor (EGFR) and its ligand transforming growth factor α (TGFα) can be, but is not limited to, non-small cell lung cancer. The lung cancer can be characterized by a mutation at position T790M, in the catalytic cleft of the EGFR tyrosine kinase domain. Still another aspect of the present invention is a method of treating ovarian cancer resistant to topoisomerase I inhibitors with a mustard-based alkylating agent selected from the group consisting of Alternatives (1)-(62), either as a single therapeutic agent, or with one or more additional therapeutic agents, such as, but not limited to, topotecan, irinotecan, 9-aminocamptothecin, 7-ethyl-10-hydroxycamptothecin, and 7-ethyl-10-[4-(1-piperidino)-1-piperidino]carbonyloxy-camptothecin. The ovarian cancer resistant to topoisomerase inhibitors can be characterized by overexpression of the BCRP/MXR/ABCP gene. Still another aspect of the present invention is a method of treating ovarian cancer or breast cancer resistant to a platinum-containing chemotherapeutic drug with a mustard-based alkylating agent selected from the group consisting of Alternatives (1)-(62), either as a single therapeutic agent, or with one or more additional therapeutic agents, such as, but not limited to, cisplatin, carboplatin, oxaliplatin, satraplatin, picoplatin, nedaplatin, and triplatin tetranitrate.

When the improvement is made by selection of disease stage, the selection of disease stage can be, but is not limited to, at least one selection of disease stage selected from the group consisting of:
   (a) use for the treatment of localized polyp stage colon cancer;
   (b) use for the treatment of leukoplakia in the oral cavity;
   (c) use to induce angiogenesis inhibition to prevent or limit metastatic spread;
   (d) use against chronic myelogenous leukemia (CML) either together with tyrosine kinase inhibitors such as imatinib or homoharringtonine or subsequent to administration of tyrosine kinase inhibitors such as imatinib or homoharringtonine;
   (e) use against lymphoma either together with rituximab or bendamustine or subsequent to administration of rituximab or bendamustine; and
   (f) use against chronic lymphocytic leukemia either together with rituximab or bendamustine or subsequent to administration of rituximab or bendamustine.

When the improvement is made by other indications, the other indications can be, but are not limited to, at least one other indication selected from the group consisting of:
   (a) use as an anti-infective agent;
   (b) use as an antiviral agent;
   (c) use as an antibacterial agent;
   (d) use for control of pleural effusions;
   (e) use as an antifungal agent;
   (f) use as an antiparasitic agent;
   (g) use for treatment of eczema;
   (h) use for treatment of shingles;
   (i) use for treatment of condylomata;
   (j) use for treatment of human papilloma virus (HPV);
   (k) use against HIV with AZT, DDI, or reverse transcriptase inhibitors; and
   (l) use for treatment of herpes simplex virus (HSV).

When the improvement is made by patient selection, the patient selection can be, but is not limited to, a patient selection carried out by a criterion selected from the group consisting of:
   (a) selecting patients with a disease condition characterized by a high level of a metabolic enzyme selected from the group consisting of histone deacetylase, protein kinases, and ornithine decarboxylase;
   (b) selecting patients with a disease condition characterized by a low level of a metabolic enzyme selected from the group consisting of histone deacetylase, protein kinases, and ornithine decarboxylase;
   (c) selecting patients with a low or high susceptibility to a condition selected from the group consisting of thrombocytopenia and neutropenia;
   (d) selecting patients intolerant of GI toxicities;
   (e) selecting patients characterized by over- or underexpression of a gene selected from the group consisting of jun, GPCRs, signal transduction proteins, VEGF, prostate specific genes, protein kinases, and telomerase;
   (f) selecting patients failing to respond to or refractory to inhibitors of Bruton's tyrosine kinase (BTK), such as ibrutinib;
   (g) selecting patients with hepatic impairment who are not candidates for BTK inhibitors;
   (h) selecting patients with hepatic impairment who are not candidates for chlorambucil, cyclophosphamide, or bendamustine; and
   (i) selecting patients intolerant to, not a candidate for, or refractory to anti-CD20 antibodies.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, $β_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

Bruton's tyrosine kinase (BTK) is a tyrosine kinase enzyme that plays a crucial role in B-cell maturation and mast cell activation through the high-affinity IgE receptor. BTK is described in U.S. Pat. No. 6,326,469 to Ullrich et al., incorporated herein by this reference. BTK contains a Pleckstrin homology domain (PH domain) that binds phosphatidylinositol (3,4,5)-trisphosphate (PIP3). PIP3 binding induces BTK to phosphorylate phospholipase C, which in turn results in the generation of two second messengers, inositol phosphate and diacylglycerol, which act to modulate the activity of downstream proteins during B-cell signaling. The activity and functions of BTK are described in Y.-C. Ma & X.-Y. Huang, "Identification of the Binding Site for Gqa on Its Effector Bruton's Tyrosine Kinase," *Proc. Natl. Acad. Sci. USA* 95: 12197-12201 (1998); T. Yasuda et al., "Cbl-b Positively Regulates Btk-Mediated Activation of Phospholipase C-γ2 in B Cells," *J. Exp. Med.* 196: 51-63 (2002), both incorporated herein by this reference. BTK has been shown to interact with GNAQ, PLGC2, protein kinase D1, B-cell linker, SH3BP5, caveolin 1, ARID3A, and GTF2I. Because of its role in B-cell maturation and signaling, BTK has been recently been evaluated as a target for treatment in malignancies characterized by B-cell dysregulation, including mantle cell lymphoma, chronic lymphocytic leukemia, diffuse large B-cell lymphoma, and multiple myeloma. One BTK inhibitor is ibrutinib (1-[(3R)-3-[4-amino-3-(4-phenoxyphenyl)-1H-pyrazolo[3,4-d]pyrimidin-1-yl]piperidin-1-yl]prop-2-en-1-one). Other BTK inhibitors include, but are not limited to, GDC-0834 (N-[3-[6-[[4-[(2S)-1,4-dimethyl-3-oxo-2-piperazinyl]phenyl]amino]-4,5-dihydro-4-methyl-5-oxo-2-pyrazinyl]-2-methylphenyl]-4,5,6,7-tetrahydro-denzo[b]thiophene-2-carboxamide), AVL-292 (N-[3-[[5-fluoro-2-[[4-(2-methoxyethoxy)phenyl]amino]-4-pyrimidinyl]amino]phenyl]-2-propenamide), CNX-774 (4-(4-((4-((3-acrylamidophenyl)amino)-5-fluoropyrimidin-2-yl)amino)phenoxy)-N-methylpicolinamide), CGI-560 (4-(tert-butyl)-N-(3-(8-(phenylamino)imidazo[1,2-a]pyrazin-6-yl)phenyl)benzamide), CGI-1746 (N-[3-[4,5-dihydro-4-methyl-6-[[4-(4-morpholinylcarbonyl)phenyl]amino]-5-oxo-2-pyrazinyl]-2-methylphenyl]-4-(1,1-dimethylethyl)-benzamide), HM-71224, ONO-4059 RN-486 (6-cyclopropyl-8-fluoro-2-(2-hydroxymethyl)-3-(1-methyl-5-((5-(4-methylpiperazin-1-yl)pyridine-2-yl)amino-6-oxo-1,6-dihydropyridin-3-yl)phenyl)isoquinolin-1(2H)-one) and LFM-A13 (α-cyano-β-hydroxy-β-methyl-N-(2,5-dibromophenyl) propenamide). BTK inhibitors are described in A. Akinleye et al., "Ibrutinib and Novel BTK Inhibitors in Clinical Development," *J. Hematol. Oncol.* 6:59 (2013); R. W. Hendricks et al., "Targeting Bruton's Tyrosine Kinase in B Cell Malignancies," *Nature Rev. Cancer* 14: 219-232 (2014); and O. J. D'Cruz & F. M. Uckun, "Novel Bruton's Tyrosine Kinase Inhibitors Currently in Development," *Onco. Targets Ther.* 6: 161-176 (2013), all of which are incorporated herein by this reference.

Other BTK inhibitors are disclosed in U.S. Pat. No. 8,658,653 to Honigberg et al.; U.S. Pat. No. 8,563,563 to Honigberg et al.; U.S. Pat. No. 8,552,010 to Honigberg et al.; U.S. Pat. No. 8,501,751 to Honigberg et al.; U.S. Pat. No. 8,501,724 to Chen et al.; U.S. Pat. No. 8,497,277 to Honigberg et al.; U.S. Pat. No. 8,476,284 to Honigberg et al.; United States Patent Application Publication No. 2014/0080844 by Chen et al.; United States Patent Application Publication No. 2014/0079690 by Buggy et al.; United States Patent Application Publication No. 2014/0039186 by Honigberg et al.; United States Patent Application Publication No. 2013/0338172 by Smyth et al.; United States Patent Application Publication No. 2013/0310402 by Buggy et al.; United States Patent Application Publication No. 2013/0273030 by Buggy et al.; and United States Patent Application Publication No. 2013/0195852 by Buggy et al., all of which are incorporated herein by this reference. Typically, these BTK inhibitors are irreversible inhibitors that form a covalent bond through a Michael addition reaction with a cysteine residue on the BTK, such as cysteine 481. Typically, such inhibitors are pyrazolopyrimidines. Such inhibitors include, but are not limited to, (E)-1-(3-(4-amino-3-(4-phenoxyphenyl)-1H-pyrazolo[3,4-d]pyrimidin-1-yl) piperidin-1-yl)but-2-en-1-one; 1-(3-(4-amino-3-(4-phenoxyphenyl)-1H-pyrazolo[3,4-d]pyrimidin-1-yl)piperidin-1-yl)sulfonylethene; 1-(3-(4-amino-3-(4-phenoxyphenyl)-1H-pyrazolo[3,4-d]pyrimidin-1-yl) piperidin-1-yl)prop-2-yn-1-one; 1-(4-(4-amino-3-(4-phenoxyphenyl)-1H-pyrazolo[3,4-d]pyrimidin-1-yl) piperidin-1-yl)prop-2-en-1-one; N-((1 s,4s)-4-(4-amino-3-(4-phenoxyphenyl)-1H-pyrazolo[3,4-d]pyrimidin-1-yl) cyclohexyl)acrylamide; 1-((R)-3-(4-amino-3-(4-phenoxyphenyl)-1H-pyrazolo[3,4-d]pyrimidin-1-yl) pyrrolidin-1-yl)prop-2-en-1-one; 1-((S)-3-(4-amino-3-(4-phenoxyphenyl)-1H-pyrazolo[3,4-d]pyrimidin-1-yl) pyrrolidin-1-yl)prop-2-en-1-one; 1-((R)-3-(4-amino-3-(4-phenoxyphenyl)-1H-pyrazolo[3,4-d]pyrimidin-1-yl) piperidin-1-yl)prop-2-en-1-one; 1-((S)-3-(4-amino-3-(4-phenoxyphenyl)-1H-pyrazolo[3,4-d]pyrimidin-1-yl) piperidin-1-yl)prop-2-en-1-one; and (E)-1-(3-(4-amino-3-(4-phenoxyphenyl)-1H-pyrazolo[3,4-d]pyrimidin-1-yl) piperidin-1-yl)-4-(dimethylamino)but-2-en-1-one. Other BTK inhibitors are known in the art.

Chlorambucil (4-[bis(2-chlorethyl)amino]benzenebutanoic acid) is a nitrogen mustard alkylating agent that is particularly used in the treatment of chronic lymphocytic leukemia. Cyclophosphamide ((RS)—N,N-bis(2-chloroethyl)-1,3,2-oxazaphosphinan-2-amine 2-oxide) is a prodrug of a nitrogen mustard alkylating agent used to treat lymphomas, leukemias, and brain cancer as well as autoimmune disorders. Bendamustine (4-[5-[bis(2-chloroethyl) amino]-1-methylbenzimidazol-2-yl]butanoic acid) is a nitrogen mustard used in the treatment of chronic lymphocytic leukemia and lymphomas.

CD20 is an activated-glycosylated phosphoprotein antigen expressed on the surface of all B cells beginning at the pro-B phase (CD45R+, CD117+) and progressively increasing in concentration until maturity. A number of anti-CD-20 monoclonal antibodies are in use or being evaluated for treatment of B-cell lymphomas or leukemias, including ofatumumab, rituximab, alemtuzumab, ibritumomab tiuxetan, ocelizumab, and veltuzumab.

When the improvement is made by analysis of patient or disease phenotype, the analysis of patient or disease phenotype can be, but is not limited to, a method of analysis of patient or disease phenotype carried out by a method selected from the group consisting of:

(a) use of a diagnostic tool, a diagnostic technique, a diagnostic kit, or a diagnostic assay to confirm a patient's particular phenotype;

(b) use of a method for measurement of a marker selected from the group consisting of histone deacetylase, ornithine decarboxylase, VEGF, a protein that is a gene product of a prostate specific gene, a protein that is a gene product of jun, a protein kinase, desmoglein-3, and a caspase-derived neo-epitope;

(c) surrogate compound dosing; and (d) low dose pre-testing for enzymatic status.

The measurement of the protein desmoglein-3 as a marker of metastasis of a tumor to lymph nodes and the selection of appropriate therapy based on the amount of desmoglein-3 in a sample from a subject is described in United States Patent Application Publication No. 2012/0087892 by Gutkind et al., incorporated herein by this reference.

The measurement of caspase-derived neo-epitopes as an indicator of apoptosis, including apoptosis induced by antineoplastic agents, is described in United States Patent Application Publication No. 2012/0028266 by Wells et al., incorporated herein by this reference.

When the improvement is made by analysis of patient or disease genotype, the analysis of patient or disease genotype can be, but is not limited to, a method of analysis of patient or disease genotype carried out by a method selected from the group consisting of:

(a) use of a diagnostic tool, a diagnostic technique, a diagnostic kit, or a diagnostic assay to confirm a patient's particular genotype;

(b) use of a gene chip;

(c) use of gene expression analysis;

(d) use of single nucleotide polymorphism (SNP) analysis; and (e) measurement of the level of a metabolite or a metabolic enzyme.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference.

When the improvement is made by pre/post-treatment preparation, the pre/post-treatment preparation can be, but is not limited to, a method of pre/post treatment preparation selected from the group consisting of:

(a) the use of colchicine or an analog thereof;

(b) the use of a diuretic;

(c) the use of a uricosuric;

(d) the use of uricase;

(e) the non-oral use of nicotinamide;

(f) the use of a sustained-release form of nicotinamide;

(g) the use of an inhibitor of poly-ADP ribose polymerase;

(h) the use of caffeine;

(i) the use of leucovorin rescue;

(j) infection control; and (k) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:

(a) the use of colchicine or an analog thereof;

(b) the use of a uricosuric;

(c) the use of a diuretic;

(d) the use of uricase;

(e) the non-oral use of nicotinamide;

(f) the use of a sustained-release form of nicotinamide;

(g) the use of an inhibitor of polyADP-ribose polymerase;

(h) the use of caffeine;

(i) the use of leucovorin rescue;

(j) the use of sustained-release allopurinol;

(k) the non-oral use of allopurinol;

(l) the administration of bone marrow transplant stimulants, blood, platelet infusions, Neupogen, G-CSF; or GM-CSF;

(m) pain management;

(n) the administration of anti-inflammatories;

(o) the administration of fluids;

(p) the administration of corticosteroids;

(q) the administration of insulin control medications;

(r) the administration of antipyretics;

(s) the administration of anti-nausea treatments;

(t) the administration of anti-diarrhea treatments;

(u) the administration of N-acetylcysteine;

(v) the administration of antihistamines;

(w) the administration of agents for reduction of gastric toxicity; and (x) the administration of agents to reduce myelosuppression.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in Goodman & Gilman's The Pharmacological Basis of Therapeutics (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

Agents for reduction of gastric toxicity include, but are not limited to, ferruginol (C. Areche et al., "Gastroprotective Activity of Ferruginol in Mice and Rats: Effects on Gastric Secretion, Endogenous Prostaglandins and Non-Protein Sulfhydryls," J. Pharm. Pharmacol. 60: 245-251 (2008), incorporated herein by this reference).

Agents for counteracting myelosuppression include, but are not limited to, dithiocarbamates. U.S. Pat. No. 5,035,878 to Borch et al., incorporated herein by this reference, discloses dithiocarbamates for treatment of myelosuppression; the dithiocarbamates are compounds of the formula $R^1R^2NCS(S)M$ or $R^1R^2NCSS$—$SC(S)NR^3R^4$, wherein $R^1$, $R^2$, $R^3$, and $R^4$ are the same or different, and $R^1$, $R^2$, $R^3$, and $R^4$ are aliphatic, cycloaliphatic, or heterocycloaliphatic groups that are unsubstituted or substituted by hydroxyl; or wherein one of $R^1$ and $R^2$ and one of $R^3$ and $R^4$ can be hydrogen; or wherein $R^1$, $R^2$, $R^3$, and $R^4$ taken together with the nitrogen atom upon which the pair of R groups is substituted, can be a 5-membered or 6-membered N-heterocyclic ring which is aliphatic or aliphatic interrupted by a ring oxygen or a second ring nitrogen, and M is hydrogen or one equivalent or a pharmaceutically acceptable cation, in which case the rest of the molecule is negatively charged. U.S. Pat. No. 5,294,430 to Borch et al., incorporated herein by this reference, discloses additional dithiocarbamates for treatment of myelosuppression. In general, these are compounds of Formula (D-I):

(D-I)

wherein:
(i) $R^1$ and $R^2$ are the same or different $C_1$-$C_6$ alkyl groups, $C_3$-$C_6$ cycloalkyl groups, or $C_5$-$C_6$ heterocycloalkyl groups; or
(ii) one of $R^1$ and $R^2$, but not both, can be H; or
(iii) $R^1$ and $R^2$ taken together with the nitrogen atom can be a 5-membered or 6-membered N-heterocyclic ring which is aliphatic or aliphatic interrupted by a ring oxygen or a second ring nitrogen; and
(iv) M is hydrogen or one equivalent of a pharmaceutically acceptable cation, in which case the rest of the molecule is negatively charged; or
(v) M is a moiety of Formula (D-II):

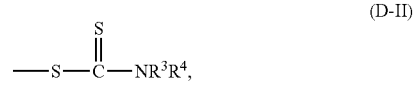

(D-II)

wherein $R^3$ and $R^4$ are defined in the same manner as $R^1$ and $R^2$. Where the group defined by Formula (D-I) is an anion, the cation can be an ammonium cation or can be derived from a monovalent or divalent metal such as an alkali metal or an alkaline earth metal, such as Na$^+$, K$^+$, or Zn$^{+2}$. In the case of the dithiocarbamic acids, the group defined by Formula (D-I) is linked to an ionizable hydrogen atom; typically, the hydrogen atom will dissociate at a pH above about 5.0. Among dithiocarbamates that can be used are: N-methyl, N-ethyldithiocarbamates, hexamethylenedithiocarbamic acid, sodium di(β-hydroxyethyl)dithiocarbamate, various dipropyl, dibutyl and diamyl dithiocarbamates, sodium N-methyl, N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, α-furfuryl dithiocarbamates and imidazoline dithiocarbamates. Another alternative is a compound where $R^1$ of Formula (D-I) is a hydroxy-substituted or, preferably, a (bis to penta) polyhydroxy-substituted lower alkyl group having up to 6 carbon atoms. For example, $R^1$ can be $HO-CH_2-CHOH-CHOH-CHOH-CHOH-CH_2-$. In such compounds, $R^2$ can be H or lower alkyl (unsubstituted or substituted with one or more hydroxyl groups). Steric problems can be minimized when $R^2$ is H, methyl, or ethyl. Accordingly, a particularly preferred compound of this type is an N-methyl-glucamine dithiocarbamate salt, the most preferred cations of these salts being sodium or potassium. Other preferred dithiocarbamates include the alkali or alkaline earth metal salts wherein the anion is di-n-butyldithiocarbamate, di-n-propyldithiocarbamate, pentamethylenedithiocarbamate, or tetramethylene dithiocarbamate.

When the improvement is made by pharmacokinetic/pharmacodynamic monitoring, the pharmacokinetic/pharmacodynamic monitoring can be, but is not limited to a method selected from the group consisting of:
(a) multiple determinations of blood plasma levels; and
(b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

When the improvement is made by drug combination, the drug combination can be, but is not limited to, a drug combination selected from the group consisting of:
(a) use with fraudulent nucleosides;
(b) use with fraudulent nucleotides;
(c) use with thymidylate synthetase inhibitors;
(d) use with signal transduction inhibitors;
(e) use with cisplatin or platinum analogs;
(f) use with alkylating agents;
(g) use with anti-tubulin agents;
(h) use with antimetabolites;
(i) use with berberine;
(j) use with apigenin;
(k) use with colchicine or an analog thereof;
(l) use with genistein;
(m) use with etoposide;
(n) use with cytarabine;
(o) use with camptothecins;
(p) use with vinca alkaloids;
(q) use with topoisomerase inhibitors;
(r) use with 5-fluorouracil;
(s) use with curcumin;
(t) use with NF-κB inhibitors;
(u) use with rosmarinic acid;
(v) use with mitoguazone;
(w) use with meisoindigo;
(x) use with imatinib;
(y) use with dasatinib;
(z) use with nilotinib;
(aa) use with epigenetic modulators;
(ab) use with transcription factor inhibitors;
(ac) use with taxol;
(ad) use with homoharringtonine;
(ae) use with pyridoxal;
(af) use with spirogermanium;
(ag) use with caffeine;
(ah) use with nicotinamide;
(ai) use with methylglyoxalbisguanylhydrazone;
(aj) use with Rho kinase inhibitors;
(ak) use with 1,2,4-benzotriazine oxides;
(al) use with an alkylglycerol;
(am) use with an inhibitor of a Mer, Ax1, or Tyro-3 receptor kinase;
(an) use with an inhibitor of ATR kinase;
(ao) use with a modulator of Fms kinase, Kit kinase, MAP4K4 kinase, TrkA kinase, or TrkB kinase;
(ap) use with endoxifen;
(aq) use with a mTOR inhibitor;
(ar) use with an inhibitor of Mnk1a kinase, Mkn1b kinase, Mnk2a kinase, or Mnk2b kinase;
(as) use with a modulator of pyruvate kinase M2;
(at) use with a modulator of phosphoinositide 3-kinases;
(au) use with a cysteine protease inhibitor;
(av) use with phenformin;
(aw) use with Sindbis virus-based vectors;
(ax) use with peptidomimetics that act as mimetics of Smac and inhibit IAPs to promote apoptosis;
(ay) use with a Raf kinase inhibitor;
(az) use with a nuclear transport modulator;
(ba) use with an acid ceramidase inhibitor and a choline kinase inhibitor;
(bb) use with tyrosine kinase inhibitors;
(bc) use with anti-CS1 antibodies;
(bd) use with inhibitors of protein kinase CK2;
(be) use with anti-guanylyl cyclase C (GCC) antibodies;
(bf) use with histone deacetylase inhibitors;
(bg) use with cannabinoids;
(bh) use with glucagon-like peptide-1 (GLP-1) receptor agonists;
(bi) use with inhibitors of Bcl-2 or Bcl-xL;
(bj) use with Stat3 pathway inhibitors;
(bk) use with inhibitors of polo-like kinase 1 (Plk1);
(bl) use with GBPAR1 activators;
(bm) use with modulators of serine-threonine protein kinase and poly(ADP-ribose) polymerase (PARP) activity;
(bn) use with taxanes;
(bo) use with inhibitors of dihydrofolate reductase;
(bp) use with inhibitors of aromatase;
(bq) use with benzimidazole-based anti-neoplastic agents;
(br) use with an O6-methylguanine-DNA-methyltransferase (MGMT) inhibitor;
(bs) use with CCR9 inhibitors;
(bt) use with acid sphingomyelinase inhibitors;
(bu) use with peptidomimetic macrocycles;
(bv) use with cholanic acid amides;
(bw) use with substituted oxazaphosphorines;
(bx) use with anti-TWEAK receptor antibodies;
(by) use with an ErbB3 binding protein;
(bz) use with a glutathione S-transferase-activated anti-neoplastic compound;
(ca) use with substituted phosphorodiamidates;
(cb) use with inhibitors of MEKK protein kinase;
(cc) use with COX-2 inhibitors;
(ce) use with cimetidine and a cysteine derivative;
(cf) use with anti-IL-6 receptor antibody;

(cg) use with an antioxidant;
(ch) use with an isoxazole inhibitor of tubulin polymerization;
(ci) use with PARP inhibitors;
(cj) use with Aurora protein kinase inhibitors;
(ck) use with peptides binding to prostate-specific membrane antigen;
(cl) use with CD19 binding agents;
(cm) use with benzodiazepines;
(cn) use with Toll-like receptor (TLR) agonists;
(co) use with bridged bicyclic sulfamides;
(cp) use with inhibitors of epidermal growth factor receptor kinase;
(cq) use with a ribonuclease of the T2 family having actin-binding activity;
(cr) use with myrsinoic acid A or an analog thereof;
(cs) use with inhibitors of a cyclin-dependent kinase;
(ct) use with inhibitors of the interaction between p53 and MDM2;
(cu) use with inhibitors of the receptor tyrosine kinase MET;
(cv) use with largazole or largazole analogs;
(cw) use with inhibitors of AKT protein kinase;
(cx) use with 2'-fluoro-5-methyl-β-L-arabinofuranosyluridine or L-deoxythymidine;
(cy) use with HSP90 modulators;
(cz) use with inhibitors of JAK kinases;
(da) use with inhibitors of PDK1 protein kinase;
(db) use with PDE4 inhibitors;
(de) use with inhibitors of proto-oncogene c-Met tyrosine kinase;
(df) use with inhibitors of indoleamine 2,3-dioxygenase;
(dg) use with agents that inhibit expression of ATDC (TRIM29);
(dh) use with proteomimetic inhibitors of the interaction of nuclear receptor with coactivator peptides;
(di) use with antagonists of XIAP family proteins;
(dj) use with tumor-targeted superantigens;
(dk) use with inhibitors of Pim kinases;
(dl) use with inhibitors of CHK1 or CHK2 kinases;
(dm) use with inhibitors of angiopoietin-like 4 protein;
(dn) use with Smo antagonists;
(do) use with nicotinic acetylcholine receptor antagonists;
(dp) use with farnesyl protein transferase inhibitors;
(dq) use with adenosine A3 receptor antagonists.
(dr) use with BTK inhibitors;
(ds) use with FLT-3 inhibitors;
(dt) use with cancer vaccines;
(du) use with biologics;
(dv) use with anti-nausea therapeutic agents;
(dw) use with cyclophosphamide;
(dx) use with doxorubicin;
(dy) use with vincristine (including liposomal formulations);
(dz) use with prednisone (including delayed release formulations);
(ea) use with bleomycin;
(eb) use with dacarbazine;
(ec) use with bendamustine hydrochloride;
(ed) use with alemtuzumab;
(ee) use with ofatumumab;
(ef) use with obinutuzumab;
(eg) use with lenalidomide;
(eh) use with vorinostat;
(ei) use with pralatrexate;
(ej) use with panobinostat;
(ek) use with brentuximab vedotin;
(el) use with omecetaxine;
(em) use with stem cell therapies;
(en) use with cyclin-dependent kinase inhibitors such as substituted pyrazolo[1,5-a]pyrimidines;
(eo) use with 4-(4-methylpiperazin-1-ylmethyl)-N-[4-methyl-3-(4-pyridin-3-yl)pyrimidin-2-ylamino)phenyl]-benzamide;
(ep) use with CXCR4 inhibitors; and
(eq) use with tryptamicidin.

Topoisomerase inhibitors include, but are not limited to, irinotecan, topotecan, camptothecin, lamellarin D, amsacrine, etoposide, etoposide phosphate, teniposide, doxorubicin, and 4-[2-(3,5-dioxo-1-piperazinyl)-1-methylpropyl]piperazine-2,6-dione (ICRF-193).

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Colchicine is a tricyclic alkaloid that exerts its activity by binding to the protein tubulin. Analogs of colchicine include, but are not limited to, cholchiceinamide, N-desacetylthiocolchicine, demecolcine, N-acetyliodocolchinol, trimethylcolchicinie acid (TMCA) methyl ether, N-acetylcolchinol, TMCA ethyl ether, isocolchicine, isocolchiceinamide, iso-TMCA methyl ether, colchiceine, TMCA, N-benzoyl TMCA, colchicosamide, colchicoside, colchinol and colchinoic acid (M. H. Zweig & C. F. Chignell, "Interaction of Some Colchicine Analogs, Vinblastine and Podophyllotoxin with Rat Brain Microtubule Protein," *Biochem. Pharmacol.* 22: 2141-2150 (1973) and B. Yang et al., "Syntheses and Biological Evaluation of Ring C-Modified Colchicine Analogs," *Bioorg. Med. Chem. Lett.* 20: 3831-3833 (2010)), both of which are incorporated herein by this reference.

Genistein is an isoflavone with the systemic name 5,7-dihydroxy-3-(4-hydroxyphenyl)chromen-4-one. Genistein has a number of biological activities, including activation of PPARs, inhibition of several tyrosine kinases, inhibition of topoisomerase, antioxidative activity, activation of Nrf2 antioxidative response, activation of estrogen receptor β, and inhibition of the mammalian hexose transporter GLUT2.

Etoposide is an anticancer agent that acts primarily as a topoisomerase II inhibitor. Etoposide forms a ternary complex with DNA and the topoisomerase II enzyme, prevents re-ligation of the DNA strands and thus induces DNA strand breakage and promotes apoptosis of the cancer cells.

Cytarabine is a nucleoside analog replacing the ribose with arabinose. It can be incorporated into DNA and also inhibits both DNA and RNA polymerases and nucleotide reductase. It is particularly useful in the treatment of acute myeloid leukemia and acute lymphocytic leukemia.

Camptothecins include, but are not limited to, camptothecin, homocamptothecin, topotecan, irinotecan, DB 67, BNP 1350, exatecan, lurtotecan, ST 1481, and CKD 602. These compounds act as topoisomerase I inhibitors and block DNA synthesis in cancer cells.

Vinca alkaloids include, but are not limited to, vinblastine, vincristine, vindesine, and vinorelbine.

Topoisomerase inhibitors include, but are not limited to, topoisomerase I inhibitors and topoisomerase II inhibitors. Topoisomerase I inhibitors include the camptothecins and lamellarin D. Topoisomerase II inhibitors include, in addition to amonafide and derivatives and analogs thereof, etoposide, teniposide, doxorubicin, daunorubicin, mitoxantrone, amsacrine, ellipticines, and aurintricarboxylic acid. A number of plant-derived naturally-occurring phenolic compounds, such as genistein, quercetin, and resveratrol, exhibit inhibitory activity toward both topoisomerase I and topoisomerase II.

5-fluorouracil is a base analog that acts as a thymidylate synthase inhibitor and thereby inhibits DNA synthesis. When deprived of a sufficient supply of thymidine, rapidly dividing cancer cells die by a process known as thymineless death.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to, bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Meisoindigo is active via several, possibly novel mechanisms of action. It has cell cycle specific effects, including arrest in G(O)/G1 for AML cell lines and G2/M arrest for HT-29 colorectal cell lines. It also stimulates apoptosis through a number of mechanisms, including the upregulation of p21 and p27 and the downregulation of Bcl-2 in primary AML cells, as well as upregulation of Bak and Bax in AML cells (DKO insensitive to chemotherapy), and a novel caspase-dependent pathway in K562 cells. Meisoindigo also has effects on mitochondria, but with no change in Bcl-2, Bax, and Bid protein expression. Meisoindigo also stimulates the cleavage of pro-caspase 3, 8, 9 and PARP in HL-60 myeloid cells. Meisoindigo also is directed to multiple cellular targets, which are possibly synergistic and complementary. For example, it promotes differentiation of human myeloblastic leukemic cells, accompanied by downregulation of c-myb gene expression. It also promotes inhibition of DNA and RNA synthesis in W256 cells, microtubule assembly, glycogen synthase kinase-3β (GSK-3β) (at 5-50 nM), CDK1/cyclin B, and CDK5/p25 (tau microtubule protein phosphorylation). Additionally, meisoindigo decreases β-catenin and c-myc (HL-60 cells, but not in K562), affects the Wnt pathway through inhibiting GSK-3β and downregulating β-catenin and c-myc protein expression. Meisoindigo also promotes upregulation of CD11b, promoting myeloid differentiation, and upregulation of Ahi-1 in Jurkat cells (inducing phosphorylation of c-Myb). Furthermore, meisoindigo exhibits antiangiogenic effects, including decreased VEGF protection, VCAM-1, tubule formulation in HUVEC, and ECV304 apoptosis.

Imatinib is an inhibitor of the receptor tyrosine kinase enzyme ABL and is used to treat chronic myelogenous leukemia, gastrointestinal stromal tumors, and other hyperproliferative disorders.

Dasatinib is an inhibitor of BCR/ABL and Src family tyrosine kinases and is used to treat chronic myelogenous leukemia and acute lymphoblastic leukemia.

Nilotinib is another tyrosine kinase inhibitor approved for the treatment of chronic myelogenous leukemia; it inhibits the kinases BCR/ABL, KIT, LCK, EPHA3, and a number of other kinases. The use of nilotinib is described in United States Patent Application Publication No. 2011/0028422 by Aloyz et al., incorporated herein by this reference.

Epigenetic modulators include polyamine-based epigenetic modulators, such as the polyamine-based epigenetic modulators described in S. K. Sharma et al., "Polyamine-Based Small Molecule Epigenetic Modulators," *Med. Chem. Commun.* 3: 14-21 (2012), and L. G. Wang & J. W. Chiao, "Prostate Cancer Chemopreventive Activity of Phenethyl Isothiocyanate Through Epigenetic Regulation (Review), *Int. J. Oncol.* 37: 533-539 (2010), both incorporated herein by this reference.

Transcription factor inhibitors include, but are not limited to, 1-(4-hexaphenyl)-2-propane-1-one, 3-fluoro-4-[[2-hydroxy-2-(5,5,8,8-tetramethyl-5,6,7,8,-tetrahydro-2-naphthalenyl)acetyl]amino]-benzoic acid (BMS 961), 4-[5-[8-(1-methylethyl)-4-phenyl-2-quinolinyl]-1H-pyrrolo-2-benzoic acid (ER-50891), 7-ethenyl-2-(3-fluoro-4-hydroxyphenyl)-5-benzoxazolol (ERB 041), and other compounds. Transcription factor inhibitors are described in T. Berg, "Inhibition of Transcription Factors with Small Organic Molecules," Curr. Opin. Chem. Biol. 12: 464-471 (2008), incorporated herein by this reference.

Tetrandrine has the chemical structure 6,6',7,12-tetramethoxy-2,2'-dimethyl-1β-berbaman and is a calcium channel blocker that has anti-inflammatory, immunologic, and anti-allergenic effects, as well as an anti-arrhythmic effect similar to that of quinidine. It has been isolated from *Stephania tetranda* and other Asian herbs.

VEGF inhibitors include bevacizumab (Avastin), which is a monoclonal antibody against VEGF, itraconazole, and suramin, as well as batimastat and marimastat, which are matrix metalloproteinase inhibitors, and cannabinoids and derivatives thereof.

Cancer vaccines are being developed. Typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," Crit. Rev. Oncol. Hematol. 67: 93-102 (2008), incorporated herein by this reference.

The use of methylglyoxalbisguanylhydrazone in cancer therapy has been described in D. D. Von Hoff, "MGBG: Teaching an Old Drug New Tricks," Ann. Oncol. 5: 487-493 (1994), incorporated herein by this reference.

The use of Rho kinase inhibitors, such as (R)-(+)-N-(4-pyridyl)-4-(1-aminoethyl)benzamide, ethacrynic acid, 4-[2 (2,3,4,5,6-pentafluorophenyl)acryloyl]cinnamic acid, (+)-trans-4-(1-aminoethyl)-1-(4-pyridylcarbamoyl) cyclohexane, (+)-10 trans-N-(1H-pyrrolo[2,3-b]pyridin-4-yl)-4-(1-aminoethyl)cyclohexanecarboxamide, and (R)-(+)-N-(1H-pyrrolo[2,3-b]pyridin-4-yl)-4-(1-aminoethyl) benzamide, is described in U.S. Pat. No. 6,930,115 to Fujii et al., incorporated herein by this reference.

The use of 1,2,4-benzotriazine oxides, such as 3-hydroxy-1,2,4-benzotriazine 1,4-dioxide, 3-amino-7-trifluoromethyl-1,2,4-benzotriazine 1-oxide, 3-amino-7-carbamyl-1,2,4-benzotriazine 1-oxide, 7-acetyl-3-amino-1,2,4-benzotriazine 1-oxide oxime, 3-amino-6(7)decyl-1,2,4-benzotriazine 1,4-dioxide, 1,2,4-benzotriazine dioxide, 7-chloro-3-hydroxy-1,2,4-benzotriazine 1,4-dioxide, 7-nitro-3-amino-1,2,4-benzotriazine 1,4-dioxide, 3-(3-N,N-diethylaminopropylamino)-1,2,4-benzotriazine 1,4-dioxide, 7-nitro-3-(2-N,N-diethylaminoethylamino)-1,2,4-benzotriazine 1,4-dioxide, 7-allyloxy-1,2,4-benzotriazine 1,4-dioxide, 7-(3-N-ethylacetamido-2-acetoxypropoxy) 1,2,4-benzotriazine 1,4-dioxide, 7-nitro-1,2,4-benzotriazine 1,4-dioxide. 3-propyl-1,2,4-benzotriazine 1,4-dioxide, and 3-(1-hydroxyethyl)-1,2,4-benzotriazine 1,4-dioxide, is described in U.S. Pat. No. 6,277,835 by Brown, incorporated herein by this reference.

The use of alkylglycerols is described in U.S. Pat. No. 6,121,245 to Firshein, incorporated herein by this reference.

The use of inhibitors of Mer, Ax1, or Tyro-3 receptor tyrosine kinase is described in United States Patent Application Publication No. 2012/0230991 by Graham et al., incorporated herein by this reference. These inhibitors can be antibodies, including monoclonal antibodies, or fusion proteins.

The use of inhibitors of ATR kinase is described in United States Patent Application Publication No. 2012/0177748 by Charrier et al., incorporated by these reference. These inhibitors of ATR kinase are substituted pyridine compounds such as 2-amino-N-phenyl-5-(3-pyridyl)pyridine-3-carboxamide, 5-(4-(methylsulfonyl)phenyl-3-(5-phenyl-1,3,4-oxadiazol-2-yl)pyridine-2-amine, and 5-(1-ethylsulfonyl-3,6-dihydro-2H-pyridin-4-yl)-3-(5-phenyl-1,3,4-oxadiazol-2-yl)pyridine-2-amine.

The use of compounds that modulate the activity of one or more of Fms kinase, Kit kinase, MAP4K4 kinase, TrkA kinase, or TrkB kinase is described in United States Patent Application Publication No. 2012/0165329 by Ibrahim et al., incorporated herein by this reference. These compounds include (6-methoxy-pyridin-3-ylmethyl)[5-(7H-pyrrolo[2,3-d]pyrimidin-5-ylmethyl)-pyrimidin-2-yl]-amine, (5-fluoro-2-methoxy-pyridin-3-ylmethyl)-[5-(7H-pyrrolo[2,3-d]pyrimidin-5-ylmethyl)-pyrimidin-2-y]-amine, and (5-fluoro-6-methoxy-pyridin-3-ylmethyl)-[5-(7H-pyrrolo[2,3-d]pyrimidin-5-ylmethyl)-pyrimidin-2-yl]-amine. Compounds that inhibit Trk kinases, particularly TrkA, are described in United States Patent Application Publication No. 2011/0301133 by Wu et al., incorporated herein by this reference.

The use of endoxifen is described in United States Patent Application Publication No. 2012/0164075 by Ahmad et al., incorporated herein by this reference.

The use of a mTOR inhibitor is described in United States Patent Application Publication No. 2012/0129881 by Burke et al., incorporated herein by this reference. Suitable mTOR inhibitors include, but are not limited to, 40-O-(2-hydroxyethyl)rapamycin. These mTOR inhibitors can be used together with Raf kinase inhibitors, as described in United States Patent Application Publication No. 2011/0301184 by Lane, incorporated herein by this reference. Raf kinase inhibitors are also described in United States Patent Application Publication No. 2010/0286178 by Ibrahim et al., incorporated herein by this reference; these compounds include, but are not limited to, propane-1-sulfonic acid {2,4-difluoro-3-[5-(2-methoxy-pyrimidin-5-yl)-1H-pyrrolo[2,3-b]pyridine-3-carbonyl]-phenyl}-amide, propane-1-sulfonic acid [3-(5-cyano-1H-pyrrolo[2,3-b]pyridine-3-carbonyl)-2,4-difluoro-phenyl]-amide, propane-1-sulfonic acid [3-(5-cyano-1H-pyrrolo[2,3-b]pyridine-3-carbonyl)-2-fluoro-phenyl]-amide, N-[3-(5-cyano-1H-pyrrolo[2,3-b]pyridine-3-carbonyl)-2,4-difluoro-phenyl]-2,5-difluoro-benzenesulfonamide, N-[3-(5-cyano-1H-pyrrolo[2,3-b]pyridine-3-carbonyl)-2,4-difluoro-phenyl]-3-fluoro-benzenesulfonamide, pyrrolidine-1-sulfonic acid [3-(5-cyano-1H-pyrrolo[2,3-b]pyridine-3-carbonyl)-2,4-difluoro-phenyl]-amide, and N,N-dimethylamino-sulfonic acid [3-(5-cyano-1H-pyrrolo[2,3-b]pyridine-3-carbonyl)-2,4-difluoro-phenyl]-amide. These mTOR inhibitors can also be used together with compounds that elevate pAkt levels in malignant cells, as described in United States Patent Application Publication No. 2009/0274698 by Bhagwat et al., incorporated herein by this reference. A number of compounds that elevate pAkt levels are described, including chemotherapeutic agents, analogs of rapamycin, and other agents. The use of mTOR inhibitors is also described in U.S. Pat. No. 8,268,819 to Jin et al., incorporated by this reference; these mTOR inhibitors are hexahydrooxazinopterine compounds.

The use of an inhibitor of Mnk1a kinase, Mnk1 b kinase, Mnk2a kinase, or Mnk2b kinase is described in United States Patent Application Publication No. 2012/0128686 by Austen et al., incorporated herein by this reference. These compounds include thienopyrimidines. Additional thienopyrimidine inhibitors of one or more of these kinases are described in United States Patent Application Publication No. 2011/0212103 by Heckel et al. and in United States Patent Application Publication No. 2011/0212102 by Lehmann-Lintz et al., both incorporated herein by this reference.

The use of a modulator of pyruvate kinase M2 is described in United States Patent Application Publication 2012/0122885 by Salituro et al., incorporated herein by this reference. Suitable modulators of pyruvate kinase M2 include, but are not limited to, 1-(3-chloro-5-(trifluoromethyl)pyridin-2-yl)-N-(3,5-dimethylphenyl)-1H-imidazole-5-sulfonamide; 1-(3-chloro-5-(trifluoromethyl)pyridin-2-yl)-N-(5-methoxyphenyl)-1H-imidazole-5-sulfonamide; and N-(4-methoxyphenyl)-1-(5-(trifluoromethyl)pyridine-2-yl)-H-imidazole-5-sulfonamide.

The use of a modulator of a phosphoinositide 3-kinase is described in United States Patent Application Publication No. 2012/0122838 by Ren et al., incorporated herein by this reference. Inhibitors of phosphoinositide 3-kinase are also described in United States Patent Application Publication No. 2010/0209420 by Lamb et al., incorporated herein by this reference, and in United States Patent Application Publication No. 2009/0209340 by Buhr et al., incorporated herein by this reference; these inhibitors include pyridopyrimidones. Inhibitors of phosphoinositide 3-kinase are also described in U.S. Pat. No. 8,242,104 to Blaquiere et al., incorporated herein by this reference; these inhibitors include benzoxazepines. Inhibitors of phosphoinositide 3-kinase are also described in U.S. Pat. No. 8,193,182 to Ren et al.; these inhibitors include isoquinolin-1(2H)-ones. Inhibitors of phosphoinositide 3-kinase are also described in U.S. Pat. No. 7,928,428 to Do et al., incorporated herein by this reference; these inhibitors include benzopyrans and benzoxepines.

The use of a cysteine protease inhibitor is described in United States Patent Application Publication No. 2012/0114765 by Cao et al., incorporated herein by this reference. Suitable cysteine protease inhibitors include, but are not limited to, 1-[5-(2,4-dichlorophenylsulfanyl)-4-nitro-2-thienyl]ethanone, 1-[5-(2,4-difluorophenylsulfanyl)-4-nitro-2-thienyl]ethanone, and 1-{4-nitro-5-[2-(trifluoromethyl)phenylsulfanyl]-2-thienyl}ethanone.

The use of phenformin is described in United States Patent Application Publication No. 2012/0114676 by Thompson et al., incorporated herein by this reference.

The use of Sindbis-based virus vectors is described in United States Patent Application Publication No. 2011/0318430 by Meruelo et al., incorporated herein by this reference. These vectors are capable of binding to solid tumors that express higher levels of high affinity laminin receptors.

The use of peptidomimetics that act as mimetics of Smac and inhibit IAPs to promote apoptosis is described in United States Patent Application Publication No. 2011/0305777 by Condon et al., incorporated herein by this reference.

The use of nuclear transport modulators, especially inhibitors of Crm1, is described in United States Patent Application Publication No. 2011/0275607 by Shacham et al., incorporated herein by this reference. These inhibitors of Crm1 include, but are not limited to, (Z)-3-[3-(3-chlorophenyl)[1,2,4]-triazol-1-yl]-acrylic acid ethyl ester, (E)-3-[3-(3-chlorophenyl)[1,2,4]-triazol-1-yl]-acrylic acid ethyl ester, (Z)-3-[3-(3-chlorophenyl)-[1,2,4]-triazol-1-yl]-acrylic acid isopropyl ester, (E)-3-[3-(3-chlorophenyl)-[1,2,4]-triazol-1-yl]-acrylic acid isopropyl ester, (Z)-3-[3-(3-chlorophenyl)-[1,2,4]-triazol-1-yl]-acrylic acid t-butyl ester, (Z)-3-[3-(3-chlorophenyl)-[1,2,4]-triazol-1-yl]-acrylic acid t-butyl ester, (E)-3-[3-(3-chlorophenyl)-[1,2,4]-triazol-1-yl]-N-phenyl-acrylamide, (E)-N-(2-chlorophenyl)-3-[3-(3-chlorophenyl)-[1,2,4]-triazol-1-yl]-acrylamide, (4-{(E)-3-[3-(3-chlorophenyl)[1,2,4]-triazol-1-yl]-acryloylamino}-phenyl-)-carbamic acid t-butyl ester, (E)-3-[3-(3-chlorophenyl)-[1,2,4]-triazol-1-yl]-N-(4-methoxyphenyl)-acrylamide, (E)-3-[3-(3-chlorophenyl)-[1,2,4]-triazol-1-yl]-N-methyl-N-phenyl-acrylamide, and (E)-N-(4-aminophenyl)-3-[3-(3-chlorophenyl)-[1,2,4]-triazol-1-yl]-acrylamide.

The use of tyrosine kinase inhibitors is described in United States Patent Application Publication No. 2011/0206661 by Zhang et al., which is directed to trimethoxyphenyl inhibitors of tyrosine kinase, and in United States Patent Application Publication No. 2011/0195066, which is directed to quinoline inhibitors of tyrosine kinase, both of which are incorporated herein by this reference. The use of tyrosine kinase inhibitors is also described in United States Patent Application Publication No. 2011/053968 by Zhang et al., incorporated herein by this reference, which is directed to aminopyridine inhibitors of tyrosine kinase. The use of tyrosine kinase inhibitors is also described in United States Patent Application Publication No. 2010/0291025, incorporated herein by this reference, which is directed to indazole inhibitors of tyrosine kinase. The use of tyrosine kinase inhibitors is also described in United States Patent Application Publication No. 2010/0190749 by Ren et al., incorporated herein by this reference; these tyrosine kinase inhibitors are benzoxazole compounds; compounds of this class can also inhibit mTOR and lipid kinases such as phosphoinositide 3-kinases. The use of tyrosine kinase inhibitors is also described in U.S. Pat. No. 8,242,270 by Lajeunesse et al., incorporated herein by this reference; these tyrosine kinase inhibitors are 2-aminothiazole-5-aromatic carboxamides.

The use of an acid ceramidase inhibitor and a choline kinase inhibitor is described in United States Patent Application Publication No. 2011/0256241 by Ramirez de Molina et al., incorporated herein by this reference.

The use of anti-CS1 antibodies is described in United States Patent Application Publication No. 2011/0165154 by Afar, incorporated herein by this reference.

The use of protein kinase CK2 inhibitors is described in United States Patent Application Publication No. 2011/0152240 by Haddach et al., incorporated herein by this reference. These protein kinase CK2 inhibitors include pyrazolopyrimidines. Additional protein kinase CK2 inhibitors, including tricyclic compounds, are described in United States Patent Application Publication No. 2011/0071136 by Haddach et al., incorporated herein by this reference; these protein kinase CK2 inhibitors may also inhibit Pim kinases or other kinases. Additional protein kinase CK2 inhibitors, including heterocycle-substituted lactams, are also described in United States Patent Application Publication No. 2011/0071115 by Haddach et al., incorporated herein by this reference; these protein kinase CK2 inhibitors may also inhibit Pim kinases or other kinases.

The use of anti-guanylyl cyclase C (GCC) antibodies is described in United States Patent Application Publication No. 2011/0110936 by Nam et al., incorporated herein by this reference.

The use of histone deacetylase inhibitors is described in United States Patent Application Publication No. 2011/0105474 by Thaler et al., incorporated herein by this reference. These histone deacetylase inhibitors include, but are not limited to, (E)-N-hydroxy-3-{4-[(E)-3-(4-methyl-piperazin-1-yl)-3-oxo-propenyl]-phenyl}-acrylamide; (E)-N-hydroxy-3-{3-[(E)-3-(4-methyl-piperazin-1-yl)-3-oxo-propenyl]-phenyl}-acrylamide; (E)-N-hydroxy-3-{3-[(E)-3-oxo-3-(4-phenyl-piperazin-1-yl)-propenyl]-phenyl}-acrylamide; (E)-3-[3-((E)-3-[1,4]bipiperidinyl-1'-yl-3-oxo-propenyl)-phenyl]-N-hydroxy-acrylamide; (E)-N-hydroxy-3-{3-[(E)-3-oxo-3-(cis-3,4,5-trimethyl-piperazin-1-yl)-propenyl]-phenyl}-acrylamide; (E)-3-{3-[(E)-3-((1S,4S)-5-methyl-2,5-diaza-bicyclo[2.2.1]hept-2-yl)-3-oxo-propenyl]-phenyl}-N-hydroxy-acrylamide; (E)-N-hydroxy-3-{4-[(E)-3-oxo-3-(4-phenyl-piperazin-1-yl)-propenyl]-phenyl}-acrylamide; (E)-3-[4-((E)-3-[1,4]bipiperidinyl-1'-yl-3-oxo-propenyl)-phenyl]-N-hydroxy-acrylamide; (E)-N-hydroxy-3-{4-[(E)-3-oxo-3-(cis-3,4,5-trimethyl-piperazin-1-yl)-propenyl]-phenyl}-acrylamide; (E)-N-hydroxy-3-{4-[(E)-3-oxo-3-((1S,4S)-5-methyl-2,5-diaza-bicyclo[2.2.1]hept-2-yl)-propenyl]-phenyl}-acrylamide; (E)-N-hydroxy-3-{5-[(E)-3-oxo-3-(4-phenyl-piperazin-1-yl)-propenyl]-pyridin-2-yl}-acrylamide; (E)-N-hydroxy-3-{5-[(E)-3-(4-methyl-piperazin-1-yl)-3-oxo-propenyl]-pyridin-2-yl}-acrylamide; (E)-N-hydroxy-3-{6-[(E)-3-oxo-3-(4-phenyl-piperazin-1-yl)-propenyl]-pyridin-2-yl}-acrylamide; (E)-N-hydroxy-3-{6-[(E)-3-(4-methyl-piperazin-1-yl)-3-oxo-propenyl]-pyridin-2-yl}-acrylamide; (E)-3-(6-{(E)-3-[4-(3-chloro-phenyl)-piperazin-1-yl]-3-oxo-propenyl}-pyridin-2-yl)-N-hydroxy-acrylamide; (E)-3-{6-[(E)-3-(4-benzoyl-piperazin-1-yl)-3-oxo-propenyl]-pyridin-2-yl}-N-hydroxy-acrylamide hydrochloride; (E)-3-(6-{(E)-3-[4-(2-chloro-phenyl)-piperazin-1-yl]-3-oxo-propenyl}-pyridin-2-yl)-N-hydroxy-acrylamide hydrochloride; (E)-N-hydroxy-3-{6-[(E)-3-oxo-3-(4-phenyl-piperidin-1-yl)-propenyl]-pyridin-2-yl}-acrylamide hydrochloride; (E)-N-hydroxy-3-{6-[(E)-3-oxo-3-(4-pyrimidin-2-yl-piperazin-1-yl)-propenyl]-pyridin-2-yl}-acrylamide hydrochloride; (E)-3-(6-{(E)-3-[4-(4-chloro-phenyl)-piperazin-1-yl]-3-oxo-propenyl}-pyridin-2-yl)-N-hydroxy-acrylamide hydrochloride; and (E)-3-{6-[(E)-3-(4-benzyl-piperazin-1-yl)-3-oxo-propenyl]-pyridin-2-yl}-N-hydroxy-acrylamide hydrochloride. Additional histone deacetylase inhibitors, including spirocyclic derivatives, are described in United States Patent Application Publication No. 2011/039840 by Varasi et al., incorporated herein by this reference. Prodrugs of histone deacetylase inhibitors are described in U.S. Pat. No. 8,227,636 to Miller et al., incorporated herein by this reference. Histone deacetylase inhibitors are described in U.S. Pat. No. 8,222,451 to Kozikowski et al., incorporated herein by this reference. Histone deacetylase inhibitors, including disubstituted aniline compounds, are also described in U.S. Pat. No. 8,119,685 to Heidebrecht et al., incorporated herein by this reference. Histone deacetylase inhibitors, including aryl-fused spirocyclic compounds, are also described in U.S. Pat. No. 8,119,852 to Hamblett et al., incorporated herein by this reference.

The use of cannabinoids is disclosed in United States Patent Application Publication No. 2011/0086113 by Velasco Diez et al., incorporated herein by this reference. Suitable cannabinoids include, but are not limited to, tetrahydrocannabinol and cannabidiol.

The use of glucagon-like peptide-1 (GLP-1) receptor agonists is described in United States Patent Application Publication No. 2011/0046071 by Karasik et al., incorporated herein by this reference. A suitable GLP-1 receptor agonist is exendin-4.

The use of inhibitors of anti-apoptotic proteins Bcl-2 or Bcl-xL is described in United States Patent Application Publication No. 2011/0021440 by Martin et al., incorporated herein by this reference.

The use of Stat3 pathway inhibitors is described in United States Patent Application Publication No. 2010/0310503 by Li et al., incorporated herein by this reference. These Stat3 pathway inhibitors include, but are not limited to, 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, and 2-ethyl-naphtho[2,3-b]furan-4,9-dione.

The use of inhibitors of polo-like kinase 1 (Plk1) is described in United States Patent Application Publication No. 2010/0278833 by Stengel et al., incorporated herein by this reference. These inhibitors include, but are not limited to, thiophene-imidazopyridines, including, but not limited to, 5-(6-chloro-1H-imidazo[4,5-c]pyridin-1-yl)-3-{[2-(trifluoromethyl)benzyl]oxy}thiophene-2-carboxamide, 5-(1H-imidazo[4,5-c]pyridin-1-yl)-3-{[2-(trifluoromethyl)benzyl]oxy}thiophene-2-carboxamide, 5-(3H-imidazo[4,5-c]pyridin-3-yl)-3-{[2-(trifluoromethyl)benzyl]oxy}thiophene-2-carboxamide, 1-(5-carbamoyl-4-{[2-(trifluoromethyl)benzyl]oxy}-2-thienyl)-N-(2-methoxyethyl)-1H-imidazo[4,5-c]pyridine-6-carboxamide, 1-(5-carbamoyl-4-{[2-(trifluoromethyl)benzyl]oxy}-2-thienyl)-N-(2-morpholin-4-ylethyl)-1H-imidazo[4,5-c]pyridine-6-carboxamide, 5-{6-[diethylamino)methyl]-1H-imidazo[4,5-c]pyridin-1-yl}-3-{[2-(trifluoromethyl)benzyl]oxy}thiophene-2-carboxamide, 5-{6-[(cyclopropylamino)methyl]-1H-imidazo[4,5-c]pyridin-1-yl}-3-{[2-(trifluoromethyl)benzyl]oxy}thiophene-2-carboxamide, 5-{6-[(4-methylpiperazin-1-yl)methyl]-1H-imidazo[4,5-c]pyridin-1-yl}-3-{[2-(trifluoromethyl)benzyl]oxy}thiophene-2-carboxamide, and 5-[6-(hydroxymethyl)-1H-imidazo[4,5-c]pyridin-1-yl]-3-{[2-(trifluoromethyl)benzyl]oxy}thiophene-2-carboxamide.

The use of GBPAR1 activators is described in United States Patent Application Publication No. 2010/0261758 by Arista et al., incorporated herein by this reference. These GBPAR1 activators include, but are not limited to, heterocyclic amides. These compounds include, but are not limited to, N-(3,5-dichlorophenyl)-3-methyl-N-naphthalen-2-ylmethyl-isonicotinamide, (3,5-dichlorophenyl)-N-(2-methoxybenzyl)-3-methyl-isonicotinamide, 3-methyl-N-phenyl-N-pyridin-3-ylmethyl-isonicotinamide, N-naphthalen-2-ylmethyl-1-oxy-N-phenyl-isonicotinamide, N-(3,5-dichlorophenyl)-3-methyl-N-(2-trifluoromethoxybenzyl)-isonicotinamide, 4-methyl-oxazole-5-carboxylic acid benzyl-phenylamide, N-benzyl-N-phenylisonicotinamide, N-benzyl-N-p-tolylisonicotinamide, N-benzyl-2-fluoro-N-phenylisonicotinamide, N-benzyl-3,5-dichloro-N-phenyl-isonicotinamide, N-benzyl-2-chloro-N-phenyl-isonicotinamide, N-benzyl-2-chloro-6-methyl-N-phenyl-isonicotinamide, N-benzyl-3-methyl-N-phenyl-isonicotinamide, N-benzyl-3-chloro-N-phenyl-isonicotinamide, N-benzyl-2,5-dichloro-N-phenyl-isonicotinamide, N-benzyl-2-methyl-N-phenyl-isonicotinamide, N-benzyl-2-cyano-N-phenyl-isonicotinamide, N-benzyl-N-phenethyl-isonicotinamide, N-benzyl-N-(2-fluoromethoxy-phenyl)-isonicotinamide, and N-benzyl-N-(4-chlorophenyl)-isonicotinamide. Additional GBPAR1 activators are described in United States Patent Application Publication No. 2010/0048579 by Arista, incorporated herein by this reference, including pyridazine, pyridine, and pyrane derivatives.

The use of modulators of serine-threonine protein kinase and poly(ADP-ribose) polymerase (PARP) activity is described in United States Patent Application Publication No. 2009/0105233 by Chua et al. and in United States Patent Application Publication No. 2010/0173013 by Drygin et al., both incorporated herein by this reference.

The use of taxanes is described in United States Patent Application Publication No. 2010/0166872 by Singh et al., incorporated herein by this reference.

The use of inhibitors of dihydrofolate reductase is described in United States Patent Application Publication No. 2010/0150896 by Gant et al., incorporated herein by this reference. These inhibitors of dihydrofolate reductase include, but are not limited to, diaminoquinazolines.

The use of inhibitors of aromatase is described in United States Patent Application Publication No. 2010/0111901 by Gant et al., incorporated herein by this reference. These inhibitors of aromatase include, but are not limited to, triazoles.

The use of benzimidazole-based anti-neoplastic agents is described in United States Patent Application Publication No. 2010/0098691 by Goh et al., incorporated herein by this reference.

The use of $O^6$-methylguanine-DNA-methyltransferase (MGMT) inhibitors is described in United States Patent Application 2010/0093647 by Liu et al., incorporated herein by this reference. Suitable MGMT inhibitors include, but are not limited to, $O^6$-benzylguanine, $O^6$-2-fluoropyridinylmethylguanine, $O^6$-3-iodobenzyl guanine, $O^6$-4-bromophenylguanine, $O^6$-5-iodophenylguanine $O^6$-benzyl-8-oxoguanine, $O^6$-(p-chlorobenzyl)guanine, $O^6$-(p-methylbenzyl)guanine, $O^6$-(p-bromobenzyl)guanine, $O^6$-(p-isopropylbenzyl)guanine, $O^6$-(3,5-dimethylbenzyl)guanine, $O^6$-(p-n-butylbenzyl)guanine, $O^6$-(p-hydroxymethybenzyl)guanine, $O^6$-benzylhypoxanthine, $N^2$-acetyl-$O^6$-benzylguanine, $N^2$-acetyl-$O^6$-benzyl-8-oxo-guanine, 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, $O^6$-benzyl-7,8-dihydro-8-oxoguanine, 2,4,5-triamino-6-benzyloxyprimidine, $O^6$-benzyl-9-[(3-oxo-5α-androstan-17β-yloxycarbonylmethyl]guanine, $O^6$-benzyl-9-[(3-oxo-4-androsten-17β-yloxycarbonyl)methyl(guanine, 8-amino-$O^6$-benzylguanine (8-amino-BG), 2,4-diamino-6-benzyloxy-5-nitrosopyrimidine, 2,4-diamino-6-benzyloxy-5-nitropyrimidine, and 2-amino-4-benzyloxy-5-nitropyrimidine.

The use of CCR9 inhibitors is described in United States Patent Application Publication No. 2010/0075963 by Lehr et al., incorporated herein by this reference. These CCR9 inhibitors include, but are not limited to, benzylsulfonylindoles.

The use of acid sphingomyelinase inhibitors is described in United States Patent Application Publication No. 2010/0022482 by Baumann et al., incorporated herein by this reference. Typically, these compounds are biphenyl derivatives.

The use of peptidomimetic macrocycles is described in United States Patent Application Publication No. 2009/0275519 by Nash et al., incorporated herein by this reference.

The use of cholanic acid amides is described in United States Patent Application Publication No. 2009/0258847 by Schreiner et al., incorporated herein by this reference. These cholanic acid amides include, but are not limited to, substituted 4-(3-hydroxy-10,13-hydroxymethyl-hexadecahydrocyclopenta(a)-phenanthren-17-yl)pentanoic acid amides.

The use of substituted oxazaphosphorines is described in United States Patent Application Publication No. 2009/0202540, incorporated herein by this reference.

The use of anti-TWEAK receptor antibodies is described in United States Patent Application Publication No. 2009/0074762 by Culp, incorporated herein by this reference. The TWEAK receptor is a member of the tumor necrosis receptor superfamily and is expressed on the surface of cancer cells in a number of solid tumors.

The use of ErbB3 binding protein is described in United States Patent Application Publication No. 2008/0269133 by Zhang et al., incorporated herein by this reference.

The use of a glutathione S-transferase-activated (GST-activated) anti-neoplastic compound is described in United States Patent Application Publication No. 2008/0166428 by Brown et al., incorporated herein by this reference. A preferred GST-activated anti-neoplastic compound is canfosfamide.

The use of substituted phosphorodiamidates is described in United States Patent Application Publication No. 2008/0125398 by Ma et al., incorporated herein by this reference, which describes 2-{[2-(substituted amino)ethyl]sulfonyl}ethyl N,N,N',N'-tetrakis(2-chloroethyl)-phosphorodiamidates, and in United States Patent Application Publication No. 2008/0125397 by Lui et al., incorporated herein by this reference, which describes 2-({2-oxo-2-[(pyridin-3-ylmethyl)amino]ethyl}sulfonyl)ethyl N,N,N',N'-tetrakis(2-chloroethyl)phosphorodiamidate. The use of substituted phosphorodiamidates is also described in United States Patent Application Publication No. 2008/0039429 by Allen et al., incorporated herein by this reference, which describes sulfonylethyl and thioethyl phosphorodiamidates.

The use of inhibitors of MEKK protein kinase is described in United States Patent Application Publication No. 2006/0100226 by Sikorski et al., incorporated herein by this reference. These inhibitors include, but are not limited to, 2-thiopyrimidinones, such as 2-[3-(3,4-dichloro-benzylamino)-benzylsulfanyl]-4-(3-methoxy-phenyl)-6-oxo-1,6-dihydro-pyrimidine-5-carbonitrile, 2-[3-(3,4-dichloro-benzylamino)-benzylsulfanyl]-4-(3,4-dimethoxy-phenyl)-6-oxo-1,6-dihydro-pyrimidine-5-carbonitrile, and 2-[3-(3,4-dichloro-benzylamino)-benzylsulfanyl-4-(4-methoxy-3-thiophen-2-yl-phenyl)-6-oxo-1,6-dihydro-pyrimidine-5-carbonitrile.

The use of COX-2 inhibitors is described in United States Patent Application Publication No. 2004/0072889 by Masferrer et al., incorporated herein by this reference. Suitable COX-2 inhibitors include, but are not limited to, celecoxib, parecoxib, deracoxib, rofecoxib, etoricoxib, valdecoxib, and meloxicam.

The use of cimetidine and N-acetylcysteine is described in United States Patent Application Publication No. 2003/0158118 by Weidner, incorporated herein by this reference. Derivatives of cimetidine or N-acetylcysteine can also be used.

The use of an anti-IL-6 receptor antibody is described in United States Patent Application Publication No. 2002/0131967 by Nakamura et al., incorporated herein by this reference. The antibody can be a humanized antibody.

The use of an antioxidant is described in United States Patent Application Publication No. 2001/0049349 by Chinery et al., incorporated herein by this reference. Suitable antioxidants include, but are not limited to, pyrrolidinedithiocarbamate, probucol (4,4'-(isopropylidenedithio)bis(2,6-di-t-butylphenol), vitamin C, vitamin E, and 6-hydroxy-2,5,7,8-tetramethylchroman-2-carboxylic acid.

The use of an isoxazole inhibitor of tubulin polymerization is described in U.S. Pat. No. 8,269,017 by Sun et al., incorporated herein by this reference. Suitable isoxazole inhibitors of tubulin polymerization include, but are not limited to, 2-amino-N-(2-methoxy-5-[5-(3,4,5-trimethoxyphenyl)-isoxazol-4-ylyphenyl)acetamide hydrochloride; 2-amino-3-hydroxy-N-(2-methoxy-5-[5-(3,4,5-trimethoxyphenyl)isoxazol-4-yl)-phenyl)propanamide hydrochloride; 2-amino-N-(2-methoxy-5-[5-(3,4,5-trimethoxyphenyl) isoxazol-4-ylphenyl)propanamide; 2-amino-N-(2-methoxy-5-[5-(3,4,5-trimethoxyphenyl)-isoxazol-4-ylyphenyl)-4-(methylthio)butanamide hydrochloride; 2-amino-N-(2-methoxy-5-[5-(3,4,5-trimethoxyphenyl)-isoxazol-4-ylphenyl)butanamide; 2-amino-N-(2-methoxy-5-[5-(3,4,5-trimethoxyphenyl)-isoxazol-4-ylyphenyl)-3-phenylpropanamide hydrochloride; 2-amino-N-(2-methoxy-5-[5-(3,4,5-trimethoxyphenyl)-isoxazol-4-ylyphenyl)-4-methylpentanamide hydrochloride; 2-amino-N-(2-methoxy-5-[5-(3,4,5-trimethoxy-phenyl)-isoxazol-4-ylphenyl)-3-(4-methoxyphenyl)propanamide hydrochloride; 1-{2-methoxy-5-[5-(3,4,5-trimethoxy-phenyl)-isoxazol-4-yl]-phenylcarbamoyl}-2-methyl-propyl-ammonium chloride; 1-{2-methoxy-5-[5-(3,4,5-trimethoxyphenyl)-isoxazol-4-yl]-phenylcarbamoyl}-2-methyl-butyl-ammonium chloride; 2-hydroxy-1-{2-methoxy-5-[5-(3,4,5-trimethoxyphenyl)-isoxazol-4-yl]-phenylcarbamoyl}-propyl-ammonium chloride; 2-(4-hydroxy-phenyl)-1-{2-methoxy-5-[5-(3,4,5-trimethoxyphenyl)-isoxazol-4-yl]-phenylcarbamoyl}-ethyl-ammonium chloride; C-{2-methoxy-5-[5-(3,4,5-trimethoxyphenyl)-isoxazol-4-yl]-phenylcarbamoyl}-C-phenyl-methyl-ammonium chloride; 2-(1H-indol-2-yl)-1-{2-methoxy-5-[5-(3,4,5-trimethoxyphenyl)-isoxazol-4-yl]-phenylcarbamoyl}-ethyl-ammonium chloride; 2-benzofuran-2-yl-1-{2-methoxy-5-[5-(3,4,5-trimethoxyphenyl)-isoxazol-4-yl]-phenylcarbamoyl}-ethyl-ammonium chloride; 2-carboxyl-1-{2-methoxy-5-[5-(3,4,5-trimethoxyphenyl)-isoxazol-4-yl]-phenylcarbamoyl}-ethyl-ammonium chloride; 3-carboxyl-1-{2-methoxy-5-[5-(3,4,5-trimethoxyphenyl)-isoxazol-4-yl]-phenylcarbamoyl}-propyl-ammonium chloride; 3-carbamoyl-1-{2-methoxy-5-[5-(3,4,5-trimethoxyphenyl)-isoxazol-4-yl]-phenylcarbamoyl}-propyl-ammonium chloride; 2-carbamoyl-1-{2-methoxy-5-[5-(3,4,5-trimethoxyphenyl)-isoxazol-4-yl]-phenylcarbamoyl}-ethyl-ammonium chloride; and 2-(3H-imidazol-4-yl)-1-{2-methoxy-5-[5-(3,4,5-trimethoxyphenyl)-isoxazol-4-yl]-phenylcarbamoyl}-ethyl-ammonium chloride.

The use of pyridazinone PARP inhibitors is described in U.S. Pat. No. 8,268,827 by Branca et al., incorporated herein by this reference. Pyridazinone PARP inhibitors include, but are not limited to, 6-{4-fluoro-3-[(3-oxo-4-phenylpiperazin-1-yl)carbonyl]benzyl}-4,5-dimethyl-3-oxo-2,3-dihydropyridazin-1-ium trifluoroacetate; 6-{3-[(4-cyclohexyl-3-oxopiperazin-1-yl)carbonyl]-4-fluorobenzyl}-4,5-dimethyl-3-oxo-2,3-dihydropyridazin-1-ium trifluoroacetate; 6-{3-[(4-cyclopentyl-3-oxopiperazin-1-yl)carbonyl]-4-fluorobenzyl}-4,5-dimethylpyridazin-3(2H)-one; 6-{4-fluoro-3-[(3-oxo-4-phenylpiperazin-1-yl)carbonyl]benzyl}-4,5-dimethylpyridazin-3(2H)-one hydrochloride; 4-ethyl-6-{4-fluoro-3-[(3-oxo-4-phenylpiperazin-1-yl)carbonyl]benzyl}pyridazin-3(2H)-one trifluoroacetate; 6-{3-[(4-cyclohexyl-3-oxopiperazin-1-yl)carbonyl]-4-fluorobenzyl}-4-ethylpyridazin-3(2H)-one trifluoroacetate; 3-{4-fluoro-3-[(4-methyl-3-oxopiperazin-1-yl)carbonyl]benzyl}-4,5-dimethyl-6-oxo-1,6-dihydropyridazin-1-ium trifluoroacetate; 3-(4-fluoro-3-{[4-(4-fluorobenzyl)-3-oxopiperazin-1-yl]carbonyl}benzyl)-4,5-dimethyl-6-oxo-1,6-dihydropyridazin-1-ium trifluoroacetate; 6-(3-{[4-(2-chlorophenyl)-3-oxopiperazin-1-yl]carbonyl}-4-fluorobenzyl)-4,5-dimethyl-3-oxo-2,3-dihydropyridazin-1-ium trifluoroacetate; 6-(3-{[4-(3-chloro-4-fluorophenyl)-3-oxopiperazin-1-yl]carbonyl}-4-fluorobenzyl)-4,5-dimethyl-3-oxo-2,3-dihydropyridazin-1-ium trifluoroacetate; and 6-(3-{[4-(3,4-difluorophenyl)-3-oxopiperazin-1-yl]carbonyl}-4-fluorobenzyl)-4,5-dimethyl-3-oxo-2,3-dihydropyridazin-1-ium trifluoroacetate. Other PARP inhibitors are described in U.S. Pat. No. 8,143,447 by Moore et al., incorporated herein by this reference; these compounds include nitrobenzamide derivatives.

The use of Aurora protein kinase inhibitors is described in U.S. Pat. No. 8,268,811 to Mortimore et al., incorporated herein by this reference. The Aurora protein kinase inhibitors include, but are not limited to, thiazoles and pyrazoles. The use of Aurora protein kinase inhibitors is also described in U.S. Pat. No. 8,129,399 to Binch et al., incorporated herein by this reference; these Aurora protein kinase inhibitors include, but are not limited to, aminopyridines.

The use of peptides binding to prostate-specific membrane antigen (PSMA) is described in U.S. Pat. No. 8,258,256 to Denmeade et al., incorporated herein by this reference.

The use of CD19 binding agents is described in U.S. Pat. No. 8,242,252 to McDonagh et al., incorporated herein by this reference. These CD19 binding agents include, but are not limited to, anti-CD19 antibodies.

The use of benzodiazepines is described in U.S. Pat. No. 8,242,109 to Glick, incorporated herein by this reference.

The use of Toll-like receptor (TLR) agonists is described in U.S. Pat. No. 8,242,106 to Howbert et al., incorporated herein by this reference. Suitable TLR agonists include, but are not limited to, (1E,4E)-2-amino-N,N-dipropyl-8-(4-(pyrrolidine-1-carbonyl)phenyl)-3H-benzo[b]azepine-4-carboxamide.

The use of bridged bicyclic sulfamides is described in U.S. Pat. No. 8,242,103 to Lewis et al., incorporated herein by this reference.

The use of inhibitors of epidermal growth factor receptor (EGFR) kinase is described in U.S. Pat. No. 8,242,080 to Kuriyan et al., incorporated herein by this reference.

The use of ribonucleases of the T2 family having actin-binding activity is described in U.S. Pat. No. 8,236,543 to Roiz et al., incorporated herein by this reference.

The use of myrsinoic acid A or an analog thereof is described in U.S. Pat. No. 8,232,318 to Lee et al., incorporated herein by this reference.

The use of an inhibitor of a cyclin-dependent kinase is described in U.S. Pat. No. 8,227,605 to Shipps et al.; these inhibitors include, but are not limited to, 2-aminothiazole-4-carboxylic amides. Use of an inhibitor of a cyclin-dependent kinase is also described in U.S. Pat. No. 7,700,773 to Mallams et al., incorporated herein by this reference; these inhibitors include, but are not limited to, 4-cyano, 4-amino, and 4-aminomethyl derivatives of pyrazolo[1,5-a]pyridine, pyrazolo[1,5-c]pyrimidine, and 2H-indazole compounds and 5-cyano, 5-amino, and 5-aminomethyl derivatives of imidazo[1,2-a]pyridine and imidazo[1,5-a]pyrazine compounds.

The use of an inhibitor of the interaction between p53 and MDM2 is described in U.S. Pat. No. 8,222,288 to Wang et al., incorporated herein by this reference.

The use of inhibitors of the receptor tyrosine kinase MET is described in U.S. Pat. No. 8,222,269 to Dinsmore et al., incorporated herein by this reference. These inhibitors of the receptor tyrosine kinase MET include, but are not limited to, 5H-benzo[4,5]cyclohepta[1,2-b]pyridine derivatives. Inhibitors of the receptor tyrosine kinase MET are also described in U.S. Pat. No. 8,207,186 to Jewell et al., incorporated herein by this reference. These compounds include, but are not limited to, benzocycloheptapyridines, including 5H-benzo[4,5]cyclohepta[1,2-b]pyridine derivatives.

The use of largazole or largazole analogs is described in U.S. Pat. No. 8,217,076 to Williams et al., incorporated herein by this reference.

The use of inhibitors of the protein kinase AKT is described in U.S. Pat. No. 8,207,169 to Furuyama et al., incorporated herein by this reference; these inhibitors include, but are not limited to, triazolopyridopyridines, including substituted [1,2,4]triazolo[4',3':1,6]pyrido[2,3-b]pyrazines.

The use of 2'-fluoro-5-methyl-β-L-arabinofuranosyluridine or L-deoxythymidine is described in U.S. Pat. No. 8,207,143 to Cheng, incorporated herein by this reference.

The use of compounds that modulate HSP90 activity is described in U.S. Pat. No. 8,188,075 to Ying et al., incorporated herein by this reference. These compounds include, but are not limited to, substituted triazoles, including 3-(2-hydroxyphenyl)-4-(naphthalen-1-yl)-5-mercaptotriazole; 3-(2,4-dihydroxyphenyl)-4-[4-(2-methoxyethoxy)-naphthalen-1-yl]-5-mercaptotriazole; 3-(2,4-dihydroxyphenyl)-4-(2-methyl-4-bromophenyl)-5-mercaptotriazole; 3-(3,4-dihydroxyphenyl)-4-(6-methoxy-naphthalen-1-yl)-5-mercaptotriazole; 3-(3,4-dihydroxyphenyl)-4-(6-ethoxy-naphthalen-1-yl)-5-mercaptotriazole; 3-(3,4-dihydroxyphenyl)-4-(6-propoxy-naphthalen-1-yl)-5-mercaptotriazole; 3-(2,4-dihydroxy-5-ethyl-phenyl)-4-(5-methoxy-naphthalen-1-yl)-5-mercaptotriazole; 3-(3,4-dihydroxyphenyl)-4-(6-isopropoxy-naphthalen-1-yl)-5-mercaptotriazole; 3-(2,4-dihydroxyphenyl)-4-(2,6-diethylphenyl)-5-mercaptotriazole; 3-(2,4-dihydroxyphenyl)-4-(2-methyl-6-ethylphenyl)-5-mercaptotriazole; 3-(2,4-dihydroxyphenyl)-4-(2,6-diisopropylphenyl)-5-mercaptotriazole; 3-(2,4-dihydroxyphenyl)-4-(1-ethyl-indol-4-yl)-5-mercaptotriazole; and 3-(2,4-dihydroxyphenyl)-4-(2,3-dihydro-benzo[1,4]dioxin-5-yl)-5-mercaptotriazole.

The use of inhibitors of a JAK kinase or PDK kinase is described in U.S. Pat. No. 8,183,245 to Guerin et al., incorporated herein by this reference. JAK kinases include JAK1, JAK2, JAK3, and TYK2. Suitable inhibitors of these classes of kinases include, but are not limited to, 5-(1-methyl-1H-pyrazol-4-yl)-3-(6-piperazin-1-ylpyrazin-2-yl)-1H-pyrrolo[2,3-b]pyridine; 5-(1-methyl-1H-pyrazol-4-yl)-3-[6-(piperidin-4-yloxy)pyrazin-2-yl]-1H-pyrrolo[2,3-b]pyridine; 3-[6-(cyclohexyloxy)pyrazin-2-yl]-5-(1-methyl-1H-pyrazol-4-yl)-1H-pyrrolo[2,3-b]pyridine; N-methyl-6-[5-(1-methyl-1H-pyrazol-4-yl)-1H-pyrrolo[2,3-b]pyridin-3-yl]-N-piperidin-4-ylpyrazin-2-amine; 3-[6-(piperidin-4-yloxy)pyrazin-2-yl]-5-(1H-pyrazol-4-yl)-1H-pyrrolo[2,3-b]pyridine; 3-{6-[(3R)-piperidin-3-yloxy]pyrazin-2-yl}-5-(1H-pyrazol-4-yl)-1H-pyrrolo[2,3-b]pyridine; and 3-{6-[(3S)-piperidin-3-yloxy]pyrazin-2-yl}-5-(1H-pyrazol-4-yl)-1H-pyrrolo[2,3-b]pyridine.

The use of inhibitors of phosphodiesterase type IV (PDE4) is described in U.S. Pat. No. 8,158,672 to Muller et al., incorporated herein by this reference. The inhibitors of PDE4 include fluoroalkoxy-substituted 1,3-dihydroisoindolyl compounds.

The use of inhibitors of c-Met proto-oncogene receptor tyrosine kinase is described in U.S. Pat. No. 8,143,251 to Zhuo et al., incorporated by this reference. These inhibitors include, but are not limited to, triazolotriazines, including [1,2,4]triazolo[4,3-b][1,2,4]triazines. Inhibitors of c-Met proto-oncogene receptor tyrosine kinase are also described in U.S. Pat. No. 8,106,197 to Cui et al., incorporated herein by this reference; these inhibitors include aminoheteroaryl compounds.

The use of inhibitors of indoleamine 2,3-dioxygenase is described in U.S. Pat. No. 8,088,803 to Combs et al., incorporated herein by this reference; these inhibitors include, but are not limited to, 1,2,5-oxadiazole derivatives.

The use of agents that inhibit ATDC (TRIM29) expression is described in U.S. Pat. No. 8,088,749 to Simeone et al., incorporated herein by this reference.

The use of proteomimetic inhibitors of the interaction of nuclear receptor with coactivator peptides is described in U.S. Pat. No. 8,084,471 to Hamilton et al., incorporated herein by this reference.

The use of antagonists of XIAP family proteins is described in U.S. Pat. No. 7,910,621 to Chen et al., incorporated herein by this reference. These antagonists include, but are not limited to, embelin.

The use of tumor-targeted superantigens is described in U.S. Pat. No. 7,763,253 to Hedlund et al., incorporated herein by this reference.

The use of inhibitors of Pim kinases is described in U.S. Pat. No. 7,750,007 to Bearss et al., incorporated herein by this reference. These inhibitors include, but are not limited to, imidazo[1,2-b]pyridazine and pyrazolo[1,5-a]pyrimidine compounds.

The use of inhibitors of CHK1 or CHK2 kinases is described in U.S. Pat. No. 7,732,436 to Tepe, incorporated herein by this reference. These inhibitors include, but are not limited to, indoloazepines and acid amine salts thereof.

The use of inhibitors of angiopoietin-like 4 protein is described in U.S. Pat. No. 7,740,846 to Gerber et al., incorporated herein by this reference. These inhibitors include, but are not limited to, antibodies, including monoclonal antibodies.

The use of inhibitors of Smo is described in U.S. Pat. No. 7,691,997 to Balkovec et al., incorporated by this reference. Smo, or Smoothened, is a mediator of signaling by hedgehog proteins. Suitable inhibitors include, but are not limited to, 5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; 2-(1,1-difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole; 2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and 2-(1-fluoro-1-methylethyl)-5-(4-{4-methyl-5-[2-(trifluoromethyl)phenyl]-4H-1,2,4-triazol-3-yl}bicyclo[2.2.2]oct-1-yl)-1,3,4-oxadiazole.

The use of nicotinic acetylcholine receptor antagonists is disclosed in U.S. Pat. No. 7,652,038 to Cooke et al., incorporated herein by this reference. Nicotinic acetylcholine receptor antagonists include, but are not limited to, mecamylamine, hexamethonium, dihydro-β-erythroidine, d-tubocurarine, pempidine, chlorisondamine, erysodine, trimethaphan camsylate, pentolinium, bungarotoxin, succinylcholine, tetraethylammonium, trimethaphan, chlorisondamine, and trimethidinium.

The use of farnesyl protein transferase inhibitors is described in U.S. Pat. No. 7,557,107 to Zhu et al., incorporated herein by this reference.

The use of adenosine A3 receptor antagonists is described in U.S. Pat. No. 6,326,390 to Leung et al., incorporated herein by this reference.

The use of Bruton's tyrosine kinase (BTK) inhibitors is described in U.S. Pat. No. 8,324,211 to Dewdney et al., incorporated herein by this reference, including 6-phenyl-imidazo[1,2-a]pyridine and 6-phenyl-imidazo[1,2-b]pyridazine derivatives; in U.S. Pat. No. 8,318,719 to Dewdney et al, incorporated herein by this reference, including 5-phenyl-1H-pyridin-2-one, 6-phenyl-2H-pyridazin-3-one, and 5-phenyl-1H-pyrazin-2-one derivatives; in U.S. Pat. No. 8,299,077 to Berthel et al., incorporated herein by this reference, including 5-phenyl-1H-pyridin-2-one, 6-phenyl-2H-pyridazin-3-one, and 5-Phenyl-1H-pyrazin-2-one derivatives; and in U.S. Pat. No. 8,236,812 to Honigberg et al., incorporated herein by this reference. BTK is a member of the Tec family of non-receptor tyrosine kinases and is a key signaling enzyme expressed in all hematopoietic cells types except T lymphocytes and natural killer cells. BTK plays an essential role in the B-cell signaling pathway linking cell surface B-cell receptor (BCR) stimulation to downstream intracellular responses. BTK is a key regulator of B-cell development, activation, signaling, and survival. In addition, BTK plays a role in a number of other hematopoetic cell signaling pathways, e.g., Toll like receptor (TLR) and cytokine receptor-mediated TNF-α production in macrophages, IgE receptor signaling in mast cells, inhibition of Fas/APO-1 apoptotic signaling in B-lineage lymphoid cells, and collagen-stimulated platelet aggregation. BTK contains a Pleckstrin homology domain (PH domain) that binds phosphatidylinositol (3,4,5)-trisphosphate (PIP3). PIP3 binding induces BTK to phosphorylate phospholipase C, which in turn results in the generation of two second messengers, inositol phosphate and diacylglycerol, which act to modulate the activity of downstream proteins during B-cell signaling. The activity and functions of BTK are described in Y.-C. Ma & X.-Y. Huang, "Identification of the Binding Site for Gqa on Its Effector Bruton's Tyrosine Kinase," Proc. Natl. Acad. Sci. USA 95: 12197-12201 (1998); T. Yasuda et al., "Cbl-b Positively Regulates Btk-Mediated Activation of Phospholipase C-γ2 in B Cells," J. Exp. Med. 196: 51-63 (2002), both incorporated herein by this reference. BTK has been shown to interact with GNAQ, PLGC2, protein kinase D1, B-cell linker, SH3BP5, caveolin 1, ARID3A, and GTF2I. Because of its role in B-cell maturation and signaling, BTK has been recently been evaluated as a target for treatment in malignancies characterized by B-cell dysregulation, including mantle cell lymphoma, chronic lymphocytic leukemia, diffuse large B-cell lymphoma, and multiple myeloma. One BTK inhibitor is ibrutinib (1-[(3R)-3-[4-amino-3-(4-phenoxyphenyl)-1H-pyrazolo[3,4-d]pyrimidin-1-yl]piperidin-1-yl]prop-2-en-1-one). Other BTK inhibitors include, but are not limited to, GDC-0834 (N-[3-[6-[[4-[(2S)-1,4-dimethyl-3-oxo-2-piperazinyl]phenyl]amino]-4,5-dihydro-4-methyl-5-oxo-2-pyrazinyl]-2-methylphenyl]-4,5,6,7-tetrahydro-Benzo[b]thiophene-2-carboxamide), AVL-292 (N-[3-[[5-fluoro-2-[[4-(2-methoxyethoxy)phenyl]amino]-4-pyrimidinyl]amino]phenyl]-2-propenamide), CNX-774 (4-(4-((4(3-acrylamidophenyl)amino)-5-fluoropyrimidin-2-yl)amino)phenoxy)-N-methylpicolinamide), CGI-560 (4-(tert-butyl)-N-(3-(8-(phenylamino)imidazo[1,2-a]pyrazin-6-yl)phenyl)benzamide), CGI-1746 (N-[3-[4,5-dihydro-4-methyl-6-[[4-(4-morpholinylcarbonyl)phenyl]amino]-5-oxo-2-pyrazinyl]-2-methylphenyl]-4-(1,1-dimethylethyl)-benzamide), HM-71224, ONO-4059 RN-486 (6-cyclopropyl-8-fluoro-2-(2-hydroxymethyl)-3-(1-methyl-5-((5-(4-methylpiperazin-1-yl)pyridine-2-yl)amino-6-oxo-1,6-dihydropyridin-3-yl)phenyl)isoquinolin-1(2H)-one) and LFM-A13 (α-cyano-β-hydroxy-β-methyl-N-(2,5-dibromophenyl) propenamide). BTK inhibitors are described in A. Akinleye et al., "Ibrutinib and Novel BTK Inhibitors in Clinical Development," J. Hematol. Oncol. 6:59 (2013); R. W. Hendricks et al., "Targeting Bruton's Tyrosine Kinase in B Cell Malignancies," Nature Rev. Cancer 14: 219-232 (2014); and O. J. D'Cruz & F. M. Uckun, "Novel Bruton's Tyrosine Kinase Inhibitors Currently in Development," Onco. Targets Ther. 6: 161-176 (2013), all of which are incorporated herein by this reference. Other BTK inhibitors are disclosed in U.S. Pat. No. 8,658,653 to Honigberg et al.; U.S. Pat. No. 8,563,563 to Honigberg et al.; U.S. Pat. No. 8,552,010 to Honigberg et al.; U.S. Pat. No. 8,501,751 to Honigberg et al.; U.S. Pat. No. 8,501,724 to Chen et al.; U.S. Pat. No. 8,497,277 to Honigberg et al.; U.S. Pat. No. 8,476,284 to Honigberg et al.; United States Patent Application Publication No. 2014/0080844 by Chen et al.; United States Patent Application Publication No. 2014/0079690 by Buggy et al.; United States Patent Application Publication No. 2014/0039186 by Honigberg et al.; United States Patent Application Publication No. 2013/0338172 by Smyth et al.; United States Patent Application Publication No. 2013/0310402 by Buggy et al.; United States Patent Application Publication No. 2013/0273030 by Buggy et al.; and United States Patent Application Publication No. 2013/0195852 by Buggy et al., all of which are incorporated herein by this reference.

FLT-3 inhibitors are described in U.S. Pat. No. 8,329,726 by Chimmanamada et al., incorporated herein by this reference. FLT-3 is also known as CD135 and is a cytokine receptor that belongs to the receptor tryrosin kinase class III. It is expressed on the surface of many hematopoietic progenitor cells. FLT-3 is frequently mutated in acute myelocytic leukemia (AML) and FLT-3 may be overexpressed in AML patients even without detectable mutations.

Biologic agents for cancer therapy, other than cancer vaccines, include, but are not limited to, interferons, interleukins, G-CSF, GM-CSF, erythropoietin, interleukin-11, monoclonal antibodies, gene therapeutic agents, bacillus Calmette-Guerin, and levamisole.

Anti-nausea therapeutic agents include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Cyclophosphamide is a nitrogen-mustard-based alkylating agent of the oxazophorine group and alkylates the $N^7$ nitrogen of guanine. It is a prodrug that is converted in vivo to its active metabolite phosphoramide mustard.

Doxorubicin is an anthracycline antibiotic that acts as a DNA intercalator.

Vincristine is a vinca alkaloid from Catharanthus roseus that is a mitotic inhibitor by virtue of its activity in binding to tubulin dimers, thus inhibiting assembly of microtubule structures. Liposomal formulations of vincristine, such as Marquibo™, have been used. Other vinca alkaloids, such as vinblastine and vinorelbin, are known in the art.

Prednisone is a glucocorticoid steroid prodrug that is converted in vivo into its active form, prednisolone. Prednisone also can be used in a delayed release formulation.

Bleomycin is a glycopeptide antibiotic produced by *Streptomyces verticillus* and works by induction of DNA strand breaks.

Dacarbazine is an antineoplastic alkylating agent that is activated in vivo.

Bendamustine hydrochloride is a nitrogen mustard alkylating agent that causes intra-strand and inter-strand cross-links in DNA.

Alemtuzumab is a humanized monoclonal antibody that binds to CD52, a protein present on the surface of mature lymphocytes.

Ofatumumab is a human monoclonal antibody that binds to CD20 and inhibits early-stage B lymphocyte activation. It binds to both the large and small loops of the CD20 protein on B cells.

Obinutuzumab is a glycoengineered Type II anti-CD20 monoclonal antibody.

Lenalidomide ((RS)-3-(4-amino-1-oxo 1,3-dihydro-2H-isoindol-2-yl)piperidine-2,6-dione) induces tumor cell apoptosis directly and inhibits bone marrow stromal cell support, and possesses anti-angiogenic and anti-osteoclastogenic effects. Lenalidomide may also act as an immunomodulator.

Vorinostat (suberoylanilide hydroxamic acid) is a histone deacetylase inhibitor.

Pralatrexate (N-(4-{1-[(2,4-diaminopteridin-6-yl)methyl] but-3-yn-1-yl}benzoyl)-L-glutamic acid) is an antifolate agent that selectively enters cells expressing reduced folate carrier type 1, a protein overexpressed in certain cancer cells, and thus interferes with folate metabolism in those cells.

Panobinostat ((2E)-N-hydroxy-3-[4-({[2-(2-methyl-1H-indol-3-yl)ethyl]amino}methyl)phenyl]acrylamide) is also a histone deacetylase inhibitor.

Brentuximab vedotin is an antibody-drug conjugate that consists of the chimeric monoclonal antibody brentuximab that targets the cell-membrane protein CD30 linked to three to five molecules of the antimitotic agent monomethyl auristatin E.

Stem-cell-based therapies for cancer are also being developed. The use of high-dose chemotherapy with hematopoietic stem-cell rescue for the treatment of multiple myeloma is described in J. A. Child et al., "High-Dose Chemotherapy with Hematopoietic Stem-Cell Rescue for Multiple Myeloma," *New Engl. J. Med.* 348: 1875-1883 (2003), incorporated herein by this reference. The use of chemotherapy together with stem-cell transplantation is described in N. Schmitz et al., "Aggressive Conventional Chemotherapy Compared with High-Dose Chemotherapy with Autologous Haemopoietic Stem-Cell Transplantation for Relapsed Chemosensitive Hodgkin's Disease: a Randomised Trial," *Lancet* 359: 2065-2071 (2002), incorporated herein by this reference.

The use of cyclin-dependent kinase inhibitors such as substituted pyrazolo[1,5-a]pyrimidines is disclosed in U.S. Pat. No. 8,580,782 to Guzi et al., incorporated herein by this reference.

The use of 4-(4-methylpiperazin-1-ylmethyl)-N-[4-methyl-3-(4-pyridin-3-yl)pyrimidin-2-ylamino)phenyl]-benzamide is disclosed in U.S. Pat. No. 8,492,383 to Panasci et al., incorporated herein by this reference.

The use of CXCR4 inhibitors is disclosed in United States Patent Application Publication No. 2013/0216531 by Jain et al., incorporated herein by this reference. CXCR4 inhibitors include, but are not limited to: 1,1'-[1,4-phenylene-bis(methylene)]-bis-1,4,8,11-tetraazacyclotetradecane (AMD-3100); Mozobil; Plerixafor; NOXA12; CTCE-9908; ALX40-4C; T22; T140; (Met-SDF-1β); T134; AMD-3465; N'-(1-Hbenzimidazol-2-ylmethyl)-N1-(5,6,7,8-tetrahydroquinoline-8-yl)-butane-1,4-diamine; CTCF-0214; CTCF-9908; CP-1221 (linear peptides, cyclic peptides, natural amino-acids, unnatural amino acids, and peptidomimetic compounds); 4F-benzoylTN24003; KRH-1120; KRH-1636; KRH-2731; polyphemusin analogue; ALX40-4C; T-140; T-140 analogs and derivatives; TN14003; TC14012; and TE14011.

The use of tryptamicidin is disclosed in United States Patent Application Publication No. 2013/0266666 by Moneo Ocana et al., incorporated herein by this reference.

In the case of vaccines, biologics, BTK inhibitors, JAK-2 inhibitors, or FLT-3 inhibitors, the substituted alkylating agent can be administered either simultaneously with the vaccine, biologic, BTK inhibitor, JAK-2 inhibitor, or FLT-3 inhibitor or subsequent to the administration of the vaccine, biologic, BTK inhibitor, JAK-2 inhibitor, or FLT-3 inhibitor.

United States Patent Application Publication No. 2010/0069458 by Atadja et al., incorporated herein by this reference, discloses the use of the following additional therapeutic agents, which can be used together with a mustard-based alkylating agent such as uracil mustard as described above:

(1) ACE inhibitors, including, but not limited to, benazepril, enazepril, captopril, enalapril, fosinopril, lisinopril, moexipril, quinapril, ramipril, perindopril and trandolapril;

(2) adenosine kinase inhibitors, including, but not limited to, 5-iodotubericidin;

(3) adrenal cortex antagonists, including, but not limited to, mitotane;

(4) AKT pathway inhibitors (protein kinase B inhibitors) including, but not limited to, deguelin and 1,5-dihydro-5-methyl-1-β-D-ribofuranosyl-1,4,5,6,8-pentaazaacenaphthylen-3-amine;

(5) angiogenesis inhibitors, including, but not limited to, fumagillin, Shikonin, Tranilast, ursolic acid; suramin; thalidomide, lenalidomide; phthalazines, including, but not limited to, 1-(4-chloroanilino)-4-(4-pyridylmethyl)phthalazine, 1-(4-methylanilino)-4-(4-pyridylmethyl)phthalazine, 1-(3-chloroanilino)-4-(4-pyridylmethyl)phthalazine, 1-anilino-4-(4-pyridylmethyl)phthalazine, 1-benzylamino-4-(4-pyridylmethyl)phthalazine, 1-(4-methoxyanilino)-4-(4-pyridylmethyl)phthalazine, 1-(3-benzyloxyanilino)-4-(4-pyridylmethyl)phthalazine, 1-(3-methoxyanilino)-4-(4-pyridylmethyl)phthalazine, 1-(2-methoxyanilino}-4-(4-pyridylmethyl)phthalazine, 1-(4-trifluoromethylanilino)-4-(4-pyridylmethyl)phthalazine, 1-(4-fluoroanilino)-4-(4-pyridylmethyl)phthalazine, 1-(3-hydroxyanilino)-4-(4-pyridylmethyl)phthalazine, 1-(4-hydroxyanilino)-4-(4-pyridylmethyl)phthalazine, 1-(3-aminoanilino)-4-(4-pyridylmethyl)phthalazine, 1-(3,4-dichloroanilino)-4-(4-pyridylmethyl)phthalazine, 1-(4-bromoanilino)-4-(4-pyridylmethyl)phthalazine, 1-(3-chloro-4-methoxyanilino)-4-(4-pyridylmethyl)phthalazine, 1-(4-cyanoanilino)-4-(4-pyridylmethyl)phthalazine, 1-(3-chloro-4-fluoroanilino)-4-(4-pyridylmethyl)phthalazine, 1-(3-methylanilino)-4-(4-pyridylmethyl)phthalazine, and other phthalazines disclosed in PCT Patent Application Publication No. WO 98/035958 by Bold et al., incorporated herein in its entirety by this reference, isoquinolines disclosed in PCT Patent Application Publication No. WO 00/09495 by Altmann et al., incorporated herein in its entirety by this reference, including 1-(3,5-dimethylanilino)-4-(pyridin-4-ylmethyl)-isoquinoline; phthalazines disclosed in PCT Patent Application Publication No. WO 00/59509 by Bold et al., incorporated herein in its entirety by this reference, including E-1-(3-methylanilino)-4-[(2-(pyridin-3-yl)vinyl]phthalazine, Z-1-(3-methylanilino)-4-[(2-(pyridin-3-yl)vinyl]phthalazine, 1-(3-methylanilino)-4-[(2-(pyridin-3-yl)ethyl]phthalazine, 1-(3-methylanilino)-4-[{2-(pyridin-4-yl)vinyl]phthalazine, 1-(4-chloro-3-trifluoromethylanilino)-4-[(2-(pyridin-3-yl)ethyl]phthalazine, 1-(4-chloroanilino)-4-[(2-(pyridin-3-yl)ethyl]phthalazine, 1-(3-chlorobenzylamino)-4-[(2-(pyridin-3-yl)ethyl]phthalazine, 1-(4-chloro-3-trifluoromethylanilino)-4-[3-(pyridin-3-yl)propyl]phthalazine, 1-(4-chloroanilino)-4-[3-(pyridin-3-yl)propyl]phthalazine, 1-(3-chloro-5-trifluoromethylanilino)-4-[3-(pyridin-3-yl)propyl]phthalazine, and 1-(4-tert-butylanilino)-4-[3-(pyridin-3-yl)propyl]phthalazine; and monoclonal antibodies;

(6) angiostatic steroids, including, but not limited to, anecortave, triamcinolone, hydrocortisone, 11α-epihydrocotisol, cortexolone, 17α-hydroxyprogesterone, corticosterone, desoxycorticosterone, testosterone, estrone, and dexamethasone;

(7) anti-androgens, including, but not limited to, nilutamide and bicalutamide;

(8) anti-estrogens, including, but not limited to, toremifene, letrozole, testolactone, anastrozole, bicalutamide, flutamide, exemestane, tamoxifen, fulvestrant, and raloxifene;

(9) anti-hypercalcemia agents, including, but not limited to, gallium (III) nitrate hydrate and pamidronate disodium;

(10) apoptosis inducers, including, but not limited to, 2-[[3-(2,3-dichlorophenoxy)propyl]amino]-ethanol, gambogic acid, embellin, and arsenic trioxide;

(11) ATI receptor antagonists, including, but not limited to, valsartan;

(12) aurora kinase inhibitors, including, but not limited to, binucleine 2;

(13) aromatase inhibitors, including, but not limited to: (a) steroids, including, but not limited to, atamestane, exemestane, and formestane; and (b) non-steroids, including, but not limited to, aminoglutethimide, roglethimide, pyridoglutethimide, trilostane, testolactone, ketoconazole, vorozole, fadrozole, anastrozole, and letrozole;

(14) bisphosphonates, including, but not limited to, etidronic acid, clodronic acid, tiludronic acid, alendronic acid, ibandronic acid, risedronic acid, and zoledronic acid;

(15) Bruton's tyrosine kinase inhibitors, including, but not limited to, terreic acid;

(16) calcineurin inhibitors, including, but not limited to, cypermethrin, deltamethrin, fenvalerate, and tyrphostin 8;

(17) CaM kinase II inhibitors, including, but not limited to, the 5-isoquinolinesulfonic acid 4-[(2S)-2-[(5-isoquinolinylsulfonyl)methylamino]-3-oxo-3-(4-phenyl-1-piperazinyl)propyl]phenyl ester, and N-[2-[[[3-(4-chlorophenyl)-2-propenyl]methyl]amino]methyl]phenyl]-N-(2-hydroxyethyl)-4-methoxy-benzenesulfonamide;

(18) CD45 tyrosine phosphatase inhibitors, including, but not limited to, [[2-(4-bromophenoxy)-5-nitrophenyl]hydroxymethyl]-phosphonic acid;

(19) CDC25 phosphatase inhibitors, including, but not limited to, 2,3-bis[(2-hydroyethyl)thio]-1,4-naphthalenedione;

(20) CHK kinase inhibitors, including, but not limited to, debromohymenialdisine;

(21) compounds targeting/decreasing a protein or lipid kinase activity; or a protein or lipid phosphatase activity; or further anti-angiogenic compounds, including, but not limited to, protein tyrosine kinase and/or serine and/or threonine kinase inhibitors or lipid kinase inhibitors, including, but not limited to:

(a) compounds targeting, decreasing or inhibiting the activity of the vascular endothelial growth factor receptors (VEGFR) or of vascular endothelial growth factor (VEGF), including, but not limited to, 7H-pyrrolo[2,3-d]pyrimidine derivatives, including: [6-[4-(4-ethyl-piperazine-1-ylmethyl)-phenyl]-7H-pyrrolo[2,3-d]pyrimidin-4-yl]-(R)-1-phenyl-ethyl-yamine (known as AEE788), BAY 43-9006; and isoquinoline compounds disclosed in PCT Patent Application Publication No. WO 00/09495, such as (4-tert-butyl-phenyl)-94-pyridin-4-ylmethyl-isoquinolin-1-yl)-amine;

(b) compounds targeting, decreasing or inhibiting the activity of the platelet-derived growth factor-receptor (PDGFR), including, but not limited to: N-phenyl-2-pyrimidine-amine derivatives, e.g., imatinib, SU101, SU6668 and GFB-111;

(c) compounds targeting, decreasing or inhibiting the activity of the fibroblast growth factor-receptor (FGFR);

(d) compounds targeting, decreasing or inhibiting the activity of the insulin-like growth factor receptor 1 (IGF-1R), including, but not limited to: the compounds disclosed in WO 02/092599 and derivatives thereof of 4-amino-5-phenyl-7-cyclobutyl-pyrrolo[2,3-d]pyrimidine derivatives;

(e) compounds targeting, decreasing or inhibiting the activity of the Trk receptor tyrosine kinase family;

(f) compounds targeting, decreasing or inhibiting the activity of the Axl receptor tyrosine kinase family;

(g) compounds targeting, decreasing or inhibiting the activity of the c-Met receptor;

(h) compounds targeting, decreasing or inhibiting the activity of the Ret receptor tyrosine kinase;

(i) compounds targeting, decreasing or inhibiting the activity of the Kit/SCFR receptor tyrosine kinase;

(j) compounds targeting, decreasing or inhibiting the activity of the C-kit receptor tyrosine kinases, including, but not limited to, imatinib;

(k) compounds targeting, decreasing or inhibiting the activity of members of the c-Abl family and their gene-fusion products, e.g., BCR-Abl kinase, such as N-phenyl-2-pyrimidine-amine derivatives, including, but not limited to: imatinib, 6-(2,6-dichlorophenyl)-2-[(4-fluoro-3-methylphenyl)amino]-8-methyl-pyrido[2,3-d]pyrimidin-7(8H)-one (PD180970), methyl-4-[N-(2',5'-dihydroxybenzyl)amino]benzoate (Tyrphostin AG957), 4-[[(2,5-dihydroxyphenyl)methyl]amino]benzoic acid tricyclo[3.3.1.13,7]dec-1-yl ester (adaphostin or NSC 680410), 6-(2,6-dichlorophenyl)-8-methyl-2-(3-methylsulfanylanilino)pyrido[2,3-d]pyrimidin-7-one (PD173955), and desatinib;

(l) compounds targeting, decreasing or inhibiting the activity of members of the protein kinase C (PKC) and Raf family of serine/threonine kinases, members of the MEK, SRC, JAK, FAK, PDK and Ras/MAPK family members, or P1(3) kinase family, or of the PI(3)-kinase-related kinase family, and/or members of the cyclin-dependent kinase family (CDK) and are especially those staurosporine derivatives disclosed in U.S. Pat. No. 5,093,330, such as, but not limited to, midostaurin; examples of further compounds include, e.g., UCN-01; safingol, sorafenib, Bryostatin 1; Perifosine; Ilmofosine; 3-[3-[2,5-Dihydro-4-(1-methyl-1H-indol-3-yl)-2,5-dioxo-1H-pyrrol-3-yl]-1H-indol-1-yl]propyl carbamimidothioic acid ester (RO 318220), 3-[(8S)-8-[(dimethylamino)methyl]-6,7,8,9-tetrahydropyrido[1,2-a]indol-10-yl]-4-(1-methyl-1H-indol-3-yl)-1H-pyrrole-2,5-dione (RO 320432), 12-(2-cyanoethyl)-6,7,12,13-tetrahydro-13-methyl-5-oxo-5H-indolo[2,3-a]pyrrolo[3,4-c]carbazole (GO 6976); Isis 3521; (S)-13-[(dimethylamino)methyl]-10,11,14,15-tetrahydro-4,9:16,21-dimetheno-1H, 13H-dibenzo[e,k]pyrrolo[3,4-h][1,4,13]oxadiazacyl clohexadecene-1,3(2H)-drone (LY333531), LY379196; isoquinoline compounds, such as those disclosed in PCT Patent Application Publication No. WO 00/09495; farnesyltransferase inhibitors, including, but not limited to, tipifarnib and lonafarnib; 2-(2-chloro-4-iodo-phenylamino)-N-cyclopropylmethoxy-3,4-difluoro-benzamide (PD184352); and QAN697, a PI3K inhibitor;

(m) compounds targeting, decreasing or inhibiting the activity of protein-tyrosine kinase, such as, but not limited to, imatinib mesylate, a tyrphostin, pyrymidylaminobenzamide and derivatives thereof; a tyrphostin is preferably a low molecular weight ($M_r$<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, Tyrphostin AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; Tyrphostin AG957, and adaphostin (4-{[(2,5-dihydroxyphenyl)methyl]amino}-benzoic acid adamantyl ester or NSC 680410);

(n) compounds targeting, decreasing or inhibiting the activity of the epidermal growth factor family of receptor tyrosine kinases (EGFR, ErbB2, ErbB3, ErbB4 as homodimers or heterodimers), such as, but not limited to, those compounds, proteins or monoclonal antibodies generically and specifically disclosed in PCT Patent Application Publication No. WO 97/02266 by Traxler et al. such as (R)-6-(4-hydroxyphenyl)-4-[(1-phenylethyl)-amino]-7H-pyrrolo-[2,3-d]pyrimidine, or in European Patent Application Publication No. EP 0564409 by Zimmermann, PCT Patent Application Publication No. WO 99/03854 by Zimmermann et al., European Patent Application Publication No. EP 0520722 by Barker et al., European Patent Application Publication No. EP 0566226 by Barker et al., European Patent Application Publication EP 0787722 by Wissner et al., European Patent Application Publication EP 0837063 by Arnold et al., U.S. Pat. No. 5,747,498 by Schnur et al., PCT Patent Application Publication WO 98/10767 by McMahon et al., PCT Patent Application Publication WO 97/30034 by Barker, PCT Patent Application Publication WO 97/49688 by Schnur, PCT Patent Application Publication WO 97/38983 by Bridges et al., PCT Patent Application Publication WO 96/30347 by Schnur et al., including, but not limited to, N-(3-ethylnylphenyl)-6,7-bis(2-methoxyethoxy)-4-quinazolinamine (CP 358774 or erlotinib), PCT Patent Application Publication WO 96/33980 by Gibson et al., including, but not limited to, N-(3-chloro-4-fluoro-phenyl)-7-methoxy-6-(3-morpholin-4-ylpropoxy)quinazolin-4-amine (gefitinib); and PCT Patent Application Publication WO 95/03283 by Barker et al., including, but not limited to, compound 6-amino-4-(3-methylphenyl-amino)-quinazoline (ZM105180); monoclonal antibodies, including, but not limited to trastuzumab and cetuximab; and other small molecule inhibitors, including, but not limited to: canertinib, pelitinib, lapatinib, and 7H-pyrrolo-[2,3-d]pyrimidine derivatives which are disclosed in PCT Patent Application Publication WO 03/013541 by Bold et al.;

(22) compounds which target, decrease or inhibit the activity of a protein or lipid phosphatase, including, but not limited to, inhibitors of phosphatase 1, phosphatase 2A, PTEN or CDC25, such as, but not limited to okadaic acid or a derivative thereof;

(23) compounds which induce cell differentiation processes, including, but not limited to, retinoic acid, α-tocopherol, γ-tocopherol, δ-tocopherol, α-tocotrienol, γ-tocotrienol, and δ-tocotrienol;

(24) cRAF kinase inhibitors, including, but not limited to, 3-(3,5-dibromo-4-hydroxybenzylidene)-5-iodo-1,3-dihydroindol-2-one and 3-(dimethylamino)-N-[3-[(4-hydroxybenzoyl)amino]-4-methylphenyl]-benzamide;

(25) cyclin dependent kinase inhibitors, including, but not limited to, N9-isopropyl-olomoucine; olomoucine; purvalanol B, roascovitine, kenpaullone, and purvalanol A;

(26) cysteine protease inhibitors, including, but not limited to, N-[(1S)-3-fluoro-2-oxo-1-(2-phenyl]ethyl)propyl]amino]-2-oxo-1-(phenylmethyl)ethyl]-4-morpholinecarboxamide;

(27) DNA intercalators, including, but not limited to, plicamycin and dactinomycin;

(28) DNA strand breakers, including, but not limited to, bleomycin;

(29) E3 ligase inhibitors, including, but not limited to, N-((3,3,3-trifluoro-2-trifluoromethyl)propionyl)sulfanilamide;

(30) EDG binders, including, but not limited to, FTY720;

(31) endocrine hormones, including, but not limited to, leuprolide and megestrol acetate;

(32) farnesyltransferase inhibitors, including, but not limited to, α-hydroxyfarnesylphosphonic acid, 2-[[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-, 1-methylethyl butanoic acid ester (2S), and manumycin A;

(33) Flk-1 kinase inhibitors, including, but not limited to, 2-cyano-3-[4-hydroxy-3,5-bis(1-methylethyl)phenyl]-N-(3-phenylpropyl)-, (2-E)-2-propenamide;

(34) Flt-3 inhibitors, including, but not limited to, N-benzoyl-staurosporine, midostaurin, and N-(2-diethylaminoethyl)-5-[(Z)-(5-fluoro-2-oxo-1H-indol-3-ylidene)methyl]-2,4-dimethyl-1H-pyrrole-3-carboxamide (sunitinib);

(35) gonadorelin agonists, including, but not limited to, abarelix, goserelin, and goserelin acetate;

(36) heparanase inhibitors, including, but not limited to, phosphomannopentaose sulfate (PI-88);

(37) histone deacetylase (HDAC) inhibitors, including, but not limited to, compounds disclosed in PCT Patent Application Publication No. WO 02/22577 by Bair et al., including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-amino-phenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate;

(38) HSP90 inhibitors, including, but not limited to: 17-allylamino, 17-demethoxygeldanamycin (17AAG); a geldanamycin derivative; other geldanamycin-related compounds; radicicol; and 5-(2,4-dihydroxy-5-isopropyl-phenyl)-4-(4-morpholin-4-ylmethyl-phenyl)-isoxazole-3-carboxylic acid ethylamide;

(39) IκBα inhibitors (IKKs), including, but not limited to, 3-[(4-methylphenyl)sulfonyl]-(2E)-2-propenenitrile;

(40) insulin receptor tyrosine kinase inhibitors, including, but not limited to, hydroxy-2-naphthalenylmethylphosphonic acid;

(41) c-Jun N-terminal kinase inhibitors, including, but not limited to, pyrazoleanthrone and epigallocatechin gallate;

(42) microtubule binding agents, including, but not limited to: vinblastine sulfate; vincristine sulfate; vindesine; vinorelbine; docetaxel; paclitaxel; discodermolides; colchicines; and epothilones and derivatives thereof, such as epothilone B or a derivative thereof;

(43) mitogen-activated protein (MAP) kinase inhibitors, including, but not limited to, N-[2-[[[3-(4-chlorophenyl)-2-propenyl]methyl]amino]methyl]phenyl]-N-(2-hydroxyethyl)-4-methoxy-benzenesulfonamide;

(44) MDM2 inhibitors, including, but not limited to, trans-4-iodo,4'-boranyl-chalcone;

(45) MEK inhibitors, including, but not limited to, bis[amino[2-aminophenyl)thio]methylene]-butanedinitrile;

(46) methionine aminopeptidase inhibitors, including, but not limited to, bengamide and derivatives thereof;

(47) MMP inhibitors, including, but not limited to: actinonin; epigallocatechin gallate; collagen peptidomimetic and non-peptidomimetic inhibitors; tetracycline derivatives such as hydroxamate, batimastat, marimastat, primomastat, TAA211, N-hydroxy-2(R)-[[(4-methoxyphenyl)sulfonyl](3-picolyl)amino]-3-methylbutanamide hydrochloride (MMI270B), and AAJ996;

(48) NGFR tyrosine kinase inhibitors, including, but not limited to, Tyrphostin AG 879;

(49) p38 MAP kinase inhibitors, including, but not limited to, 3-(dimethylamino)-N-[3-[(4-hydroxybenzoyl)amino]-4-methylphenyl]-benzamide;

(50) p56 tyrosine kinase inhibitors, including, but not limited to, 9,10-dihydro-3-hydroxy-1-methoxy-9,10-dioxo-2-anthracenecarboxaldehyde and Tyrphostin 46;

(51) PDGFR tyrosine kinase inhibitors, including, but not limited to, Tyrphostin AG 1296; Tyrphostin 9, 2-amino-4-(1H-indol-5-yl)-1,3-butadiene-1,1,3-tricarbonitrile, and imatinib;

(52) phosphatidylinositol 3-kinase inhibitors, including, but not limited to, wortmannin and quercetin dihydrate;

(53) phosphatase inhibitors, including, but not limited to, cantharidic acid, cantharidin, and (E)-N-[4-(2-carboxyethenyl)benzoyl]glycyl-L-α-glutamyl-L-leucinamide;

(54) platinum agents, including, but not limited to, carboplatin, cisplatin, oxaliplatin, satraplatin, and ZD0473;

(55) protein phosphatase inhibitors, including, but not limited to:
  (a) PP1 and PP2A inhibitors, including, but not limited to, cantharidic acid and cantharidin;
  (b) tyrosine phosphatase inhibitors, including, but not limited to, L-P-bromotetramisole oxalate, benzylphosphonic acid, and (5R)-4-hydroxy-5-(hydroxymethyl)-3-(1-oxohexadecyl)-2(5H)-furanone;

(56) PKC inhibitors, including, but not limited to, -[1-[3-(dimethylamino)propyl]-1H-indol-3-yl]-4-(1H-indol-3-yl)-1H-pyrrolo-2,5-dione, sphingosine, staurosporine, Tyrphostin 51, and hypericin;

(57) PKC delta kinase inhibitors, including, but not limited to, rottlerin;

(58) polyamine synthesis inhibitors, including, but not limited to, (RS)-2,5-diamino-2-(difluoromethyl)pentanoic acid (DMFO);

(59) proteasome inhibitors, including, but not limited to, aclacinomycin A, gliotoxin, and bortezomib;

(60) PTP1B inhibitors, including, but not limited to, (E)-N-[4-(2-carboxyethenyl)benzoyl]glycyl-L-α-glutamyl-L-leucinamide;

(61) protein tyrosine kinase inhibitors, including, but not limited to: Tyrphostin AG 126; Tyrphostin AG 1288; Tyrphostin AG 1295; geldanamycin; and genistein;

(62) SRC family tyrosine kinase inhibitors, including, but not limited to, 1-(1,1-dimethylethyl)-3-(1-naphthalenyl)-1H-pyrazolo[3,4-d]pyrimidin-4-amine, and 3-(4-chlorophenyl)-1-(1,1-dimethylethyl)-1H-pyrazolo[3,4-d]pyrimidin-4-amine;

(63) Syk tyrosine kinase inhibitors including, but not limited to, piceatannol;

(64) Janus (JAK-2 and/or JAK-3) tyrosine kinase inhibitors, including, but not limited to, Tyrphostin AG 490, and 2-naphthyl vinyl ketone;

(65) inhibitors of Ras oncogenic isoforms, including, but not limited to, (2S)-2-[[(2S)-2-[(2S,3S)-2-[(2R)-2-amino-3-mercaptopropyl]amino]-3-methylpentyl]oxy]-1-oxo-3-phenylpropyl]amino]-4-(methylsulfonyl)-butanoic acid 1-methylethyl ester (L-744832), DK8G557, and tipifarnib;

(66) retinoids, including, but not limited to, isotretinoin and tretinoin;

(67) ribonucleotide reductase inhibitors, including, but not limited to, hydroxyurea and 2-hydroxy-1H-isoindole-1,3-dione;

(68) RNA polymerase II elongation inhibitors, including, but not limited to, 5,6-dichloro-1-beta-D-ribofuranosylbenzimidazole;

(69) S-adenosylmethionine decarboxylase inhibitors, including, but not limited to, 5-amidino-1-tetralone-2'-amidinohydrazone and other compounds disclosed in U.S. Pat. No. 5,461,076 to Stanek et al., incorporated herein by this reference;

(70) serine/threonine kinase inhibitors, including, but not limited to, sorafenib and 2-aminopurine;

(71) compounds which target, decrease, or inhibit the activity or function of serine/threonine mTOR kinase, including, but not limited to, everolimus, temsirolimus, zotarolimus, rapamycin, derivatives and analogs of rapamycin, deforolimus, AP23841, sirolimus, and everolimus;

(72) somatostatin receptor antagonists, including, but not limited to, octreotide and pasireotide (SOM230);

(73) sterol biosynthesis inhibitors, including, but not limited to, terbinadine;
(74) telomerase inhibitors, including, but not limited to, telomestatin; and
(75) topoisomerase inhibitors, including, but not limited to:
 (a) topoisomerase I inhibitors, including, but not limited to, topotecan, gimatecan, irinotecan, camptothecin and its analogues, 9-nitrocamptothecin and the macromolecular camptothecin conjugate PNU-16614, macromolecular camptothecin conjugates described in PCT Patent Application Publication No. WO 99/17804 by Angelucci et al., 10-hydroxycamptothecin acetate salt, etoposide idarubicin hydrochloride, teniposide, doxorubicin; epirubicin hydrochloride, mitoxantrone hydrochloride, and daunorubicin hydrochloride; and
 (b) topoisomerase II inhibitors, including, but not limited to, anthracyclines, such as doxorubicin, including liposomal formulations thereof, daunorubicin, including liposomal formulations thereof, epirubicin, idarubicin, nemorubicin, mitoxantrone, losoxantrone, etoposide, and eniposide;
(76) VEGFR tyrosine kinase inhibitors, including, but not limited to, 3-(4-dimethylaminobenzylidenyl)-2-indolinone; and
(77) RANKL inhibitors, including, but not limited to, denosumab.

When the improvement is made by chemosensitization, the chemosensitization can comprise, but is not limited to, the use of an alkylating agent such as uracil mustard as a chemosensitizer in combination with an agent selected from the group consisting of:
 (a) topoisomerase inhibitors;
 (b) fraudulent nucleosides;
 (c) fraudulent nucleotides;
 (d) thymidylate synthetase inhibitors;
 (e) signal transduction inhibitors;
 (f) cisplatin or platinum analogs;
 (g) alkylating agents;
 (h) anti-tubulin agents;
 (i) antimetabolites;
 (j) berberine;
 (k) apigenin;
 (l) colchicine or an analog of colchicine;
 (m) genistein;
 (n) etoposide;
 (o) cytarabine;
 (p) camptothecin;
 (q) vinca alkaloids;
 (r) 5-fluorouracil;
 (s) curcumin;
 (t) NF-κB inhibitors;
 (u) rosmarinic acid; and
 (v) mitoguazone.

When the improvement is made by chemopotentiation, the chemopotentiation can comprise, but is not limited to, the use of an alkylating agent such as uracil mustard as a chemopotentiator in combination with an agent selected from the group consisting of:
 (a) fraudulent nucleosides;
 (b) fraudulent nucleotides;
 (c) thymidylate synthetase inhibitors;
 (d) signal transduction inhibitors;
 (e) cisplatin or platinum analogs;
 (f) alkylating agents;
 (g) anti-tubulin agents;
 (h) antimetabolites;
 (i) berberine;
 (j) apigenin;
 (k) colchicine or analogs of colchicine;
 (l) genistein;
 (m) etoposide;
 (n) cytarabine;
 (o) camptothecins;
 (p) vinca alkaloids;
 (q) topoisomerase inhibitors;
 (r) 5-fluorouracil;
 (s) curcumin;
 (t) NF-κB inhibitors;
 (u) rosmarinic acid; and
 (v) mitoguazone.

When the improvement is made by post-treatment management, the post-treatment management can be, but is not limited to, a method selected from the group consisting of:
 (a) a therapy associated with pain management;
 (b) nutritional support;
 (c) administration of an anti-emetic;
 (d) an anti-nausea therapy;
 (e) administration of an anti-inflammatory agent;
 (f) administration of an antipyretic agent; and
 (g) administration of an immune stimulant.

Anti-inflammatory agents and antipyretic agents are well known in the art. Immune stimulants are known in the art and include, but are not limited to, filgrastim, CpG deoxynucleotide, ancestim, glatiramer acetate, interferons, interleukins, lentinan, resiquimod, and imiquimod.

When the improvement is made by alternative medicine/post-treatment support, the alternative medicine/post-treatment support can be, but is not limited to, a method selected from the group consisting of:
 (a) hypnosis;
 (b) acupuncture;
 (c) meditation;
 (d) administration of a herbal medication created either synthetically or through extraction; and
 (e) applied kinesiology.

In one alternative, when the method is administration of a herbal medication created either synthetically or through extraction, the herbal medication created either synthetically or through extraction can be selected from the group consisting of:
 (a) a NF-κB inhibitor;
 (b) a natural anti-inflammatory;
 (c) an immunostimulant;
 (d) an antimicrobial; and
 (v) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an anti-microbial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O- malonylgenistin, 6″-O-acetylgenistin, daidzein, daidzin, 6″-O-malonyldaidzin, 6″-O-acetylgenistin, glycitein, glycitin, 6″-O-malonylglycitin, and 6-O-acetylglycitin.

When the improvement is made by a bulk drug product improvement, the bulk drug product can be, but is not limited to, a bulk drug product improvement selected from the group consisting of:
(a) preparation as a free base form;
(b) salt formation;
(c) preparation as a homogeneous crystalline structure;
(d) amorphous structure;
(e) preparation as a pure isomer;
(f) increased purity;
(g) polymorphs;
(h) preparation with lower residual solvent content; and
(i) preparation with lower residual heavy metal content.

When the improvement is made by use of a diluent, the diluent can be, but is not limited to, a diluent selected from the group consisting of:
(a) an emulsion;
(b) dimethylsulfoxide (DMSO);
(c) N-methylformamide (NMF)
(d) dimethylformamide (DMF)
(e) dimethylacetamide (DMA);
(f) ethanol;
(g) benzyl alcohol;
(h) dextrose-containing water for injection;
(i) Cremophor;
(j) cyclodextrins; and
(k) PEG.

When the improvement is made by use of a solvent system, the solvent system can be, but is not limited to, a solvent system selected from the group consisting of:
(a) an emulsion;
(b) DMSO;
(c) NMF;
(d) DMF;
(e) DMA;
(f) ethanol;
(g) benzyl alcohol;
(h) dextrose-containing water for injection;
(i) Cremophor;
(j) PEG; and
(k) salt systems.

When the improvement is made by use of an excipient, the excipient can be, but is not limited to, an excipient selected from the group consisting of:
(a) mannitol;
(b) albumin;
(c) EDTA;
(d) sodium bisulfite;
(e) benzyl alcohol;
(f) carbonate buffers;
(g) phosphate buffers;
(h) PEG;
(i) vitamin A;
(j) vitamin D;
(k) vitamin E;
(l) esterase inhibitors;
(m) cytochrome P450 inhibitors;
(n) multi-drug resistance (MDR) inhibitors;
(o) organic resins;
(p) detergents;
(q) perillyl alcohol or an analog thereof; and
(r) activators of channel-forming receptors.

Suitable esterase inhibitors include, but are not limited to, ebelactone A and ebelactone B.

Suitable cytochrome P450 inhibitors include, but are not limited to, 1-aminobenzotriazole, N-hydroxy-N'-(4-butyl-2-methylphenyl)formamidine, ketoconazole, methoxsalen, metyrapone, roquefortine C, proadifen, 2,3',4,5'-tetramethylstilbene, and troleandomycin.

Suitable MDR inhibitors include, but are not limited to, 5'-methoxyhydnocarpin, INF 240, INF 271, INF 277, INF 392, INF 55, reserpine, and GG918. MDR inhibitors are described in M. Zloh & S. Gibbons, "Molecular Similarity of MDR9 Inhibitors," Int. J. Mol. Sci. 5: 37-47 (2004), incorporated herein by this reference.

Suitable organic resins include, but are not limited to, a partially neutralized polyacrylic acid, as described in U.S. Pat. No. 8,158,616 to Rodgers et al., incorporated herein by this reference.

Suitable detergents include, but are not limited to, nonionic detergents such as a polysorbate or a poloxamer, and are described in PCT Patent Application Publication No. WO/1997/039768 by Bjorn et al., incorporated herein by this reference.

The use of perillyl alcohol or an analog thereof to improve transport of anti-neoplastic agents is described in United States Patent Application 2012/0219541 by Chen et al., incorporated herein by this reference.

The use of activators of channel-forming receptors is described in United States Patent Application Publication No. 2010/0311678 by Bean et al., incorporated herein by this reference. Such activators of channel-forming receptors include, but are not limited to, capsaicin, lidocaine, eugenol, arvanil (N-arachidonoylvanillamine), anandamide, 2-aminoethoxydiphenyl borate, resiniferatoxin, phorbol 12-phenylacetate 13-acetate 20-homovanillate (PPAHV), olvanil, N-oleoyldopamine, N-arachidonyldopamine, 6'-iodoresiniferatoxin (6'-IRTX), $C_{18}$ N-acylethanolamines, lipoxygenase derivatives such as 12-hydroperoxyeicosatetraenoic acid, inhibitor cysteine knot (ICK) peptides (vanillotoxins), piperine, N-[2-(3,4-dimethylbenzyl)-3-(pivaloyloxy)propyl]-2-[4-(2-aminoethoxy)-3-methoxyphenyl]acetamide, N-[2-(3,4-dimethylbenzyl)-3-(pivaloyloxy)propyl]-N'-(4-hydroxy-3-methoxybenzyl)thiourea, SU200 N-(4-t-butylbenzyl)-N'-(4-hydroxy-3-methoxybenzyl)thiourea), transacin, cinnamaldehyde, allyl-isothiocyanate, diallyl disulfide, icilin, cinnamon oil, wintergreen oil, clove oil, acrolein, mustard oil, ATP, 2-methylthio-ATP, 2' and 3'-O-(4-benzoylbenzoyl)-ATP, ATP-5'-O-(3-thiotriphosphate), menthol, eucalyptol, linalool, geraniol, and hydroxycitronellal.

When the improvement is made by use of a dosage form, the dosage form can be, but is not limited to, a dosage form selected from the group consisting of:
(a) tablets;
(b) capsules;
(c) topical gels;
(d) topical creams;
(e) patches;
(f) suppositories;
(g) lyophilized dosage fills;
(h) immediate-release formulations;
(i) slow-release formulations;
(j) controlled-release formulations;
(k) liquid in capsules;
(l) 1-mg capsules;
(m) 5-mg capsules;
(n) 10-mg capsules;
(o) 1-mg tablets;
(p) 5-mg tablets;
(q) 10-mg tablets;
(r) coated tablets;

(s) lyophilized dosages suitable for intravenous administration;
(t) stable liquid formulations; and
(u) stabilized compositions comprising a non-aqueous carrier.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dibromodulcitol and derivatives thereof, comprises the following steps:

(1) Dissolve the drug in water for injection precooled to below 10° C. Dilute to final volume with cold water for injection to yield a 40 mg/mL solution.
(2) Filter the bulk solution through an 0.2-μm filter into a receiving container under aseptic conditions. The formulation and filtration should be completed in 1 hour.
(3) Fill nominal 1.0 mL filtered solution into sterilized glass vials in a controlled target range under aseptic conditions.
(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.
(5) The vials are then frozen to 30° C. or below and held for no less than 3 hours, typically 4 hours.
(6) Vacuum is then turned on, the shelf temperature is adjusted to −5° C., and primary drying is performed for 8 hours; the shelf temperature is again adjusted to −5° C. and drying is carried out for at least 5 hours.
(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.
(8) Break the vacuum with filtered inert gas (e.g., nitrogen). Stopper the vials in the lyophilizer.
(9) Vials are removed from the lyophilizer chamber and sealed with aluminum flip-off seals. All vials are visually inspected and labeled with approved labels.

Immediate-release formulations are described in U.S. Pat. No. 8,148,393 to van Dalen et al., incorporated herein by this reference. Immediate-release formulations can include, for example, conventional film-coated tablets.

Slow-release formulations are described in U.S. Pat. No. 8,178,125 to Wen et al., incorporated herein by this reference. Slow-release formulations can include, for example, microemulsions or liquid crystals.

Controlled-release formulations are described in U.S. Pat. No. 8,231,898 to Oshlack et al., incorporated herein by this reference. Controlled-release formulations can include, for example, a matrix that includes a controlled-release material. Such a controlled-release material can include hydrophilic and/or hydrophobic materials, such as gums, cellulose ethers, acrylic resins, protein derived materials, waxes, shellac, and oils such as hydrogenated castor oil or hydrogenated vegetable oil. However, any pharmaceutically acceptable hydrophobic or hydrophilic controlled-release material which is capable of imparting controlled-release of the mustard-based alkylating agent may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polymethacrylate, polyacrylamide, poly(methacrylic acid anhydride), and glycidyl methacrylate copolymers.

The preparation and use of coated tablets for delivery of therapeutic agents is well known in the art. A variety of coatings are known. For example, and not by way of limitation, U.S. Pat. No. 8,378,117 to Liotta et al. discloses the use of film-coated tablets. U.S. Pat. No. 8,378,108 to Corkey et al. discloses the use of enteric-coated tablets. U.S. Pat. No. 8,377,962 Parsy et al. to Parsy et al. discloses the use of enteric-coated tablets, sugar-coated tablets, film-coated tablets, press-coated tablets, and dry-coated tablets. The film-coated tablets can use coatings of hydroxyethylcellulose, sodium carboxymethylcellulose, polyethylene glycol 4000, or cellulose acetate phthalate. U.S. Pat. No. 8,377,961 to Lacrampe et al. discloses the use of tablets coated with a methylcellulose/ethylcellulose/polyethylene glycol/magnesium octadecanoate/polyvinylpyrrolidone/color suspension. U.S. Pat. No. 8,377,943 to Sapountzis et al. discloses the use of a coating agent that can be collidone, shellac, gum Arabic, talc, titanium dioxide, or sugar for coated tablets. U.S. Pat. No. 8,377,938 to Matsushima et al. discloses film coated tablets with hydroxypropylcellulose, macrogol, titanium oxide, talc, and red iron oxide. U.S. Pat. No. 8,377,897 to Teng et al. discloses enteric coated tablets with cellulose acetate phthalate. U.S. Pat. No. 8,372,979 to Welzig et al. discloses coated tablets with hypromellose/hypromellose phthalate. U.S. Pat. No. 8,372,830 to Liu et al. discloses sugar-coated tablets, gelatin-coated tablets, and enteric-coated tablets. U.S. Pat. No. 8,372,451 to Vackovic discloses coated tablets coated with hydroxypropylmethylcellulose, synthetic polymers, shellac, zein, or polysaccharides. All of these United States patents are incorporated herein by this reference. Additionally, stabilized liquid formulations, including a stable liquid formulation of a nitrogen mustard such as uracil mustard that includes a non-aqueous liquid having at least a first solvent either individually or in combination with one or more additional solvents, and wherein the formulation further includes an antioxidant, an organic acid, and a source of chloride ions, are disclosed in United States Patent Application Publication No. 2014/0005148 by Neelakantan et al., incorporated herein by this reference. Stabilized compositions comprising uracil mustard and a non-aqueous carrier are disclosed in U.S. Pat. No. 8,664,278 to Alonso et al., incorporated herein by this reference. Typically, the composition includes a pharmaceutically acceptable excipient that is $HOCH_2CH_2OCH_2CH_2OR_{79}$, wherein $R_{79}$ is a linear alkyl group having 1-6 carbon atoms.

Additional coatings and coating methods are well known in the art, including polyvinyl alcohol coatings, ethylcellulose coatings, semipermeable membrane coatings, methacrylic acid polymer coatings, and others.

As used herein generally with respect to dosage forms and modalities, the term "API" refers to an active pharmaceutical ingredient, such as uracil mustard or a derivative or analog thereof, as described above. As used herein generally with respect to dosage forms and modalities, the term "solid oral dosage form" and equivalent phrases (e.g., "oral dosage form," "dosage form for oral administration," "oral dosage unit" or other terminology referring to dosage forms suitable for oral administration is a pharmaceutical composition in the form of a tablet, capsule, gelcap, or other form that can be administered orally to a patient in the normal course of treatment. As used herein generally with respect to dosage forms and modalities, the term "excipient" is any component of an oral dosage form that is not an API. Examples include, but are not limited to, binders, lubricants, diluents, disintegrants, coatings, barrier layer components, glidants, and other components. Excipients are known in the art. Some excipients serve multiple functions or are so-called high-functionality excipients. For example, talc may act as a lubricant, an anti-adherent, and a glidant. As used herein generally with respect to dosage forms and modalities, the term "binder" is an excipient that imparts cohesive qualities to components of a pharmaceutical composition. Commonly used binders include, for example, starch; sugars, such as, sucrose, glucose, dextrose, and lactose; cellulose derivatives such as powdered cellulose, microcrystalline cellulose, silicified microcrystalline cellulose (SMCC), hydroxypropylcellulose, low-substituted hydroxypropylcellulose, hypromellose (hydroxypropylmethylcellulose); and mixtures of these and similar ingredients. As used herein generally with respect to dosage forms and modalities, the term "lubricant" is an excipient added to reduce sticking by a solid formulation to the equipment used for production of a unit does form, such as, for example, the punches of a tablet press. Examples of lubricants include magnesium stearate and calcium stearate. As used herein generally with respect to dosage forms and modalities, the term "diluent" is an excipient added to a pharmaceutical composition to increase bulk weight of the material to be formulated in order to achieve the desired weight. As used herein generally with respect to dosage forms and modalities, the term "disintegrant" refers to excipients included in a pharmaceutical composition in order to ensure that the composition has an acceptable disintegration rate in an environment of use. Examples of disintegrants include starch derivatives (e.g., sodium carboxymethyl starch and pregelatinized corn starch and salts of carboxymethylcellulose (e.g., sodium carboxymethylcellulose), crospovidone. As used herein generally with respect to dosage forms and modalities, the term "glidant" is used to refer to excipients included in a pharmaceutical composition to keep the component powder flowing as the tablet is being made, preventing formation of lumps. Nonlimiting examples of glidants are colloidal silicon dioxides such as CAB-O-SIL™ (Cabot Corp.), AEROSIL™ (Degussa), or talc. As used herein generally with respect to dosage forms and modalities, the terms "over-coating," "over-coating layer," or "over-coat" refer to the outermost coating or coatings of a unit dose form such as a tablet or caplet, which may be added to improve appearance, taste, swallowability, or other characteristics of the table or caplet. The over coating layer does not contain an API. Suitable over-coatings are soluble in, or rapidly disintegrate in water, and, for purposes of this invention, are not enteric coatings. An exemplary over-coating material is Opadry II available from Colorcon, Inc., Westpoint Pa.

The excipients used in one alternative for the manufacture of tablets including uracil mustard and the rationale for the levels specified for the excipients are summarized below. The recitation of these particular excipients and their levels is not to be interpreted as excluding other possible excipients, either in place of or in addition to, the excipients recited or as excluding other levels of the excipients recited.

Cornstarch is a starch. It is widely used as a binder and disintegrant in solid formulations prepared by wet granulation. Typically a level of 5-25% w/w is used in tablet granulation as a binder. Lactose monohydrate is used as a diluent, which enhances the manufacturability of the formulation by masking the physical properties of the active pharmaceutical ingredient, uracil mustard. Additionally, dissolution is enhanced by the high solubility of lactose, and lactose itself can easily be compressed into tablets. Colloidal silicon dioxide is a glidant. Its small particle size and large specific surface area gives it desirable flow characteristics, which improves the flow properties of powders in the process. Microcrystalline cellulose is widely used as a diluent in oral tablet formulations. In addition to its use as a diluent, microcrystalline cellulose also has some lubricant and disintegrant properties making useful in tableting. It has good compressibility. Microcrystalline cellulose is added to the extra-granular portion to assist in blending and compression of tablets. Typically a level of 20-90% w/w is used in tablet formulation as a diluent. Sodium starch glycolate is a disintegrant used in oral pharmaceuticals. The usual level employed in a formulation is between 2-8% w/w, with the optimum level about 4% w/w. Disintegration occurs by rapid uptake of water followed by rapid and enormous swelling. Magnesium stearate, NF, is used as a lubricant to facilitate the ejection of the tablet from the tablet die during the tablet compression process. Hypromellose or hydroxypropyl methylcellulose is primarily used as a tablet binder in film-coating. 2-5% w/w is generally used as a binder in wet or dry granulation processes. Titanium dioxide is used as a white pigment and opacifier in film-coating suspensions. Due to its high refractive index, titanium dioxide has unique light scattering properties. Polyethylene glycol 400 is used to increase the water permeability in film coats. Purified water, USP and alcohol are the granulating liquids used to produce agglomerates or granules of drug-excipient particles and facility processing. The water and alcohol are removed during the subsequent drying process. Alcohol is also used in the film-coating step as a carrier. Alcohol is non-retained after drying.

Table 1 shows the composition of tablets including 1 mg of uracil mustard per tablet. Table 2 shows the composition of tablets including 5 mg of uracil mustard per tablet. For these tablets, the water shown in the table is removed during the tableting process and therefore is not factored in the tablet weight.

TABLE 1

Uracil Mustard Tablets with 1 mg per Tablet

| Component | Function | Amount per Tablet (mg) | % of Tablet (w/w) |
|---|---|---|---|
| Uracil Mustard, USP | Active | 1 | 1.0 |
| Lactose monohydrate, NF | Filler | 20 | 20.0 |
| Corn starch, NF | Binder/disintegrant | 40 | 40.0 |
| Colloidal silicon dioxide, NF | Binding agent | 1.5 | 1.5 |
| Croscarmellose sodium, NF | Binding agent | 10 | 10.0 |

TABLE 1-continued

Uracil Mustard Tablets with 1 mg per Tablet

| Component | Function | Amount per Tablet (mg) | % of Tablet (w/w) |
|---|---|---|---|
| Hypromellose, USP | Filler | 4 | 4.0 |
| Microcrystalline cellulose, NF | Binding agent | 20 | 20.0 |
| Magnesium stearate, NF | Lubricant | 0.5 | 0.5 |
| Opadry II white | Film coating | 3 | 3.0 |
| Purified water, USP | Solvent | N/A | N/A |
| Total Tablet Weight | | 100 | 100 |

TABLE 2

Uracil Mustard Tablets with 5 mg per Tablet

| Component | Function | Amount per Tablet (mg) | % of Tablet (w/w) |
|---|---|---|---|
| Uracil Mustard, USP | Active | 5 | 5.0 |
| Lactose monohydrate, NF | Filler | 16 | 16.0 |
| Corn starch, NF | Binder/disintegrant | 40 | 40.0 |
| Colloidal silicon dioxide, NF | Binding agent | 1.5 | 1.5 |
| Croscarmellose sodium, NF | Binding agent | 10 | 10.0 |
| Hypromellose, USP | Filler | 4 | 4.0 |
| Microcrystalline cellulose, NF | Binding agent | 20 | 20.0 |
| Magnesium stearate, NF | Lubricant | 0.5 | 0.5 |
| Opadry II white | Film coating | 3 | 3.0 |
| Purified water, USP | Solvent | * | * |
| Total Tablet Weight | | 100 | 100% |

The Opadry II white used in the film coating process has a formula shown in Table 3, below.

TABLE 3

Formulation of Opadry II White

| Ingredients | % w/w | Grade |
|---|---|---|
| Polyvinyl alcohol | 40.0 | USP, PhEur, JPE |
| Titanium dioxide | 25.0 | USP, FCC, PhEur, JP |
| Macrogol/PEG 3350 | 20.2 | NF, PhEur, JP |
| Talc | 14.8 | USP, FCC, PhEur, JP |

The manufacturing process for uracil mustard tablets (1 mg or 5 mg) consists of four steps: (1) preparation of granules; (2) preparation of powder blend; (3) preparation of uncoated tablets; and (4) film coating of tablets. The manufacturing steps are described below.

Preparation of Granules (1) Weigh uracil mustard into a suitable container. (2) Weigh excipients into suitable containers. (3) Weigh intra-granular portion of hydroxypropyl methylcellulose and dissolve it into a water-alcohol mixture. (4) Add uracil mustard and intra-granular excipients (cornstarch, lactose, and colloidal silicon dioxide) to a mixer-granulator and blend at high speed for 3 minutes. (5) Add the water-alcohol mixture prepared in (3) and mixed at low speed for 6 minutes, followed by mixing at high speed for another 9 minutes. (6) Transfer wet granules to fluid bed dryer and dry the granules until the residual water content is not greater than 3.0%. (7) Discharge and screen the dried granules on a vibrating sieve equipped with a 20 mesh (0.8 mm) screen. (8) Weigh the resultant wet granules, and calculate the required amount of extra-granular excipients (microcrystalline cellulose, sodium starch glycolate, magnesium stearate, and colloidal silicon dioxide). Process controls used in preparation of granules are appearance, water content, and particle size determination.

Preparation of Powder Blend (9) Transfer the dried granules to a blender and mixing with extra-granular excipients, microcrystalline cellulose, sodium starch glycolate, magnesium stearate, and colloidal silicon dioxide. (10) Blend the mixture (9) in a low shear mixer. Process controls used in preparation of the powder blend are appearance, content uniformity, water content, and assay for uracil mustard.

Preparation of Uncoated Tablets

(11) Upon release of powder blend, compress powder blend into tablets using a rotary compressor. (12) Store tablets in bulk in HDPE drum at controlled temperature. Perform the in-process controls for appearance, content uniformity, tablet weight, hardness, friability, disintegration time, tablet weight, and assay for uracil mustard.

Tablet Film Coating

(13) Mix titanium dioxide, alcohol, hydroxypropyl methylcellulose, with water and ethanol. (14) Upon release of core tablets, transfer the core tablets to the film-coating drum. Adjust the spray gun position, the spray speed, the coating pan rotating speed, and the temperature. Precede the film coating. (15) Tablets are dried and submitted for testing. Process controls used in tablet film coating are appearance, tablet weight, and disintegration time.

Other methods known in the art can be used to prepare coated tablets including uracil mustard and other derivatives.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:

(a) oral dosage forms;
(b) nanocrystals;
(c) nanoparticles;
(d) cosolvents;
(e) slurries;
(f) syrups;
(g) bioerodible polymers;
(h) liposomes;
(i) slow-release injectable gels;
(j) microspheres;
(k) targeting compositions with epidermal growth factor receptor-binding peptides;
(l) bispecific antibody pretargeting;
(m) single chain variable region antibody fragments cloned by phage display; and
(n) polymeric micelles for drug delivery.

Nanocrystals are described in U.S. Pat. No. 7,101,576 to Hovey et al., incorporated herein by this reference.

Nanoparticles for drug delivery are described in U.S. Pat. No. 8,258,132 to Bosch et al., incorporated herein by this reference. Typically, such nanoparticles have an average particle size of the active ingredient of less than about 1000 nm, more preferably, less than about 400 nm, and most preferably, less than about 250 nm. The nanoparticles can be coated with a surface stabilizer, such as, but not limited to, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxes 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)), dioctyl sodium sulfosuccinate (DOSS), docusate sodium (Ashland Chem. Co., Columbus, Ohio); Duponol P®, which is a sodium lauryl sulfate (DuPont); Triton X-200®, which is an alkyl aryl polyether sulfonate (Rohm and Haas); Crodestas F-110®, which is a mixture of sucrose stearate and sucrose distearate (Croda Inc.); p-isononylphenoxy-poly-(glycidol), also known as Olin-IOG® or Surfactant 10-G® (Olin Chemicals, Stamford, Conn.); Crodestas SL-40® (Croda, Inc.); and SA9OHCO, which is $C_{18}H_{37}CH_2(CON(CH_3)-OCH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methyl-glucamide; n-heptyl-β-D-glucopyranoside; n-heptyl β-D-thioglucoside; n-hexyl β-D-glucopyranoside; nonanoyl-N-methylglucamide; n-nonanoyl β-D-glucopyranoside; octanoyl-N-methylglucamide; n-octyl β-D-glucopyranoside; and octyl β-D-thioglucopyranoside. Nanoparticles for drug delivery are also described in United States Patent Application Publication No. 2010/209479 by Carroll et al., incorporated herein by this reference. These nanoparticles include carbon nanoparticles such as carbon nanotubes.

Pharmaceutically acceptable cosolvents are described in U.S. Pat. No. 8,207,195 to Navratil et al., incorporated herein by this reference, and include, but are not limited to, water, methanol, ethanol, 1-propanol, isopropanol, 1-butanol, isobutanol, t-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether.

Slurries for use in pharmaceutical formulations are described in United States Patent Application Publication No. 2006/0229277 by Laxminarayan, incorporated herein by this reference.

Syrups for use in pharmaceutical formulations are described in U.S. Pat. No. 8,252,930 to Stoit et al., incorporated herein by this reference. Such syrups can include the active ingredient and a syrup-forming component such as sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference. Liposomes can incorporate short oligopeptide sequences capable of targeting the EGFR receptor, as described in United States Patent Application Publication 2012/0213844 by Huang et al., incorporated herein by this reference. Alternatively, liposomes can include nuclear localization signal/fusogenic peptide conjugates and form targeted liposome complexes, as described in United States Patent Application Publication 2012/0183596 to Boulikas, incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000), incorporated herein by this reference.

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

The use of targeting compositions with epidermal growth factor receptor-binding peptides is described in United States Patent Application Publication No. 2010/0151003 by Trikha et al., incorporated herein by this reference.

The use of bispecific antibody pretargeting is described in U.S. Pat. No. 8,652,484 to McBride et al., in U.S. Pat. No. 8,435,539 to McBride et al., and in United States Patent Application No. 2014/0086832 by McBride et al., all of which are incorporated herein by this reference.

The use of single chain variable region antibody fragments cloned by phage display as delivery agents for uracil mustard is described in U.S. Pat. No. 8,470,323 to Stanley et al., incorporated herein by this reference.

The use of polymeric micelles for drug delivery is described in United States Patent Application Publication No. 2013/0195987 by Breitenkamp et al., incorporated herein by this reference.

When the improvement is made by use of a drug conjugate form, the drug conjugate form can be, but is not limited to, a drug conjugate form selected from the group consisting of:
(a) a polymer system;
(b) polylactides;
(c) polyglycolides;
(d) amino acids;
(e) peptides;
(f) multivalent linkers;
(g) immunoglobulins;
(h) cyclodextrin polymers;
(i) modified transferrin;
(j) hydrophobic or hydrophobic-hydrophilic polymers;
(k) conjugates with a phosphonoformic acid partial ester;
(l) conjugates with a cell-binding agent incorporating a charged cross-linker;
(m) conjugates with β-glucuronides through a linker;
(n) conjugates with anti-CD-49 antibodies;
(o) conjugates with activatable compounds;
(p) conjugates with targetable constructs;
(q) charged or pro-charged conjugates of cell-binding agents;
(r) conjugates with anti-CD74 antibodies, typically with the administration of fingolimod;
(s) conjugates with anti-GITR antibodies;
(t) conjugates with hypoxia-selective, weakly basic 2-nitroimidazole delivery agents;
(u) conjugates with a water-soluble non-peptidic polymer;
(v) conjugates with a hydrohalide salt of a multi-arm water-soluble polyethylene glycol;
(w) conjugates with pheophorbide-α;
(x) conjugates with cancer-targeting peptides, in which the cancer-targeting peptides have a $PX_1LX_2$ motif, in which $X_1$ is His or an amino acid residue with a hydrophobic side chain and $X_2$ is Pro, Phe, or Trp;
(y) conjugates with a bioactive assembly formed using dock-and-lock methodology which takes advantage of the specific binding interaction between dimerization and docking domains (DDD) and anchoring domains (AD) to form the assembly; and
(z) conjugates with a hexavalent molecular building block, wherein the linkage of additional moieties to the amino and carboxyl terminals of monomers comprising the NC2 domain of collagen IX promotes the directed association of those moieties via the trimerization initiating and stagger determining capacity of the NC2 domain of collagen IX, and wherein the NC2 domain of collagen X is conjugated to uracil mustard or a derivative or analog thereof.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Conjugates with immunoglobulins are disclosed in U.S. Pat. No. 4,925,662 to Oguchi et al., incorporated herein by this reference. The conjugates are prepared by use of a cross-linking agent such as carbodiimide, glutaraldehyde, or diethyl malonimidate.

Cyclodextrin polymers, their conjugates with therapeutically active agents, and their administration together with particles are described in United States Patent Application Publication Serial No. 2012/0213854 by Fetzer, incorporated herein by this reference.

Conjugates with modified transferrin are described in United States Patent Application Publication Serial No. 2011/0288023 by Kamei et al., incorporated herein by this reference.

Conjugates with hydrophobic or hydrophobic-hydrophilic polymers are described in United States Patent Application Publication No. 2011/0268658 by Crawford et al., incorporated herein by this reference. These polymers can include mono-, di-, or tripeptides. These polymers can also include polylactic acid (PLA), polyglycolic acid (PGA), poly(lactic-co-glycolic) acid (PLGA), polycaprolactone (PCL), polydioxanone (PDO), polyanhydrides, polyorthoesters, or chitosan.

Conjugates with a phosphonoformic acid partial ester are described in United States Patent Application Publication No. 2010/227831 by Saha et al., incorporated herein by this reference.

Conjugates with a cell-binding agent incorporating a charged cross-linker are described in U.S. Pat. No. 8,236,319 to Chari et al., incorporated herein by this reference.

Conjugates with β-glucuronides through a linker are described in U.S. Pat. No. 8,039,273 to Jeffrey, incorporated herein by this reference, in U.S. Pat. No. 8,568,728 to Jeffrey, incorporated herein by this reference, and in United States Patent Application Publication No. 2014/0031535 by Jeffrey, incorporated herein by this reference.

Conjugates with anti-CD49 antibodies are described in U.S. Pat. No. 8,680,243 to Funahashi, incorporated herein by this reference. Typically, the antibody comprises a human constant region and has internalizing activity and cytotoxic activity.

Conjugates with activatable compounds are described in U.S. Pat. No. 8,637,490 to Peng et al., incorporated herein by this reference. Typically, the compounds are compounds of Formula E-I:

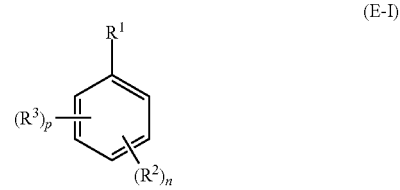

(E-I)

wherein:
(i) each $R^1$ is independently —$B(XR')_2$, wherein each X is independently selected from O and S, and each R' is independently selected from hydrogen and alkyl, or two R' groups are taken together to form an optionally substituted 5-membered to 8-membered ring;

(ii) each $R^2$ is independently selected from optionally substituted alkyl, alkoxy, amino, halo, and —$CH_2$—N$(R^a)_3^+$;

(iii) each R3 is independently selected from Subformulas (E-I(a)) and (E-I(b)):

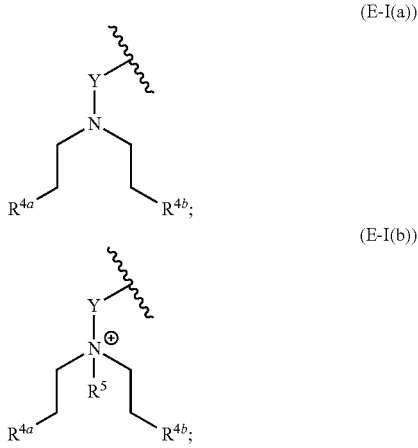

(iv) each $R^{4a}$ and $R^{4b}$ is independently selected from halo and —$OSO_2R^a$;
(v) each Y is independently a bond or —$CH_2$—;
(vi) each $R^5$ is independently $C_1$-$C_4$ alkyl;
(vi) n is 0, 1, or 2;
(vii) p is 1 or 2; and
(viii) each $R^a$ is independently selected from optionally substituted alkyl; wherein if the compound of Formula (E-I) bears a positive charge, it further comprises at least one counterion Z.

Conjugates with targetable constructs are described in U.S. Pat. No. 8,632,752 to McBride et al., incorporated herein by this reference. The targetable constructs are assembled by a click chemistry reaction wherein the reaction is typically either a nitrone with a cycloalkyne or an azide with a cycloalkyne.

Charged or pro-charged conjugates of cell-binding agents are described in U.S. Pat. No. 8,613,930 to Chari et al., incorporated herein by this reference. Typically, the compounds are compounds of Formula (E-II):

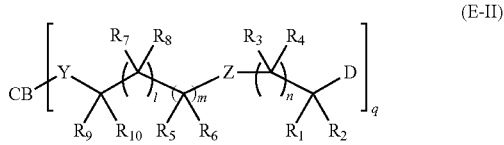

wherein:
(i) CB is a cell-binding agent, such as an antibody;
(ii) D is a cytotoxic drug linked to the cell-binding agent by a disulfide, thioether, thioester, peptide, hydrazone, ester, ether, carbamate, or amide bond;
(iii) $R_1$, $R_2$, $R_3$, $R_4$, $R_5$, $R_6$, $R_7$, $R_8$, $R_9$, and $R_{10}$ are the same or different and are H, unbranched alkyl of 1 to 6 carbon atoms, phenyl, or branched or cyclic alkyl having from 3 to 6 carbon atoms;
(iv) l, m, and n are 0, 1, 2, 3, 4;
(v) Z is an optional polyethyleneoxy unit of formula $(OCH_2CH_2)_p$, wherein p is 0 or an integer from 2 to 1000;
(vi) Y is a carbonyl, thioether, amide, disulfide, or hydrazone group; and
(vii) q is an integer from 1 to 20;
wherein at least one of $R_1$, $R_2$, $R_3$, $R_4$, $R_5$, $R_6$, $R_7$, $R_8$, $R_9$, and $R_{10}$ is a charged substituent.

Conjugates with anti-CD74 antibodies, typically used with the administration of fingolimod, are described in U.S. Pat. No. 8,591,892 to Alinari et al., incorporated herein by this reference. The antibody can be a bispecific antibody forming a dock-and-lock complex.

Conjugates with anti-GITR antibodies or other GITR-binding molecules are described in U.S. Pat. No. 8,591,886 to Ponath et al., incorporated herein by this reference. The GITR-binding molecule can be an antigen-binding fragment of an antibody.

Conjugates with hypoxia-selective, weakly basic 2-nitroimidazole delivery agents are described in U.S. Pat. No. 8,518,371 to Lee et al., incorporated herein by this reference. Typically, the compounds are compounds of Formula (E-III):

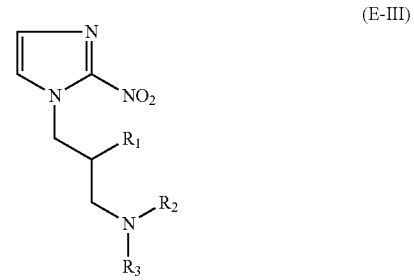

wherein:
(i) R1 is a halogen, positron emitting radionuclide, non-metal, lower alkyl substituted to contain a halogen, lower alkyl substituted to contain a positron emitting radionuclide, lower alkyl substituted to contain a non-metal, tosylate, mesylate, triflate, hydrogen, or hydroxyl; and
(ii) R2 and R3 are linked to form a six-membered heterocyclic ring, wherein the heterocyclic ring comprises a therapeutic agent, cytotoxic agent, detectable label, or chelating group.

Conjugates with a water-soluble non-peptidic polymer are described in United States Patent Application Publication No. 2014/0088021 by Riggs-Sauthier et al., incorporated herein by this reference. In one alternative, the conjugate has the formula Ab-$X^1$-POLY-$X^2$-Dr wherein: Ab is a binding moiety; $X^1$ is a first spacer moiety; POLY is a water-soluble, non-peptidic polymer; $X^2$ is a second spacer moiety; and Dr is a pharmacologically active agent such as a uracil mustard or derivative or analog thereof.

Conjugates with a hydrohalide salt of a multi-arm water-soluble polyethylene glycol are described in United States Patent Application Publication No. 2013/0231359 by Chong et al., incorporated herein by this reference.

Conjugates with pheophorbide-α are described in United States Patent Application Publication No. 2013/0210756 by Kim et al., incorporated herein by this reference. The conjugate can comprise a linker that is a hydroxycinnamoyl moiety or an aminobenzyloxycarbonyl moiety.

Conjugates with cancer-targeting peptides, in which the cancer-targeting peptides have a $PX_1LX_2$ motif, in which $X_1$ is His or an amino acid residue with a hydrophobic side chain and $X_2$ is Pro, Phe, or Trp are described in United States Patent Application Publication No. 2013/0142867 by Yu et al., incorporated herein by this reference.

Conjugates with a bioactive assembly formed using dock-and-lock methodology which takes advantage of the specific binding interaction between dimerization and docking domains (DDD) and anchoring domains (AD) to form the assembly are described in United States Patent Application Publication No. 2013/0164816 by Chang et al., incorporated herein by this reference.

Conjugates with a hexavalent molecular building block, wherein the linkage of additional moieties to the amino and carboxyl terminals of monomers comprising the NC2 domain of collagen IX promotes the directed association of those moieties via the trimerization initiating and stagger determining capacity of the NC2 domain of collagen IX, and wherein the NC2 domain of collagen X is conjugated to uracil mustard are described in United States Patent Application Publication No. 2013/0157257 by Bachinger, incorporated herein by this reference. Variants of these sequences are also described.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonydiimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques," (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a compound analog, the compound analog can be, but is not limited to, a compound analog selected from the group consisting of:
(a) alteration of side chains to increase or decrease lipophilicity;
(b) addition of an additional chemical functionality to alter a property selected from the group consisting of reactivity, electron affinity, and binding capacity;
(c) alteration of salt form; and
(d) attachment of nitroxide free-radical-containing groups.

The modification of uracil mustard by attachment of nitroxide free-radical-containing groups is described in U.S. Pat. No. 8,530,434 to Ba et al., incorporated herein by this reference. The nitroxide free-radical-containing group can be derived from 2,2,6,6-tetramethylpiperidine-1-oxyl or a derivative thereof.

When the improvement is made by use of a prodrug system, the prodrug system can be, but is not limited to, a prodrug system selected from the group consisting of:
(a) the use of enzyme sensitive esters;
(b) the use of dimers;
(c) the use of Schiff bases;
(d) the use of pyridoxal complexes;
(e) the use of caffeine complexes; and
(f) the use of nitric oxide-releasing prodrugs; and
(g) the use of prodrugs with fibroblast activation protein α-cleavable oligopeptides.

As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound as described herein. Thus, the term "prodrug" refers to a precursor of a biologically active compound that is pharmaceutically acceptable. A prodrug can be inactive when administered to a subject, but is then converted in vivo to an active compound, for example, by hydrolysis (e.g., hydrolysis in blood or a tissue). In certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24), incorporated herein by this reference. A discussion of prodrugs is provided in T. Higuchi et al., "Pro-Drugs as Novel Delivery Systems," *ACS Symposium Series, Vol.* 14 and in E. B. Roche, ed., *Bioreversible Carriers in Drug Design* (American Pharmaceutical Association & Pergamon Press, 1987), both incorporated herein by this reference. Exemplary advantages of a prodrug can include, but are not limited to, its physical properties, such as enhanced water solubility for parenteral administration at physiological pH compared to the parent compound, enhanced absorption from the digestive tract, or enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_8$)alkanoyloxymethyl, 1-(($C_1$-$C_8$))alkanoyloxy) ethyl, 1-methyl-1-(($C_1$-$C_8$)alkanoyloxy)ethyl ($C_1$-$C_8$) alkoxycarbonyloxymethyl, N($C_1$-$C_8$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each -aminoacyl group is independently selected from the naturally occurring L-amino acids, P(O) $(OH)_2$, $P(O)(O(C_1$-$C_8)alkyl)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and $R^1$ are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, $C(OH)C(O)OY^1$ wherein Y' is H, ($C_1$-$C_6$)alkyl or benzyl, $C(OY^2)Y^3$ wherein $Y^2$ is ($C_1$-$C_4$)alkyl and $Y^3$ is ($C_1$-$C_6$)alkyl, carboxy($C_1$-$C_6$) alkyl, amino($C_1$-$C_4$)alkyl or mono-N or di-N,N($C_1$-$C_6$)alkylaminoalkyl, $C(Y^4)Y^5$ wherein $Y^4$ is H or methyl and $Y^5$ is mono-N or di-N,N($C_1$-$C_6$)alkylamino, morpholino, piperidin-1-yl or pyrrolidin-1-yl.

The use of prodrug systems is described in T. Järvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference. The use of nitric oxide-releasing prodrugs is described in United States Patent Application Publication No. 2011/0263526 by Satyam, incorporated herein by this reference. The use of prodrugs with fibroblast activation protein α-cleavable oligopeptides is described in United States Patent Application Publication No. 2010/0184706 by Bachovchin et al., incorporated herein by this reference.

When the improvement is made by use of a multiple drug system, the multiple drug system can be, but is not limited to, a multiple drug system selected from the group consisting of the use of a mustard-based alkylating agent with:
  (a) inhibitors of multi-drug resistance;
  (b) specific drug resistance inhibitors;
  (c) specific inhibitors of selective enzymes;
  (d) signal transduction inhibitors;
  (e) meisoindigo;
  (f) imatinib;
  (g) hydroxyurea;
  (h) dasatinib;
  (i) capecitabine;
  (j) nilotinib;
  (k) repair inhibition agents;
  (l) topoisomerase inhibitors with non-overlapping side effects; and
  (m) anti-nausea medications.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference. Signal transduction inhibitors can include, but are not limited to, BCL/ABL kinase inhibitors, epidermal growth factor (EGF) receptor inhibitors, her-2/neu receptor inhibitors, and farnesyl transferase inhibitors, as described in U.S. Pat. No. 8,008,281 by Prendergast et al., incorporated herein by this reference.

Repair inhibition agents are described in N. M. Martin, "DNA Repair Inhibition and Cancer Therapy," *J. Photochem. Photobiol. B* 63: 162-170 (2001), incorporated herein by this reference.

Anti-nausea medications are described above, and include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:
  (a) biological response modifiers;
  (b) cytokines;
  (c) lymphokines;
  (d) therapeutic antibodies;
  (e) antisense therapies;
  (f) gene therapies;
  (g) ribozymes; and
  (h) RNA interference.

Biological response modifiers are described in T. E. G. K. Murthy et al., "Biological Response Modifiers," *Int. J. Pharmtech Res.* 2: 2152-2160 (2010), incorporated herein by this reference.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" *in Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" *in Drug Discovery Handbook* (S. C. Gad, ed., Wiley-Interscience, Hoboken, N.J., 2005), ch. 27, pp. 1278-1283, incorporated herein by this reference.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against tumors resistant to a therapeutic agent or technique selected from the group consisting of:
  (a) biological response modifiers;
  (b) cytokines;
  (c) lymphokines;
  (d) therapeutic antibodies;
  (e) antisense therapies;
  (f) gene therapies;
  (g) ribozymes; and
  (h) RNA interference.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:
  (a) use with hypoxic cell sensitizers;
  (b) use with radiation sensitizers/protectors;
  (c) use with photosensitizers;
  (d) use with radiation repair inhibitors;
  (e) use with thiol depleting agents;
  (f) use with vaso-targeted agents;
  (g) use with DNA repair inhibitors;
  (g) use with radioactive seeds;
  (h) use with radionuclides;
  (i) use with radiolabeled antibodies; and
  (j) use with brachytherapy.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiagnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007), incorporated herein by this reference.

When the improvement is made by use of a novel mechanism of action, the novel mechanism of action can be, but is not limited to, a novel mechanism of action that is a therapeutic interaction with a target or mechanism selected from the group consisting of:

(a) inhibitors of poly-ADP ribose polymerase;
(b) agents that affect vasculature;
(c) agents that promote vasodilation;
(d) oncogenic targeted agents;
(e) signal transduction inhibitors;
(f) agents inducing EGFR inhibition;
(g) agents inducing Protein Kinase C inhibition;
(h) agents inducing Phospholipase C downregulation;
(i) agents including jun downregulation;
(j) agents modulating expression of histone genes;
(k) agents modulating expression of VEGF;
(l) agents modulating expression of ornithine decarboxylase;
(m) agents modulating expression of jun D;
(n) agents modulating expression of v-jun;
(o) agents modulating expression of GPCRs;
(p) agents modulating expression of protein kinase A;
(q) agents modulating expression of protein kinases other than protein kinase A;
(r) agents modulating expression of telomerase;
(s) agents modulating expression of prostate specific genes; and
(t) agents modulating expression of histone deacetylase.

Inhibitors of poly ADP-ribose polymerase include veliparib (ABT-888), AGO14699, iniparib (BSI-201), carboplatin, gemcitabine, INO-1001, MK4827, nicotinamide, olaparib, paclitaxel, temozolomide, and topotecan, and are described in E. A. Comen & M. Robson, "Inhibition of Poly(ADP)-Ribose Polymerase as a Therapeutic Strategy for Breast Cancer," *Oncology* 24: 55-62 (2010), incorporated herein by this reference. Additional agents that inhibit poly ADP-ribose polymerase are known in the art Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1 (2H)-ones, quinazolinones, isoindolinones, phenanthridinones, and other compounds. Poly-ADP ribose polymerase (PARP) inhibitors include, but are not limited to: (1) derivatives of tetracycline as described in U.S. Pat. No. 8,338,477 to Duncan et al.; (2) 3,4-dihydro-5-methyl-1(2H)-isoquinoline, 3-aminobenzamide, 6-aminonicotinamide, and 8-hydroxy-2-methyl-4(3H)-quinazolinone, as described in U.S. Pat. No. 8,324,282 by Gerson et al.; (3) 6-(5H)-phenanthridinone and 1,5-isoquinolinediol, as described in U.S. Pat. No. 8,324,262 by Yuan et al.; (4) (R)-3-[2-(2-hydroxymethylpyrrolidin-1-yl)ethyl]-5-methyl-2H-isoquinolin-1-one, as described in U.S. Pat. No. 8,309,573 to Fujio et al.; (5) 6-alkenyl-substituted 2-quinolinones, 6-phenylalkyl-substituted quinolinones, 6-alkenyl-substituted 2-quinoxalinones, 6-phenylalkyl-substituted 2-quinoxalinones, substituted 6-cyclohexylalkyl substituted 2-quinolinones, 6-cyclohexylalkyl substituted 2-quinoxalinones, substituted pyridones, quinazolinone derivatives, phthalazine derivatives, quinazolinedione derivatives, and substituted 2-alkyl quinazolinone derivatives, as described in U.S. Pat. No. 8,299,256 to Vialard et al.; (6) 5-bromoisoquinoline, as described in U.S. Pat. No. 8,299,088 to Mateucci et al.; (7) 5-bis-(2-chloroethyl)amino]-1-methyl-2-benzimidazolebutyric acid, 4-iodo-3-nitrobenzamide, 8-fluoro-5-(4-((methylamino) methyl)phenyl)-3,4-dihydro-2H-azepino[5,4,3-cd]indol-1 (6H)-one phosphoric acid, and N-[3-(3,4-dihydro-4-oxo-1-phthalazinyl)phenyl]-4-morpholinebutanamide methanesulfonate, as described in U.S. Pat. No. 8,227,807 to Gallagher et al.; (8) pyridazinone derivatives, as described in U.S. Pat. No. 8,268,827 to Branca et al.; (9) 4-[3-(4-cyclopropanecarbonyl-piperazine-1-carbonyl)-4-fluorobenzyl]-2H-phthalazin-1-one, as described in U.S. Pat. No. 8,247,416 to Menear et al.; (10) tetraaza phenalen-3-one compounds, as described in U.S. Pat. No. 8,236,802 to Xu et al.; (11) 2-substituted-1H-benzimidazole-4-carboxamides, as described in U.S. Pat. No. 8,217,070 to Zhu et al.; (12) substituted 2-alkyl quinazolinones, as described in U.S. Pat. No. 8,188,103 to Van der Aa et al.; (13) 1H-benzimidazole-4-carboxamides, as described in U.S. Pat. No. 8,183,250 to Penning et al.; (13) indenoisoquinolinone analogs, as described in U.S. Pat. No. 8,119,654 to Jagtap et al.; (14) benzoxazole carboxamides, described in U.S. Pat. No. 8,088,760 to Chu et al; (15) diazabenzo[de]anthracen-3-one compounds, described in U.S. Pat. No. 8,058,075 to Xu et al.; (16) dihydropyridophthalazinones, described in U.S. Pat. No. 8,012,976 to Wang et al., (17) substituted azaindoles, described in U.S. Pat. No. 8,008,491 to Jiang et al.; (18) fused tricyclic compounds, described in U.S. Pat. No. 7,956,064 to Chua et al.; (19) substituted 6a,7,8,9-tetrahydropyrido [3,2-e]pyrrolo[1,2-a]pyrazin-6(5H)-ones, described in U.S. Pat. No. 7,928,105 to Gangloff et al.; and (20) thieno[2,3-c]isoquinolines, described in U.S. Pat. No. 7,825,129, all of which patents are incorporated herein by this reference. Other PARP inhibitors are known in the art.

Agents promoting vasodilation include levosimendan, described in W. G. Toiler et al., "Levosimendan, a New Inotropic and Vasodilator Agent," *Anesthesiology* 104: 556-569 (2006), incorporated herein by this reference. EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in H. C. Swannie & S. B. Kaye, "Protein Kinase C Inhibitors," *Curr. Oncol. Rep.* 4: 37-46 (2002), incorporated herein by this reference. Phospholipase C downregulation is described in A. M. Martelli et al., "Phosphoinositide Signaling in Nuclei of Friend Cells: Phospholipase Cβ Downregulation Is Related to Cell Differentiation," *Cancer Res.* 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," *Oncogene* 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986), incorporated herein by this reference. The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surgery* 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002), incorporated herein by this reference. The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," *Oncogene* 27: 5033-5044 (2008), incorporated herein by this reference. The role of v-Jun as a target for therapeutic intervention is described in M. Gao et al., "Differential and Antagonistic Effects of v-Jun and c-Jun," *Cancer Res.* 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," *Ann. Med.* 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002), incorporated herein by this reference.

When the improvement is made by use of selective target cell population therapeutics, the use of selective target cell population therapeutics can be, but is not limited to, a use selected from the group consisting of:
 (a) use against radiation sensitive cells;
 (b) use against radiation resistant cells;
 (c) use against energy depleted cells; and
 (d) use against endothelial cells.

When the improvement is made by use with an agent to enhance the activity of a mustard-based alkylating agent such as uracil mustard, the agent to enhance the activity of the mustard-based alkylating agent can be, but is not limited to, an agent selected from the group consisting of:
 (a) nicotinamide;
 (b) caffeine;
 (c) tetandrine; and
 (d) berberine.

Another aspect of the present invention is a composition to improve the efficacy and/or reduce the side effects of suboptimally administered drug therapy comprising an alternative selected from the group consisting of:
 (i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;
 (ii) a composition comprising:
   (a) a therapeutically effective quantity of a therapeutic agent, a modified therapeutic agent or a derivative, analog, or prodrug of a therapeutic agent or modified therapeutic agent; and
   (b) at least one additional therapeutic agent, therapeutic agent subject to chemosensitization, therapeutic agent subject to chemopotentiation, diluent, excipient, solvent system, drug delivery system, or agent for enhancing the activity or efficacy of the therapeutic agent, the modified therapeutic agent or the derivative, analog, or prodrug of a therapeutic agent or modified therapeutic agent of (a), wherein the composition possesses increased therapeutic efficacy or reduced side effects as compared with an unmodified therapeutic agent;
 (iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;
 (iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and
 (v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent;
wherein the unmodified therapeutic agent is a mustard-based alkylating agent or an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom, the modified therapeutic agent is a modification of a mustard-based alkylating agent or of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom, and the derivative, analog, or prodrug is a derivative, analog, or prodrug of a mustard-based alkylating agent, of a modification of a mustard-based alkylating agent, of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom, or of a modification of an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom.

In one alternative, the unmodified therapeutic agent is uracil mustard.

In another alternative, the unmodified therapeutic agent is a mustard-based alkylating agent selected from the group consisting of:
(1) uracil mustard;
(2) 6-methyluracil mustard;
(3) 6-ethyluracil mustard;
(4) 6-propyluracil mustard;
(5) 3-[1-methyl-4-[1-methyl-4-[1-methyl-4-[N1-[5-bis(2-chloroethyl)amino-2,4-(1H,3H)pyrimidinedione]acetylamino]-pyrrole-2-carboxamido]pyrrole-2-carboxamido]pyrrole-2-carboxamido]propionamidine hydrochloride;
(6) 3-[1-methyl-4-[1-methyl-4-[1-methyl-4-[N1-[5-bis(2-chloroethyl)amino-2,4-(1H,3H)pyrimidinedione]propanoylamino]-pyrrole-2-carboxamido]pyrrole-2-carboxamido]pyrrole-2-carboxamido]propionamidine hydrochloride
(7) 3-[1-methyl-4-[1-methyl-4-[1-methyl-4-[N1-[5-bis(2-chloroethyl)amino-2,4-(1H,3H)pyrimidinedione]butanoylamino]-pyrrole-2-carboxamido]pyrrole-2-carboxamido]pyrrole-2-carboxamido]propionamidine hydrochloride;
(8) 3-[1-methyl-4-[1-methyl-4-[1-methyl-4-[N1-[5-bis(2-chloroethyl)amino-2,4-(1H,3H)pyrimidinedione]pentanoylamino]-pyrrole-2-carboxamido]pyrrole-2-carboxamido]pyrrole-2-carboxamido]propionamidine hydrochloride;
(9) 3-[1-methyl-4-[1-methyl-4-[1-methyl-4-[N1-[5-bis(2-chloroethyl)amino-2,4-(1H,3H)pyrimidinedione]hexanoylamino]-pyrrole-2-carboxamido]pyrrole-2-carboxamido]pyrrole-2-carboxamido]propionamidine hydrochloride;
(10) 3-[1-methyl-4-[1-methyl-4-[1-methyl-4-[N1-[5-bis(2-chloroethyl)amino-2,4-(1H,3H)pyrimidinedione]heptanoylamino]-pyrrole-2-carboxamido]pyrrole-2-carboxamido]pyrrole-2-carboxamido]propionamidine hydrochloride;
(11) estramustine;
(12) derivatives of estramustine;
(13) quinacrine mustard dihydrochloride;
(14) derivatives of quinacrine mustard dihydrochloride;
(15) phosphoramide mustard;
(16) derivatives of phosphoramide mustard;
(17) spiromustine;
(18) derivatives of spiromustine;
(19) mustamine;
(20) derivatives of mustamine;
(21) phenylalanine mustard;
(22) derivatives of phenylalanine mustard;
(23) mannomustine;
(24) derivatives of mannomustine;
(25) 5-((bis(2-chloroethyl)amino)methyl)-pyrimidine-2,4(1H,3H)-dione;
(26) 5-((bis(2-chloroethyl)amino)methyl)-6-methylpyrimidine-2,4(1H,3H)-dione;
(27) 5-((bis(2-chloroethyl)amino)methyl)-1-methylpyrimidine-2,4(1H,3H)-dione;
(28) 5-((bis(2-chloroethyl)amino)methyl)-1,3-dimethylpyrimidine-2,4(1H,3H)-dione;
(29) 5-((bis(2-chloroethyl)amino)methyl)-6-propylpyrimidine-2,4(1H,3H)-dione;
(30) 5-((bis(2-chloroethyl)amino)methyl)-6-methyl-2-thioxo-2,3-dihydropyrimidin-4(1H)-one;
(31) nitrouracil;
(32) 5,6-dihydro-5-nitrouracil;
(33) 5,6-dihydro-5-nitro-1-(4-nitrophenyl)uracil;
(34) 5-nitro-1-(4-nitrophenyl)uracil;
(35) 5,6-dihydro-5-nitro-1(β-D-ribofuranuronic acid ethyl ester)uracil;
(36) 5-nitro-1(β-D-ribofuranuronic acid ethyl ester)uracil;
(37) 5-nitrouracil N-oxide;
(38) prednimustine;
(39) derivatives of prednimustine;
(40) nimustine;
(41) derivatives of nimustine;
(42) ranimustine;
(43) derivatives of ranimustine;
(44) carmustine;
(45) derivatives of carmustine;
(46) lomustine;
(47) derivatives of lomustine;
(48) fotemustine;
(49) derivatives of fotemustine;
(50) ribomustine;
(51) derivatives of ribomustine;
(52) cystemustine;
(53) derivatives of cystemustine;
(54) 4-chlorouracil mustard;
(55) 4-substituted uracil mustard derivatives;
(56) 4-cyanouracil mustard;
(57) 4-nitrouracil mustard;
(58) derivatives of 4-chlorouracil mustard;
(59) derivatives of 4-substituted uracil mustard derivatives;
(60) derivatives of 4-cyanouracil mustard;
(61) derivatives of 4-nitrouracil mustard;
(62) a derivative or analog of uracil mustard or of alternatives (1)-(61) including one or more optional substituents, provided that the optionally substituted amonafide derivative or analog possesses substantially equivalent pharmacological activity to uracil mustard as determined by DNA alkylation activity;
and the derivatives, active metabolites, bioisosteres, salts, and solvates thereof (referred to herein as "Alternatives (1)-(62)").

In another alternative, the therapeutic agent is an alkylating agent having either: (1) a nitrosourea moiety therein and having one haloalkyl moiety covalently bound to the nitrogen of the nitrosourea group not bound to the oxygen; or (2) two haloalkyl moieties bound to a nitrogen atom.

In yet another alternative, the modified therapeutic agent is a modification of uracil mustard.

In yet another alternative, the modified therapeutic agent is a modification of a mustard-based alkylating agent that is selected from the group consisting of Alternatives (1)-(62).

In yet another alternative, the modified therapeutic agent is a modification of an alkylating agent having either: (1) a nitrosourea moiety therein and having one haloalkyl moiety covalently bound to the nitrogen of the nitrosourea moiety not bound to the oxygen; or (2) two haloalkyl moieties bound to a nitrogen atom.

In yet another alternative, the derivative, analog, or prodrug is a derivative, analog, or prodrug of uracil mustard or of a modification of uracil mustard.

In yet another alternative, the derivative, analog, or prodrug is a derivative, analog, or prodrug of a mustard-based alkylating agent that is selected from the group consisting of Alternatives (1)-(62) or of a modification of a mustard-based alkylating agent that is selected from the group consisting of Alternatives (1)-(62).

In yet another alternative, the derivative, analog, or prodrug is a derivative, analog, or prodrug of an alkylating agent having either: (1) a nitrosourea moiety therein and having one haloalkyl moiety covalently bound to the nitrogen of the nitrosourea moiety not bound to the oxygen; or (2) two haloalkyl moieties bound to a nitrogen atom or of a modification of an alkylating agent having either: (1) a nitrosourea moiety therein and having one haloalkyl moiety covalently bound to the nitrogen of the nitrosourea moiety not bound to the oxygen; or (2) two haloalkyl moieties bound to a nitrogen atom.

Typically, the composition possesses increased efficacy or reduced side effects for cancer therapy.

In one alternative, the composition comprises a drug combination comprising:
(i) an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom;
(ii) an additional therapeutic agent selected from the group consisting of:
  (a) fraudulent nucleosides;
  (b) fraudulent nucleotides;
  (c) thymidylate synthetase inhibitors;
  (d) signal transduction inhibitors;
  (e) cisplatin or platinum analogs;
  (f) alkylating agents;
  (g) anti-tubulin agents;
  (h) antimetabolites;
  (i) berberine;
  (j) apigenin;
  (k) colchicine or an analog thereof;
  (l) genistein;
  (m) etoposide;
  (n) cytarabine;
  (o) camptothecins;
  (p) vinca alkaloids;
  (q) topoisomerase inhibitors;
  (r) 5-fluorouracil;
  (s) curcumin;
  (t) NF-κB inhibitors;
  (u) rosmarinic acid;
  (v) mitoguazone;
  (w) meisoindigo;
  (x) imatinib;
  (y) dasatinib;
  (z) nilotinib;
  (aa) epigenetic modulators;
  (ab) transcription factor inhibitors;
  (ac) taxol;
  (ad) homoharringtonine;
  (ae) pyridoxal;
  (af) spirogermanium;
  (ag) caffeine;
  (ah) nicotinamide;
  (ai) methylglyoxalbisguanylhydrazone;
  (aj) Rho kinase inhibitors;
  (ak) 1,2,4-benzotriazine oxides;
  (al) an alkylglycerol;
  (am) an inhibitor of a Mer, Ax1, or Tyro-3 receptor kinase;
  (an) an inhibitor of ATR kinase;
  (ao) a modulator of Fms kinase, Kit kinase, MAP4K4 kinase, TrkA kinase, or TrkB kinase;
  (ap) endoxifen;
  (aq) a mTOR inhibitor;
  (ar) an inhibitor of Mnk1a kinase, Mkn1b kinase, Mnk2a kinase, or Mnk2b kinase;
  (as) a modulator of pyruvate kinase M2;
  (at) a modulator of phosphoinositide 3-kinases;
  (au) a cysteine protease inhibitor;
  (av) phenformin;
  (aw) Sindbis virus-based vectors;
  (ax) peptidomimetics that act as mimetics of Smac and inhibit IAPs to promote apoptosis;
  (ay) a Raf kinase inhibitor;
  (az) a nuclear transport modulator;
  (ba) an acid ceramidase inhibitor and a choline kinase inhibitor;
  (bb) tyrosine kinase inhibitors;
  (bc) anti-CS1 antibodies;
  (bd) inhibitors of protein kinase CK2;
  (be) anti-guanylyl cyclase C (GCC) antibodies;
  (bf) histone deacetylase inhibitors;
  (bg) cannabinoids;
  (bh) glucagon-like peptide-1 (GLP-1) receptor agonists;
  (bi) inhibitors of Bcl-2 or Bcl-xL;
  (bj) Stat3 pathway inhibitors;
  (bk) inhibitors of polo-like kinase 1 (Plk1);
  (bl) GBPAR1 activators;
  (bm) modulators of serine-threonine protein kinase and poly(ADP-ribose) polymerase (PARP) activity;
  (bn) taxanes;
  (bo) inhibitors of dihydrofolate reductase;
  (bp) inhibitors of aromatase;
  (bq) benzimidazole-based anti-neoplastic agents;
  (br) an O6-methylguanine-DNA-methyltransferase (MGMT) inhibitor;
  (bs) CCR9 inhibitors;
  (bt) acid sphingomyelinase inhibitors;
  (bu) peptidomimetic macrocycles;
  (bv) cholanic acid amides;
  (bw) substituted oxazaphosphorines;
  (bx) anti-TWEAK receptor antibodies;
  (by) an ErbB3 binding protein;
  (bz) a glutathione S-transferase-activated anti-neoplastic compound;
  (ca) substituted phosphorodiamidates;
  (cb) inhibitors of MEKK protein kinase;
  (cd) COX-2 inhibitors;
  (ce) cimetidine and a cysteine derivative;
  (cf) anti-IL-6 receptor antibody;
  (cg) an antioxidant;
  (ch) an isoxazole inhibitor of tubulin polymerization;
  (ci) PARP inhibitors;
  (cj) Aurora protein kinase inhibitors;
  (ck) peptides binding to prostate-specific membrane antigen;
  (cl) CD19 binding agents;
  (cm) benzodiazepines;
  (cn) Toll-like receptor (TLR) agonists;
  (co) bridged bicyclic sulfamides;
  (cp) inhibitors of epidermal growth factor receptor kinase;
  (cq) a ribonuclease of the T2 family having actin-binding activity;
  (cr) myrsinoic acid A or an analog thereof;
  (cs) inhibitors of a cyclin-dependent kinase;
  (ct) inhibitors of the interaction between p53 and MDM2;
  (cu) inhibitors of the receptor tyrosine kinase MET;
  (cv) largazole or largazole analogs;
  (cw) inhibitors of AKT protein kinase;
  (cx) 2'-fluoro-5-methyl-β-L-arabinofuranosyluridine or L-deoxythymidine;
  (cy) HSP90 modulators;
  (cz) inhibitors of JAK kinases;
  (da) inhibitors of PDK1 protein kinase;
  (db) PDE4 inhibitors;
  (de) inhibitors of proto-oncogene c-Met tyrosine kinase;
  (df) inhibitors of indoleamine 2,3-dioxygenase;
  (dg) agents that inhibit expression of ATDC (TRIM29);

(dh) proteomimetic inhibitors of the interaction of nuclear receptor
with coactivator peptides;
(di) antagonists of XIAP family proteins;
(dj) tumor-targeted superantigens;
(dk) inhibitors of Pim kinases;
(dl) inhibitors of CHK1 or CHK2 kinases;
(dm) inhibitors of angiopoietin-like 4 protein;
(dn) Smo antagonists;
(do) nicotinic acetylcholine receptor antagonists;
(dp) farnesyl protein transferase inhibitors;
(dq) adenosine A3 receptor antagonists;
(dr) BTK inhibitors;
(ds) FLT-3 inhibitors;
(dt) cancer vaccines;
(du) biologics;
(dv) anti-nausea therapeutic agents;
(dw) cyclophosphamide;
(dx) doxorubicin;
(dy) vincristine (including liposomal formulations);
(dz) prednisone (including delayed release formulations);
(ea) bleomycin;
(eb) dacarbazine;
(ec) bendamustine hydrochloride;
(ed) alemtuzumab;
(ee) ofatumumab;
(ef) obinutuzumab;
(eg) lenalidomide;
(eh) vorinostat;
(ei) pralatrexate;
(ej) panobinostat;
(ek) brentuximab vedotin;
(el) omecetaxine;
(em) cyclin-dependent kinase inhibitors such as substituted pyrazolo[1,5-a]pyrimidines;
(en) 4-(4-methylpiperazin-1-ylmethyl)-N-[4-methyl-3-(4-pyridin-3-yl)pyrimidin-2-ylamino)phenyl]-benzamide;
(eo) CXCR4 inhibitors; and
(ep) tryptamicidin.

Typically, when the alkylating agent is a mustard-based alkylating agent, the mustard-based alkylating agent is uracil mustard. In another alternative, the mustard-based alkylating agent is selected from the group consisting of Alternatives (1)-(62) as described above.

In another alternative, the composition comprises:
(i) an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and
(ii) a therapeutic agent subject to chemosensitization selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) colchicine or an analog of colchicine;
(m) genistein;
(n) etoposide;
(o) cytarabine;
(p) camptothecin;
(q) vinca alkaloids;
(r) 5-fluorouracil;
(s) curcumin;
(t) NF-κB inhibitors;
(u) rosmarinic acid; and
(v) mitoguazone.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the composition comprises:
(i) an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and
(ii) a therapeutic agent subject to chemopotentiation selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) colchicine or an analog of colchicine;
(m) genistein;
(n) etoposide;
(o) cytarabine;
(p) camptothecin;
(q) vinca alkaloids;
(r) 5-fluorouracil;
(s) curcumin;
(t) NF-κB inhibitors;
(u) rosmarinic acid; and
(v) mitoguazone.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the therapeutic agent is subjected to a bulk drug product improvement, wherein the bulk drug product improvement is selected from the group consisting of:
(a) preparation as a free base form;
(b) salt formation;
(c) preparation as a homogeneous crystalline structure;
(d) amorphous structure;

(e) preparation as a pure isomer;
(f) increased purity;
(g) polymorphs;
(h) preparation with lower residual solvent content; and
(i) preparation with lower residual heavy metal content.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In still another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the composition comprises a diluent, wherein the diluent is selected from the group consisting of:
  (a) an emulsion;
  (b) dimethylsulfoxide (DMSO);
  (c) N-methylformamide (NMF)
  (d) dimethylformamide (DMF)
  (e) dimethylacetamide (DMA);
  (f) ethanol;
  (g) benzyl alcohol;
  (h) dextrose-containing water for injection;
  (i) Cremophor;
  (j) cyclodextrins; and
  (k) PEG.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In still another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the composition comprises a solvent system, wherein the solvent system is selected from the group consisting of:
  (a) an emulsion;
  (b) DMSO;
  (c) NMF;
  (d) DMF;
  (e) DMA;
  (f) ethanol;
  (g) benzyl alcohol;
  (h) dextrose-containing water for injection;
  (i) Cremophor;
  (j) PEG; and
  (k) salt systems.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the mustard-based alkylating agent is incorporated into a dosage form selected from the group consisting of:
  (a) tablets;
  (b) capsules;
  (c) topical gels;
  (d) topical creams;
  (e) patches;
  (f) suppositories;
  (g) lyophilized dosage fills;
  (h) immediate-release formulations;
  (i) slow-release formulations;
  (j) controlled-release formulations;
  (k) liquid in capsules;
  (l) 1-mg capsules;
  (m) 5-mg capsules;
  (n) 10-mg capsules;
  (o) 1-mg tablets;
  (p) 5-mg tablets;
  (q) 10-mg tablets;
  (r) coated tablets;
  (s) lyophilized dosages suitable for intravenous administration;
  (t) stable liquid formulations; and
  (u) stabilized compositions comprising a non-aqueous carrier.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the mustard-based alkylating agent is incorporated into a dosage kit and packaging selected from the group consisting of amber vials to protect from light and stoppers with specialized coatings to improve shelf-life stability.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In still another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the composition comprises a drug delivery system selected from the group consisting of:
  (a) oral dosage forms;
  (b) nanocrystals;
  (c) nanoparticles;
  (d) cosolvents;
  (e) slurries;
  (f) syrups;
  (g) bioerodible polymers;
  (h) liposomes;
  (i) slow-release injectable gels;
  (j) microspheres;
  (k) targeting compositions with epidermal growth factor receptor-binding peptides;

(l) bispecific antibody pretargeting;
(m) single chain variable region antibody fragments cloned by phage display; and
(n) polymeric micelles for drug delivery.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the alkylating agent is present in the composition in a drug conjugate form selected from the group consisting of:
(a) a polymer system;
(b) polylactides;
(c) polyglycolides;
(d) amino acids;
(e) peptides;
(f) multivalent linkers;
(g) immunoglobulins;
(h) cyclodextrin polymers;
(i) modified transferrin;
(j) hydrophobic or hydrophobic-hydrophilic polymers;
(k) conjugates with a phosphonoformic acid partial ester;
(l) conjugates with a cell-binding agent incorporating a charged cross-linker;
(m) conjugates with β-glucuronides through a linker;
(n) conjugates with anti-CD-49 antibodies;
(o) conjugates with activatable compounds;
(p) conjugates with targetable constructs;
(q) charged or pro-charged conjugates of cell-binding agents;
(r) conjugates with anti-CD74 antibodies, typically with the administration of fingolimod;
(s) conjugates with anti-GITR antibodies;
(t) conjugates with hypoxia-selective, weakly basic 2-nitroimidazole delivery agents;
(u) conjugates with a water-soluble non-peptidic polymer;
(v) conjugates with a hydrohalide salt of a multi-arm water-soluble polyethylene glycol;
(w) conjugates with pheophorbide-α;
(x) conjugates with cancer-targeting peptides, in which the cancer-targeting peptides have a $PX_1LX_2$ motif, in which $X_1$ is His or an amino acid residue with a hydrophobic side chain and $X_2$ is Pro, Phe, or Trp;
(y) conjugates with a bioactive assembly formed using dock-and-lock methodology which takes advantage of the specific binding interaction between dimerization and docking domains (DDD) and anchoring domains (AD) to form the assembly; and
(z) conjugates with a hexavalent molecular building block, wherein the linkage of additional moieties to the amino and carboxyl terminals of monomers comprising the NC2 domain of collagen IX promotes the directed association of those moieties via the trimerization initiating and stagger determining capacity of the NC2 domain of collagen IX, and wherein the NC2 domain of collagen X is conjugated to uracil mustard.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the therapeutic agent is a modified alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the modification is selected from the group consisting of:
(a) alteration of side chains to increase or decrease lipophilicity;
(b) addition of an additional chemical functionality to alter a property selected from the group consisting of reactivity, electron affinity, and binding capacity;
(c) alteration of salt form; and
(d) attachment of nitroxide free-radical-containing groups.

Typically, in this composition, when the modified alkylating agent is a modified mustard-based alkylating agent, the modified mustard-based alkylating agent is a modified uracil mustard. In another alternative, when the modified alkylating agent is a modified mustard-based alkylating agent, the modified mustard-based alkylating agent is a modified mustard-based alkylating agent that is a modified mustard-based alkylating agent selected from modified Alternatives (1)-(62).

In still another alternative of a composition according to the present invention, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the therapeutic agent is in the form of a prodrug system, wherein the prodrug system is selected from the group consisting of:
(a) the use of enzyme sensitive esters;
(b) the use of dimers;
(c) the use of Schiff bases;
(d) the use of pyridoxal complexes;
(e) the use of caffeine complexes;
(f) the use of nitric oxide-releasing prodrugs; and
(g) the use of prodrugs with fibroblast activation protein α-cleavable oligopeptides.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In yet another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the composition further comprises at least one additional therapeutic agent to form a multiple drug system, wherein the at least one additional therapeutic agent is selected from the group consisting of:
(a) inhibitors of multi-drug resistance;
(b) specific drug resistance inhibitors;
(c) specific inhibitors of selective enzymes;
(d) signal transduction inhibitors;
(e) meisoindigo;

(f) imatinib;
(g) hydroxyurea;
(h) dasatinib;
(i) capecitabine;
(j) nilotinib;
(k) repair inhibition agents;
(l) topoisomerase inhibitors with non-overlapping side effects; and
(m) anti-nausea medications.

Typically, when the alkylating agent is a mustard-based alkylating agent, the mustard-based alkylating agent is uracil mustard. In another alternative, the mustard-based alkylating agent is selected from the group consisting of Alternatives (1)-(62).

In still another alternative, the therapeutic agent is an alkylating agent selected from the group consisting of: (1) a mustard-based alkylating agent; and (2) an alkylating agent having either: (A) a nitrosourea moiety therein and having one haloalkyl moiety covalently bound to the nitrogen of the nitrosourea moiety not bound to the oxygen; or (B) two haloalkyl moieties bound to a nitrogen atom; and the composition further comprises at least one agent for enhancing the activity or efficacy of the alkylating agent, wherein the at least one agent for enhancing the activity or efficacy of the alkylating agent is selected from the group consisting of:
  (i) nicotinamide;
  (ii) caffeine;
  (iii) tetandrine; and
  (iv) berberine.

Typically, when the alkylating agent is a mustard-based alkylating agent, the mustard-based alkylating agent is uracil mustard. In another alternative, the mustard-based alkylating agent is selected from the group consisting of Alternatives (1)-(62).

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992), all incorporated herein by this reference.

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg. In particular, for mustard-based alkylating agents such as uracil mustard, suitable doses typically are from about 50 mg/m$^2$ to about 500 mg/m$^2$ or from about 0.1 mg/kg to about 10 mg/kg.

Plasma concentrations in the subjects may be between about 100 µM to about 1000 µM. In some embodiments, the plasma concentration may be between about 200 µM to about 800 µM. In other embodiments, the concentration is about 300 µM to about 600 µM. In still other embodiments the plasma concentration may be between about 400 to about 800 µM. Administration of prodrugs is typically dosed at weight levels which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in a conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-$\alpha$-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime if desired, depending on the disease or condition.

For the purposes of the present application, treatment can be monitored by observing one or more of the improving symptoms associated with the disease, disorder, or condition being treated, or by observing one or more of the improving clinical parameters associated with the disease, disorder, or condition being treated, as described above. Compositions and methods according to the present invention are not limited to treatment of humans, but are applicable to treatment of socially or economically important animals, such as dogs, cats, horses, cows, sheep, goats, pigs, and other animal species of social or economic importance. Unless specifically stated, compositions and methods according to the present invention are not limited to the treatment of humans.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins, carbohydrates, and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 to Nardella, U.S. Pat. No. 6,921,722 by Nardella, U.S. Pat. No. 7,314,886 to Chao et al., and U.S. Pat. No. 7,446,122 to Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

Advantages of the Invention

The present invention provides more effective and efficient methods of using therapeutic drugs that have previously been evaluated for treatment of a number of diseases and conditions, especially hyperproliferative disorders, but whose evaluations resulted in a premature conclusion of lack of sufficient efficacy or of occurrence of side effects sufficient to prevent the use of the therapeutic drug. Such more effective and efficient methods of therapeutic drugs will improve efficacy, prevent or reduce the occurrence of significant side effects, and will identify categories of patients and situations in which such drugs can be effectively employed. Such drugs particularly include mustard-based alkylating agents, such as uracil mustard, 6-methyluracil mustard, and 6-ethyluracil mustard.

Methods according to the present invention possess industrial applicability for the preparation of a medicament for the treatment of a number of diseases and conditions, especially hyperproliferative diseases, and compositions according to the present invention possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method to improve the efficacy and/or reduce the side effects of suboptimally administered drug therapy comprising the steps of:
   (a) identifying at least one factor or parameter associated with the efficacy and/or occurrence of side effects of the drug therapy; and
   (b) modifying the factor or parameter to improve the efficacy and/or reduce the side effects of the drug therapy;
   wherein the drug therapy comprises administering uracil mustard in a therapeutically effective quantity;
   wherein the factor or parameter is dose modification;
   wherein the uracil mustard is administered to treat a hyperproliferative disease, wherein the hyperproliferative disease is cancer and wherein the cancer is selected from the group consisting of chronic lymphocytic leukemia, follicular lymphoma, lymphocytic lymphoma, chronic myelogenous leukemia, ovarian carcinoma, and carcinoma of the lung; and wherein administration of the uracil mustard achieves a reduction in myelosuppression or an increase in response rate to the uracil mustard for at least one of chronic lymphocytic leukemia, follicular lymphoma, lymphocytic lymphoma, chronic myelogenous leukemia, ovarian carcinoma, and carcinoma of the lung in order to treat the malignancy; and
   wherein the dose modification is selected from the group consisting of:
   (a) doses greater than 5 mg/m$^2$/day;
   (b) doses less than 1 mg/m$^2$ for greater than 14 days;
   (c) bolus single and multiple doses of 1-5 mg/m$^2$;
   (d) dosages of 0.15 mg/kg;
   (e) dosages of 0.30 mg/kg;
   (f) dosages of 0.45 mg/kg;
   (g) dosages of 0.60 mg/kg;
   (h) dosages above 0.15 mg/kg/day to 1 mg/kg/wk;
   (i) dosages above 1 mg/day to 4 mg/day; and
   (j) dosages above 0.15 mg/kg every 2 weeks to 1 mg/kg for three days per week.

2. The method of claim 1, wherein the dose modification is selected from the group consisting of dosages of 0.15 mg/kg, dosages of 0.30 mg/kg, dosages of 0.45 mg/kg, and dosages of 0.60 mg/kg.

* * * * *